United States Patent
Kim et al.

(10) Patent No.: US 9,539,345 B2
(45) Date of Patent: Jan. 10, 2017

(54) METHOD TO IMPROVE THE TUMOR DIAGNOSTIC EFFICIENCY OF MULTIVALENT LIGANDS BY REGULATING THE STOICHIOMETRIC RATIO BETWEEN INNER SURFACE FUNCTIONALITIES AND LIGAND MOIETIES FOR TUMOR TARGETING

(71) Applicants: KOREA RESEARCH INSTITUTE OF BIOSCIENCE AND BIOTECHNOLOGY, Daejeon (KR); NATIONAL CANCER CENTER, Goyang-si, Gyeonggi-do (KR)

(72) Inventors: Yoonkyung Kim, Seoul (KR); Ju Young Heo, Daegu (KR); June-key Chung, Seoul (KR); Young-Hwa Kim, Seoul (KR); Seok Ki Kim, Goyang-si (KR); Se Hun Kang, Goyang-si (KR)

(73) Assignees: Korea Research Institute of Bioscience and Biotechnology, Daejeon (KR); National Cancer Center, Goyang-Si (KR)

( * ) Notice: Subject to any disclaimer, the term of this patent is extended or adjusted under 35 U.S.C. 154(b) by 30 days.

(21) Appl. No.: 14/254,365

(22) Filed: Apr. 16, 2014

(65) Prior Publication Data
US 2015/0265731 A1 Sep. 24, 2015

(30) Foreign Application Priority Data
Mar. 21, 2014 (KR) .................. 10-2014-0033724

(51) Int. Cl.
*A61K 51/08* (2006.01)
*A61K 49/00* (2006.01)
*A61K 51/06* (2006.01)

(52) U.S. Cl.
CPC ....... *A61K 49/0002* (2013.01); *A61K 49/0032* (2013.01); *A61K 49/0054* (2013.01); *A61K 49/0056* (2013.01); *A61K 51/065* (2013.01); *A61K 51/082* (2013.01)

(58) Field of Classification Search
CPC ......... A61K 48/00; A61K 51/00; A61K 47/48
See application file for complete search history.

(56) References Cited

U.S. PATENT DOCUMENTS 6,471,968 B1 * 10/2002 Baker et al. .............. 424/280.1
2009/0104119 A1 * 4/2009 Majoros ........... A61K 47/48207
514/1.1

OTHER PUBLICATIONS

Haijun Yu et al., Epidermal Growth Factor—PEG Functionalized PAMAM—Pentaehtylenehexamine Dendron for Targeted Gene Delivery Produced by Click Chemistry, BioMacromolucules, 2011, 12, 2039-2047.*
Albertazzi et al., Dendrimer-Based Fluorescent Indicators: In Vitro and In Vivo Applications, PLoS One 6(12) e28450.*
Kim et al. (2011), "Tumor Targeting and Imaging Using Cyclic RGD-PEGylated Gold Nanoparticle Probes with Directly Conjugated Iodine-125", Biomedical Applications, small 2011, 7, No. 14, 2052-2060.
Banerjee et al. (2011), "Sequential SPECT and Optical Imaging of Experimental Models of Prostate Cancer with a Dual Modality Inhibitor of the Prostate-Specific Membrane Antigen", Angew. Chem. Int. Ed. 2011, 50, 9167-9170.
Hak et al. (2012), "The Effect of Nanoparticle Polyethylene Glycol Surface Density on Ligand-Directed Tumor Targeting Studied in Vivo by Dual Modality Imaging", ACSNANO, vol. 6 , No. 6, 5648-5658.
Zern et al. (2013), "Reduction of Nanoparticle Avidity Enhances the Selectivity of Vascular Targeting and PET Detection of Pulmonary Inflammation," ACSNANO, vol. 7 , No. 3, 2461-2469.
Stefanick et al. (2013), "A Systematic Analysis of Peptide Linker Length and Liposomal Polyethylene Glycol Coating on Cellular Uptake of Peptide-Targeted Liposomes", ACSNANO, vol. 7 , No. 4, 2935-2947.
Parrott et al. (2009), "Synthesis, Radiolabeling, and Bio-imaging of High-Generation Polyester Dendrimers", J. Am. Chem. Soc. 2009, 131, 2906-2916.
Grochmal et al. (2013), "Modulation of In-Membrane Receptor Clustering upon Binding of Multivalent Ligands", J. Am. Chem. Soc. 2013, 135, 10172-10177.
Zhang et al. (2010), "Synthesis, Biodistribution, and Microsingle Photon Emission Computed Tomography (SPECT) Imaging Study of Technetium-99m Labeled PEGylated Dendrimer Poly(amidoamine) (PAMAM)-Folic Acid Conjugates", J. Med. Chem. 2010, 53, 3262-3272.

* cited by examiner

*Primary Examiner* — Michael G Hartley
*Assistant Examiner* — Jagadishwar Samala
(74) *Attorney, Agent, or Firm* — Lathrop & Gage LLP

(57) ABSTRACT

Disclosed herein is a method of improving tumor diagnostic efficiency of multivalent ligands by regulating the stoichiometric ratio between inner surface functionalities and ligand moieties for tumor targeting, and the multivalent ligands for tumor diagnosis.

9 Claims, 7 Drawing Sheets

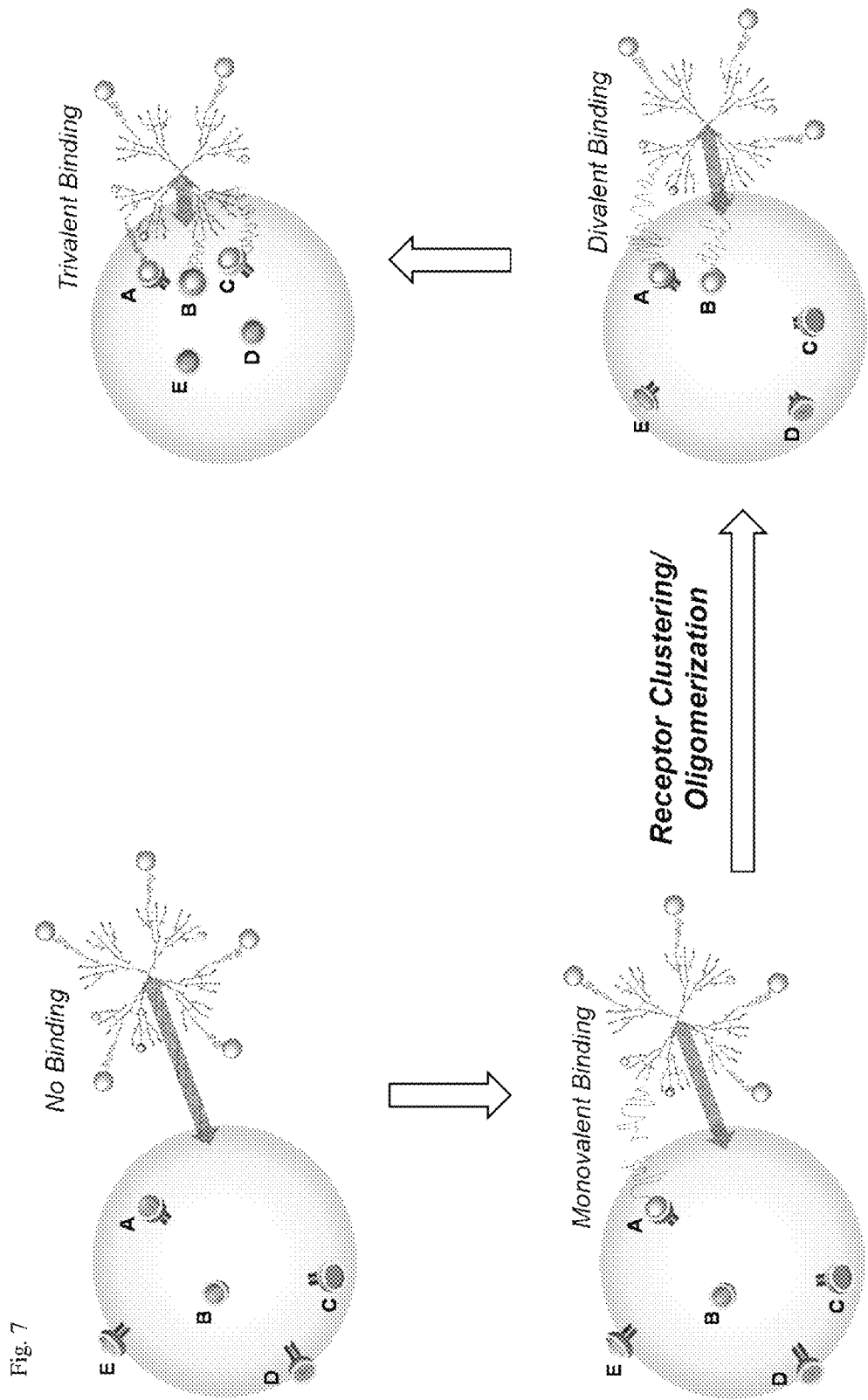

US 9,539,345 B2

METHOD TO IMPROVE THE TUMOR DIAGNOSTIC EFFICIENCY OF MULTIVALENT LIGANDS BY REGULATING THE STOICHIOMETRIC RATIO BETWEEN INNER SURFACE FUNCTIONALITIES AND LIGAND MOIETIES FOR TUMOR TARGETING

CROSS-REFERENCES TO RELATED APPLICATION

This patent application claims the benefit of priority from Korean Patent Application No. 10-2014-0033724, filed on Mar. 21, 2014, the contents of which are incorporated herein by reference.

BACKGROUND OF THE INVENTION

1. Field of the Invention

The present disclosure relates to a method of improving tumor diagnostic efficiency of multivalent ligands by regulating the stoichiometric ratio between inner surface functionalities and ligand moieties for tumor targeting, and the multivalent ligands for tumor diagnosis.

2. Description of the Related Art

With the rapid development of modern diagnostic medical imaging equipments, it has become essential to develop contrast media with excellent sensitivity, accuracy, and safety to treat cancer which is the most common intractable disease for the modern people. Examples of imaging techniques that are used for the diagnosis of tumor include magnetic resonance imaging (MRI), computed tomography (CT), ultrasound, and positron emission tomography (PET) and single-photon emission computerized tomography (SPECT which use radioisotopes. Among them, CT and MRI provide anatomical images of human bodies, whereas nuclear medicine imaging methods such as PET and SPECT provide functional images of human bodies (information on physiological and biochemical reactions in vivo) by administering the radiolabeled ligand into a living body which binds strongly to a specific region.

PET and SPECT are one of the most frequently used techniques in nuclear medicine molecular imaging. Nuclear medicine imaging is a method in which a reconstructed image is obtained by measuring the emitted radiation from the radiolabeled imaging agent that was administered in vivo. A gamma ray is used as the radiation in nuclear medicine imaging which has high penetration efficiency against the tissue layer to afford images of superior sensitivity ex vivo; however the image resolution is poor. PET and SPECT are classified according to the principle of generating gamma rays from the radioisotope. PET detects two gamma rays generated when the positron and electron undergo pair annihilation, while SPECT detects a photon released when a nuclide in the excited state is destroyed by using a gamma camera, where a three dimensional image can be obtained by rotating the camera for detection. PET and SPECT are often used to examine or monitor thyroid diseases, cerebral diseases, heart diseases, blood circulation, etc., and are the molecular imaging techniques which have been frequently used to date despite the danger of radiation exposure because of their advantages of possibly detecting early-stage tumors. Additionally, the radiolabeled compounds for in vivo injection to obtain nuclear medicine images can be used as radiotherapeutic agents as well as imaging probes. As such, it is very important to develop such compounds with improved safety and efficiency.

Generally, multivalent ligands contain two or more ligand moieties within a molecule that bind noncovalently to a specific receptor or substrate, and they have high avidity through the multivalent effect which is not present in the molecule that can only bind monovalently to a receptor. Accordingly, such multivalent ligands have been widely used in the development of therapeutic agents for the diagnosis and treatment of diseases where stronger binding of these agents through avidity to the receptors expressed on the cell surface becomes more advantageous. Recently, the research on multivalent ligands for tumor diagnosis based on various organic or inorganic macromolecules and nanoparticles has been actively pursued (non-patent documents 1 to 8).

Tumor cells are generally known to overexpress various receptors as compared to normal cells, and numerous studies have been conducted on the development of targeted nanocarriers for the diagnosis of diseases or drug delivery, which can bind specifically to such receptors. However, these receptors can be partially expressed in normal cells as well as the tumor cells, and thus the nanocarriers may be deposited near the normal cells to exhibit unwanted toxicity. In an effort to overcome these problems, recently the nanocarriers with two or more ligand moieties attached on their surface which can bind to the same type of individual receptors on the surface of the same tumor cell have been reported to improve the selectivity and binding affinity toward the tumor cell.

However, the above reports are limited in that it may be difficult to control the number of maximally attached ligands consistently due to the steric hindrance during the preparation, or not all of the ligand moieties on a multivalent ligand could participate in binding to the receptors even if the multivalent ligand has been made to contain maximally achievable number of ligand moieties because of the limiting factors such as the size of the core and the distance between receptors expressed on the same cell.

In this regard, in order to resolve the above-mentioned problems, instead of substituting the surface of the scaffold or the core with a maximum number of ligand moieties, which has been considered as the most efficient method, the inventors of the present invention completed the present invention by discovering the effect that the avidity has been significantly improved by regulating the stoichiometric ratio between inner surface functionalities and ligand moieties for tumor targeting by the following: Once a ligand moiety of the multivalent ligand binds to a specific receptor expressed on the surface of a tumor cell, the phenomenon of receptor clustering is initiated whereby the same type of receptors migrate toward the receptor bound to the ligand moiety, making it more favorable for the unassociated ligand moieties to engage in multivalent binding. Furthermore, the appropriately selected inner surface functionality which has been then positioned in closer proximity to the cell surface by the bound ligand moieties can interact attractively with the surface of a tumor cell to promote the additional binding of unassociated ligand moieties to the clustered receptors.

Non-Patent Documents

Y.-H. Kim, et al. Small 2011, 7, 2052-2060.
S. R. Banerjee, et al. Angew. Chem. Int. Ed. 2011, 50, 9167-9170.
S. Hak, et al. ACS Nano 2012, 6, 5648-5658.
B. J. Zern, et al. ACS Nano 2013, 7, 2461-2469.
J. F. Stefanick, et al. ACS Nano 2013, 7, 2935-2947.

M. C. Parrot, et al. J. Am. Chem. Soc. 2009, 131, 2906-2916.

A. Grochmal, et al. J. Am. Chem. Soc. 2013, 135, 10172-10177.

Y. Zhang, et al. J. Med. Chem. 2010, 53, 3262-3272.

SUMMARY OF THE INVENTION

One object of the present invention is to provide a method to improve the tumor diagnostic efficiency of multivalent ligands by regulating the stoichiometric ratio between inner surface functionalities and ligand moieties for tumor targeting.

Another object of the present invention is to provide a multivalent ligand wherein the stoichiometric ratio between inner surface functionalities and ligand moieties for tumor targeting is regulated.

In order to achieve the objects, the present invention provides a method to improve the tumor diagnostic efficiency of multivalent ligands by regulating the stoichiometric ratio between inner surface functionalities and ligand moieties for tumor targeting.

Specifically, the number of ligand moieties for tumor targeting preferably accounts for 5-90% of the total number of inner surface functionalities and ligand moieties for tumor targeting, and more preferably 10-60%.

Also, the present invention provides a multivalent ligand which includes a core consisting of a circular or spherical symmetric small molecular compound, or a radial-shaped macromolecule;

an inner surface functionality which is the modified terminal functional group of the core;

a ligand moiety which is attached to a portion of the terminal functional groups of the core through the spacer; and one or more imaging agents which are attached to a portion of the terminal functional groups of the core.

BRIEF DESCRIPTION OF THE DRAWINGS

FIG. 7 illustrates the stepwise diagram showing the multivalent binding between the ligand moieties of a multivalent ligand according to the present invention and the receptors expressed on the surface of a single tumor cell.

DESCRIPTION OF THE PREFERRED EMBODIMENTS

Features and advantages of the present invention will be more clearly understood by the following detailed description of the present preferred embodiments by reference to the accompanying drawings. First, it should be noted that the terms or words used herein should be construed as meanings or concepts corresponding to the technical sprit of the present invention, based on the principle that the inventor can appropriately define the concepts of the terms to best describe his or her own invention. Also, it should be understood that detailed descriptions of well-known functions and structures related to the present invention will be omitted so as not to unnecessarily obscure the important point of the present invention.

Hereinafter, the present invention will be described in detail.

Figure 1:
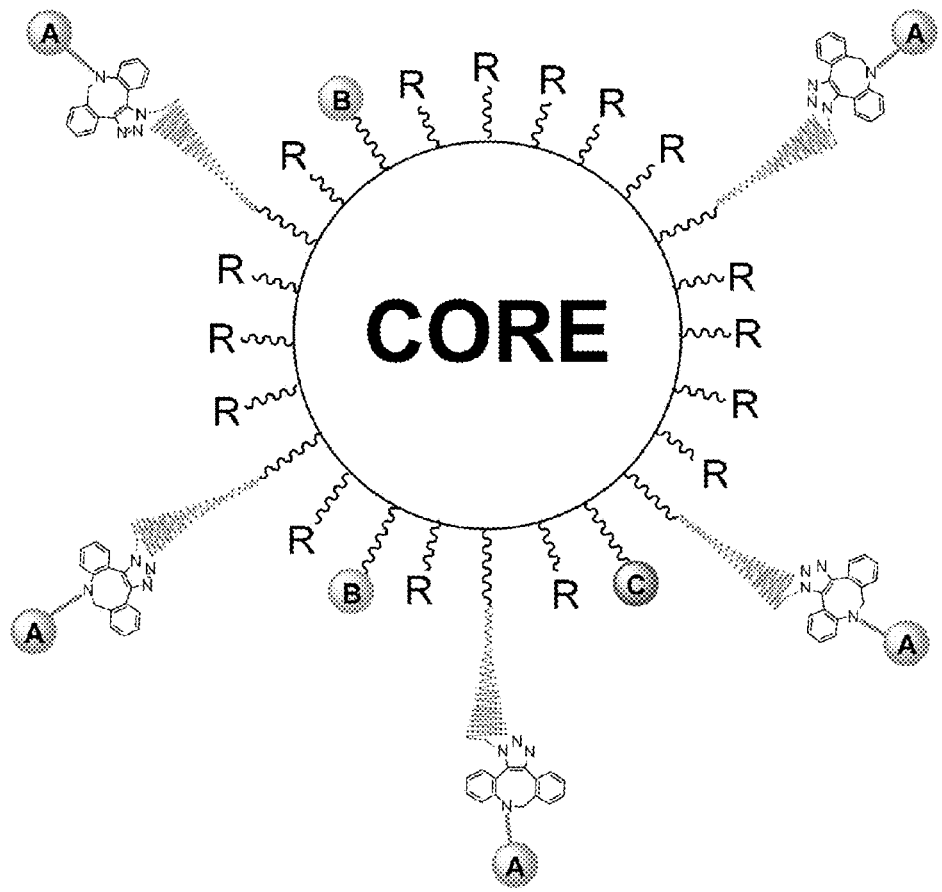
FIG. 1 illustrates the schematic diagram of the multivalent ligands according to the present invention.
Figure 2:
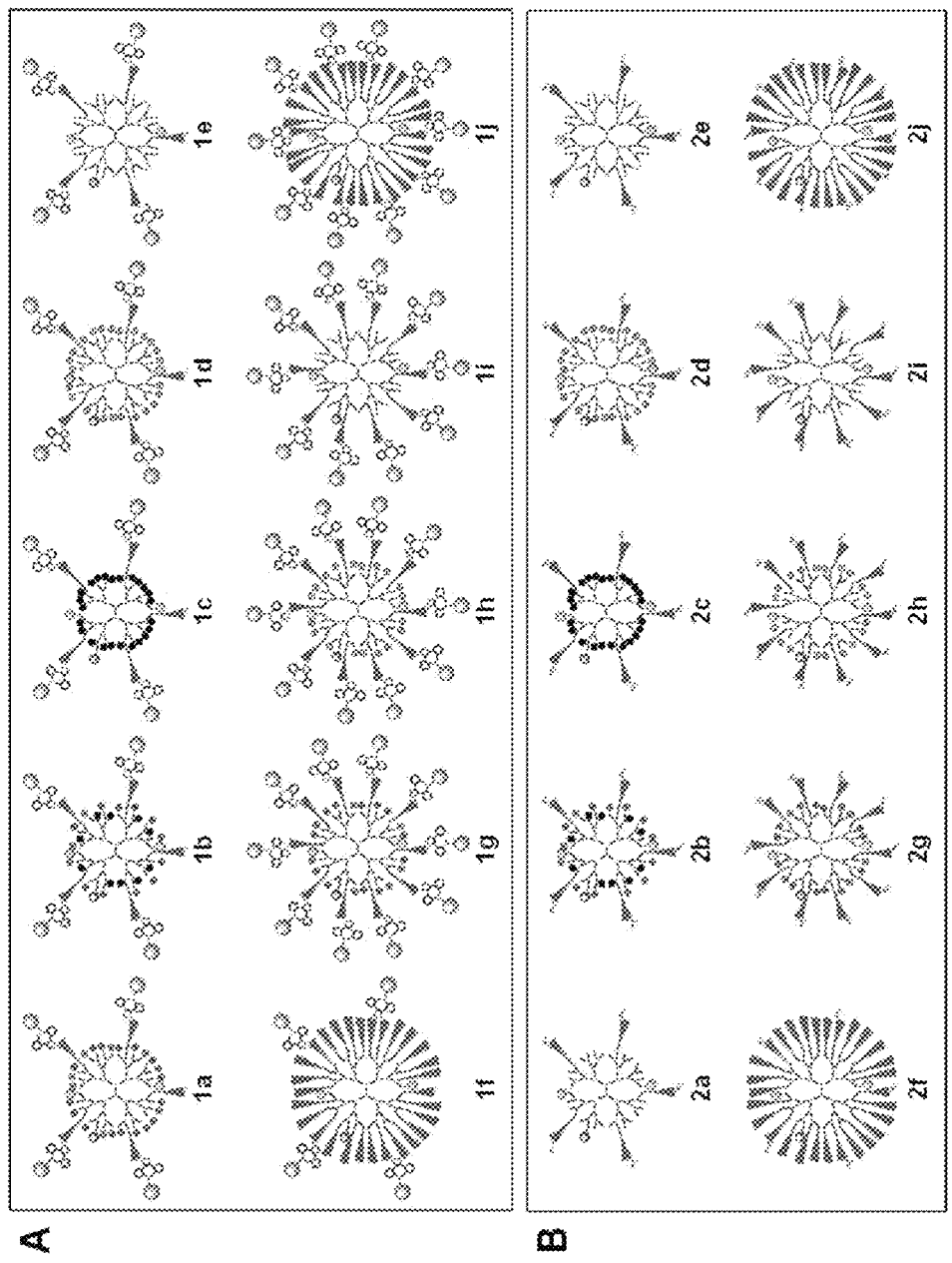
FIG. 2 illustrates (A) the structural formulae of multivalent ligands 1a-1j with the tumor targeting ligand moieties according to the present invention, and (B) the structural formulae of the dendrimer conjugate Compounds 2a-2j without the ligand moieties which are the synthetic precursors of the multivalent ligands mentioned above.

The present invention provides a method to improve the tumor diagnostic efficiency of multivalent ligands by regulating the stoichiometric ratio between inner surface functionalities and ligand moieties for tumor targeting. The schematic diagram representing the multivalent ligand according to the present invention is shown in FIG. 1.

In general, due to the steric hindrance imposed by the neighboring ligand moieties and the spacers which were used to attach ligand moieties to the core, it may be difficult to derivatize all available surface groups of the core with the ligand moieties. Additionally, even if the ligand moieties have been attached maximally to the core either directly or through spacers, not all of the ligand moieties on a multivalent ligand can participate in binding to the receptors on the surface of tumor cells because of the limiting factors such as the size of the core of a multivalent ligand, conformational flexibility, and the distance between receptors expressed on the same tumor cell.

The method according to the present invention of improving tumor diagnostic efficiency of multivalent ligands by regulating the stoichiometric ratio between inner surface functionalities and ligand moieties for tumor targeting has the feature of significantly improving the avidity by the following: Once a ligand moiety of the multivalent ligand binds to a specific receptor expressed on the surface of a tumor cell, the phenomenon of receptor clustering is initiated whereby the same type of receptors migrate toward the receptor bound to the ligand moiety, making it more favorable for the unassociated ligand moieties to engage in multivalent binding. Furthermore, the appropriately selected inner surface functionality which has been then positioned in closer proximity to the cell surface by the bound ligand moieties can interact attractively with the surface of a tumor cell to promote the additional binding of unassociated ligand moieties to the clustered receptors (see FIG. 7).

From the viewpoint of improving the above-mentioned avidity, in the method of improving the tumor diagnostic efficiency according to the present invention, the number of ligand moieties may be regulated to account for preferably 5-90% of the total number of inner surface functionalities and ligand moieties for tumor targeting, and more preferably 10-60%. Here, the number of ligand moieties for tumor targeting can be regulated by controlling the amount of ligand for tumor targeting added during the synthesis.

If the composition of the ligand moieties for tumor targeting is regulated to be below 5%, the chances for a ligand moiety to initially bind to the receptor expressed on the tumor cell surface can be low due to the insufficient number of ligand moieties. In contrast, if the composition of the ligand moieties for tumor targeting exceeds 90%, the binding strength may not increase anymore once the number of ligand moieties of a multivalent ligand simultaneously bound to the different receptors on the surface of the same cell reaches a certain level. This is presumably because the maximally achievable distance between two different ligand moieties within the same multivalent ligand is limited by the length of the spacer and the size of the core. Accordingly, the ligand moieties which did not participate in binding to the receptors may rather interfere to lower the avidity by imposing steric hindrance on the additional binding of the ligand moieties to the receptors. For example, if there are 5 ligand moieties in total within a multivalent ligand and the ligand moieties are positioned adjacently to one another starting from (1) to (5) in sequence, the chances of the ligand moiety (1) to initially bind to a receptor on the surface of a tumor cell may be high; however, the subsequent binding of the ligand moiety (5) which is positioned in close vicinity to another receptor may experience steric hindrance to lower the avidity imposed by ligand moieties (2), (3), and (4) adjacent to the ligand moiety (1) which have initially bound to the receptor during the process of forming a multivalent bond.

In the present invention, the inner surface functionality serves the role of interacting with the surface of tumor cells, wherein the terminal functional group of the core may be modified to one selected from the group consisting of —OH, —OR, —NH$_2$, —NR$_2$, —NHC(=O)CH$_2$, —NHC(=O)CR$_3$, —SH, —SR, —C(=O)OH, —C(=O)OR, —C(=O)R, —C(=O) NR$_2$, —NHC(=O)NR$_2$, —C(=S)NR$_2$, —NHC(=S)NR$_2$, —(OCH$_2$CH$_2$)$_n$OCH$_3$, and —(OCH$_2$CH$_2$)$_n$OR, wherein R is H, or a linear or branched C$_{1-6}$ alkyl group, and n is an integer between 1 and 100. Additionally, if the terminal functional group of the core is identical to the inner surface functionality, the modification process of the terminal functional group of the core may be omitted.

In the method according to the present invention, any ligand moieties that can bind specifically to the receptors expressed on the surface of tumor cells can be used as the ligand moieties for tumor targeting without any particular limitation. In general, it is well known that each receptor has the corresponding ligand that specifically binds to that particular receptor, and each tumor has the receptor that is overexpressed on the surface of that particular tumor. As such, in order to diagnose a specific tumor, the corresponding ligand moiety which binds specifically to the receptor overexpressed on the surface of that particular tumor can be used.

In another exemplary embodiment of the present invention, a multivalent ligand for tumor diagnosis is provided, comprising:

a core consisting of a circular or spherical symmetric small molecular compound, or a radial-shaped macromolecule;

an inner surface functionality which is the terminal functional group of the core;

a ligand moiety which is attached to a portion of the terminal functional groups of the core through the spacer; and one or more imaging agents which are attached to a portion of the terminal functional groups of the core, wherein the stoichiometric ratio between surface functionalities and ligand moieties for tumor targeting is regulated.

For the multivalent ligand according to the present invention, the number of ligand moieties for tumor targeting may be regulated to account for preferably 5-90% of the total number of inner surface functionalities and ligand moieties for tumor targeting, and more preferably 10-60%. Here, the number of ligand moieties for tumor targeting can be regulated by controlling the amount of ligand for tumor targeting added during the synthesis.

If the composition of the ligand moieties for tumor targeting is regulated to be below 5%, the chances for a ligand moiety to initially bind to the receptor expressed on the tumor cell surface can be low due to the insufficient number of ligand moieties. In contrast, if the composition of the ligand moieties for tumor targeting exceeds 90%, the binding strength may not increase anymore once the number of ligand moieties of a multivalent ligand simultaneously bound to the different receptors on the surface of the same cell reaches a certain level. This is presumably because the maximally achievable distance between two different ligand moieties within the same multivalent ligand is limited by the length of the spacer and the size of the core. Accordingly, the ligand moieties which did not participate in binding to the receptors may rather interfere to lower the avidity by imposing steric hindrance on the additional binding of the ligand moieties to the receptors. For example, if there are 5 ligand moieties in total within a multivalent ligand and the ligand moieties are positioned adjacently to one another starting from (1) to (5) in sequence, the chances of the ligand moiety (1) to initially bind to a receptor on the surface of a tumor cell may be high; however, the subsequent binding of the ligand moiety (5) which is positioned in close vicinity to another receptor may experience steric hindrance to lower the avidity imposed by ligand moieties (2), (3), and (4) adjacent to the ligand moiety (1) which have initially bound to the receptor during the process of forming a multivalent bond Hereinafter, the multivalent ligand according to the present invention will be described in detail by its components.

Regarding the multivalent ligand according to the present invention, 1) the circular or spherical symmetric small molecular compound constituting the core may be one of the carbohydrates selected from the group consisting of α-, β-, and γ-cyclodextrins, glucose, galactose, and mannose; porphyrin; 1,4,7,10-tetraazacyclododecane-1,4,7,10-tetraacetic acid (DOTA); a cyclic peptide formed by connecting 2 to 4 amino acids wherein the amino acid is one or more selected from the group consisting of lysine, aspartic acid, glutamic acid, serine, cysteine, and tyrosine; and 2) the radial-shaped macromolecule constituting the core may be one selected from the group consisting of: one of the dendrimers selected from the group consisting of a polyamidoamine (PAMAM) dendrimer, a polylysine dendrimer, a polyimine (PI) dendrimer, a poly(propylene imine) (PPI) dendrimer, a polyester dendrimer, a polyether dendrimer, a polyglutamic acid dendrimer, a polyaspartic acid dendrimer, a polyglycerol dendrimer, and a polymelamine dendrimer; one of the hyperbranched polymers selected from the group consisting of polylysine, polyester, polyether, polyglutamic acid, polyaspartic acid, and polyglycerol; and one of the star-shaped polymers selected from the group consisting of polyethylene glycol (PEG) and copolymers thereof.

Regarding the multivalent ligands according to the present invention, the inner surface functionality serves the role of interacting with the surface of tumor cells, wherein the terminal functional group of the core may be modified to one selected from the group consisting of —OH, —OR, —NH$_2$, —NR$_2$, —NHC(=O)CH$_3$, —NHC(=O)CR$_3$, —SH, —SR, —C(=O)OH, —C(=O)OR, —C(=O)R, —C(=O)NR$_2$, —NHC(=O)NR$_2$, —C(=S)NR$_2$, —NHC(=S)NR$_2$, —(OCH$_2$CH$_2$)$_n$OCH$_3$, and —(OCH$_2$CH$_2$)$_n$OR, wherein R is H, or a linear or branched C$_{1-6}$ alkyl group, and n is an integer between 1 and 100. Additionally, if the terminal functional group of the core is identical to the inner surface functionality, the modification process of the terminal functional group of the core may be omitted.

Regarding the multivalent ligands according to the present invention, any ligand moieties that can bind specifically to the receptors expressed on the surface of tumor cells can be used as the ligand moieties for tumor targeting without any particular limitation. In general, it is well known that each receptor has the corresponding ligand that specifically binds to that particular receptor, and each tumor has the receptor that is overexpressed on the surface of that particular tumor. As such, in order to diagnose a specific tumor, the corresponding ligand moiety which binds specifically to the receptor overexpressed on the surface of that particular tumor can be used.

Regarding the multivalent ligands according to the present invention, the spacer may be a linear biocompatible polymer consisting of either one or a copolymer of two or three selected from the group consisting of polyethylene glycol (PEG), polypropylene oxide, polyester, polyether, polyurethane, polyanhydride, polyethylene, polypropylene, polysiloxane, polysulfone, polyglycolic acid, polylactic acid, polycaprolactone, polyacrylate, polyvinyl alcohol, and polypeptide. Here, any linear biocompatible polymer which can be connected in between the ligand moiety and the terminal functional group of the core by an organic reaction may be used as a spacer without any particular limitation.

Regarding the multivalent ligands according to the present invention, fluorescent dyes, precursors for radiolabeling, and contrast agent moieties for magnetic resonance imaging (MRI) or computed tomography (CT) may be used alone or in combination as the imaging agent by attaching to the terminal functional group of the core. Here, any substance may be used without any particular limitation as long as the fluorescent dyes, precursors for radiolabeling, and contrast agent moieties for magnetic resonance imaging (MRI) or computed tomography (CT) are used in the field of in vivo imaging for tumor diagnosis.

In addition, the purpose of using the precursors for radiolabeling is to use the precursors by radiolabeling in situ prior to in vivo administration for tumor diagnosis because either the half-life of the radioactive material for medical use is too short or the supplementary experiments using cells can be executed in the laboratory without radiolabeling. As such, they do not necessarily have to be in the form of precursors for usage.

The multivalent ligands according to the present invention exhibited high cell survival rates of ca. 80-100% at the concentration of $10^{-10}$, $10^{-9}$, and $10^{-8}$ M and ca. 40-80% at the concentration of $10^{-7}$, $10^{-6}$, and $10^{-5}$ M. Also, multivalent ligands according to the present invention showed relatively high cell survival rates when they were incubated with cells for 24, 48, or 72 h. Thus, the cytotoxicity of multivalent ligands 1a-1j is relatively low (Experimental Example 1 and FIG. 3).

Figure 4:
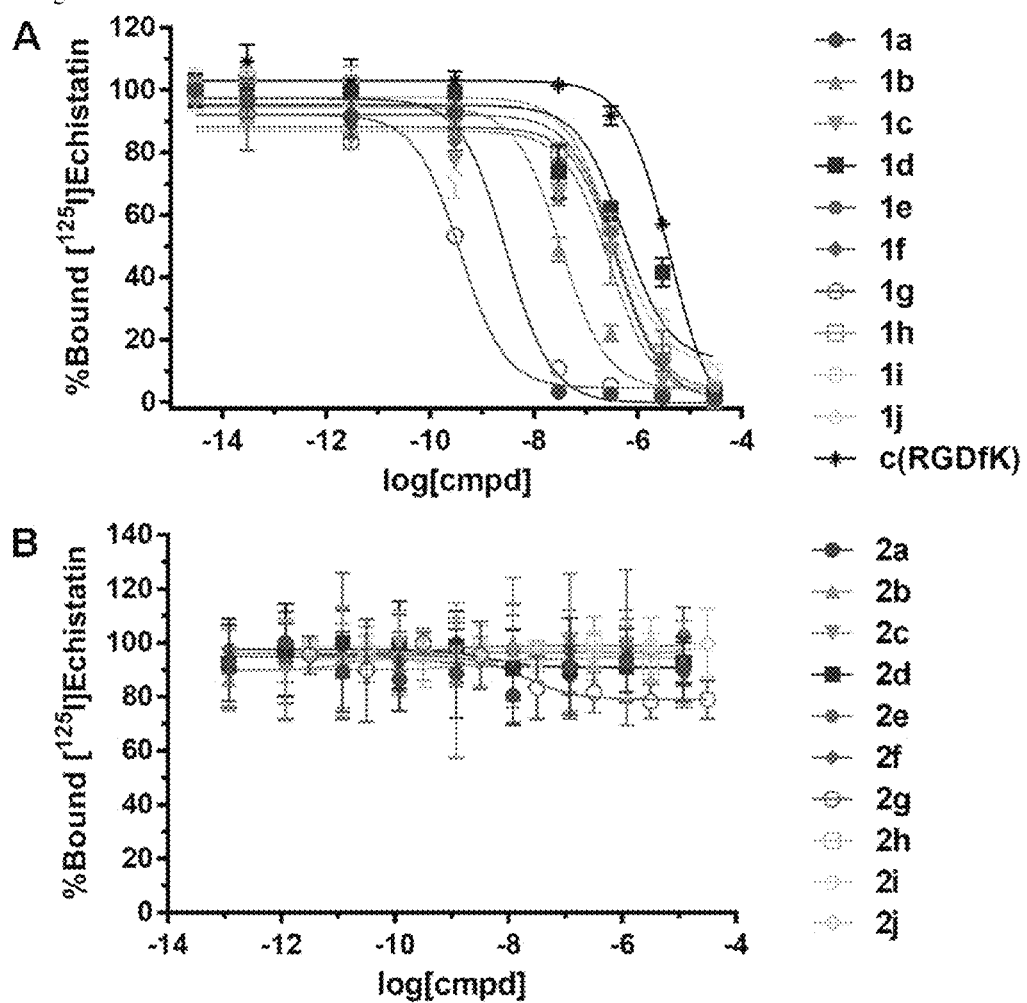
FIG. 4 illustrates (A) a graph showing the concentration-dependent inhibitory effect of the multivalent ligands according to the present invention on binding of [$^{125}$I] echistatin to the $\alpha_v\beta_3$ integrin receptor, and (B) a graph showing the concentration-dependent inhibitory effect of the dendrimer conjugate Compounds 2a-2j without the ligand moieties which are the synthetic precursors of the multivalent ligands mentioned above on binding of [$^{125}$I]echistatin to the $\alpha_v\beta_3$ integrin receptor.

Also, the multivalent ligand according to the present invention had a significantly high avidity of multivalent binding at the $\alpha_v\beta_3$ integrin receptors expressed on the surface of a tumor cell as confirmed by the competitive binding assay with [$^{125}$I]echistatin which is known to bind specifically to the $\alpha_v\beta_3$ integrin receptor (Experimental Example 2 and FIG. 4).

Furthermore, when the SPECT imaging was performed of the tumor-bearing mice which were injected with the dendrimer conjugate Compounds 1a-1j labeled with $^{125}$I, the radiolabeled dendrimer conjugate Compounds 1a-1j existed in various organs including tumor at 2 h post-injection; however, at 24 h post-injection, the radiolabeled dendrimer conjugate Compounds 1a-1j have been eliminated from most of the organs but a substantial amount was noticed specifically where the tumor was implanted.

Therefore, the method according to the present invention has the effect of significantly improving the avidity by regulating the stoichiometric ratio between inner surface functionalities and ligand moieties for tumor targeting by the following: Once a ligand moiety of the multivalent ligand binds to a specific receptor expressed on the surface of a tumor cell, the phenomenon of receptor clustering is initiated whereby the same type of receptors migrate toward the receptor bound to the ligand moiety, making it more favorable for the unassociated ligand moieties to engage in multivalent binding. Furthermore, the appropriately selected inner surface functionality which has been then positioned in closer proximity to the cell surface by the bound ligand moieties can interact attractively with the surface of a tumor cell to promote the additional binding of unassociated ligand moieties to the clustered receptors.

Herein below, the present invention will be explained in detail with reference to the Examples below. However, the present invention is not limited to any specific examples provided below, since the examples are provided for the illustrative purpose only.

Preparational Example 1

Preparation of Azido-PEG Carbonate (5)

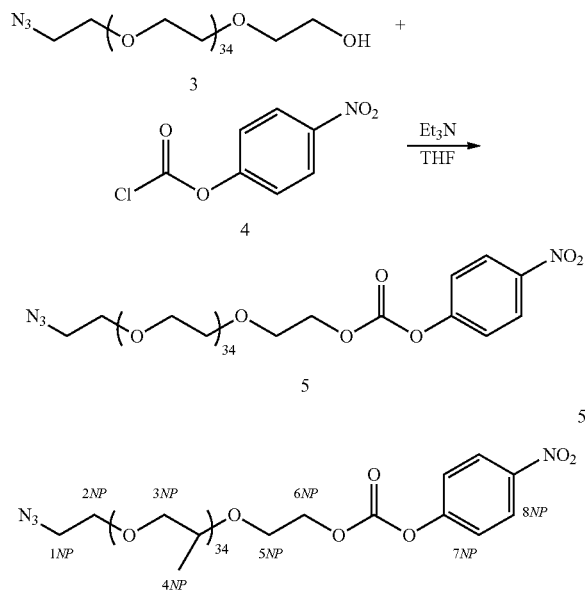

Azido-dPEG$_{36}$-alcohol (Compound 3, purchased from Quanta BioDesign, MW 1628.92; 935 mg, 0.574 mmol) and 4-nitrophenyl chloroformate (Compound 4, 233 mg, 1.15 mmol) was dissolved in tetrahydrofuran (THF, 57 mL), to which triethylamine (0.16 mL, 1.15 mmol) was added slowly. The reaction mixture was stirred at room temperature for 41 h under a dry argon (Ar) atmosphere. After removal of the solvent under reduced pressure, the crude mixture was loaded on a size-exclusion chromatography (SEC) column (model: Bio-Beads S-X1, H 41 cm×O.D. 4.5 cm, manufacturer: Bio-Rad) in N,N-dimethylformamide (DMF) for purification. The yellowish SEC fractions containing the target product as confirmed by the analysis of $^1$H NMR spectra were combined to give 914 mg (0.243 mmol, 42 mol % purity) of Compound 5.

$^1$H NMR (600 MHz, CDCl$_3$) δ 8.20 (d, 2H, J=12 Hz, H$_{8NP}$), 7.32 (d, 2H, J=11 Hz, H$_{7NP}$), 4.38-4.34 (m, 2H, H$_{6NP}$), 3.72-3.68 (m, 2H, H$_{2NP}$), 3.68-3.40 (m, 358H, H$_{3NP}$, H$_{4NP}$, and H$_{5NP}$), 3.30 (t, 4.45H, J=6.3, H$_{1NP}$);

HRMS (ESI) Calcd for C$_{79}$H$_{148}$N$_4$O$_{40}$Na (M+Na)$^+$: 1815.9568, Found: 1818.9537.

Preparational Example 2

Preparation of DBCO-c(RGDfK) Conjugate (17)

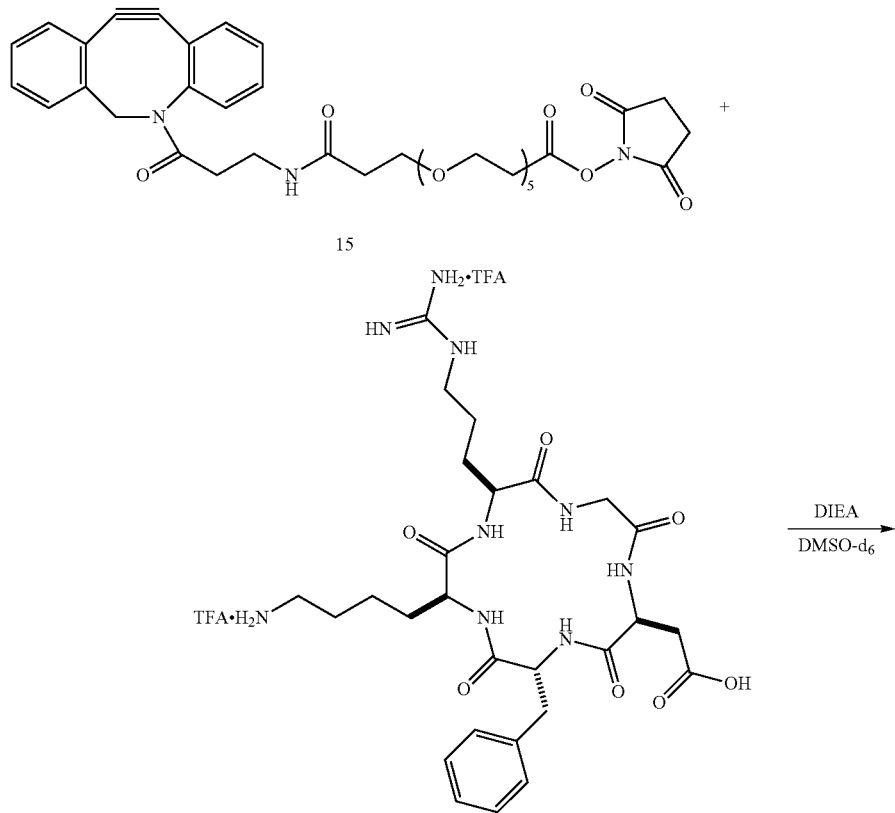

-continued

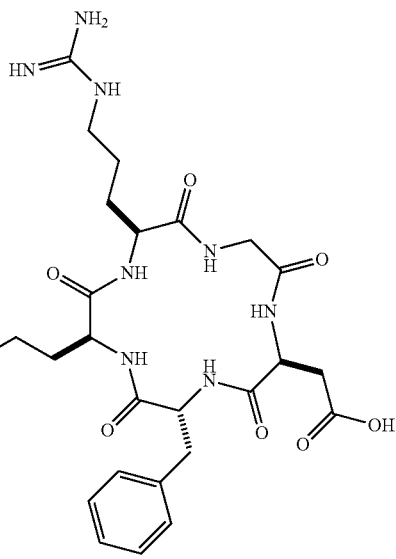

17

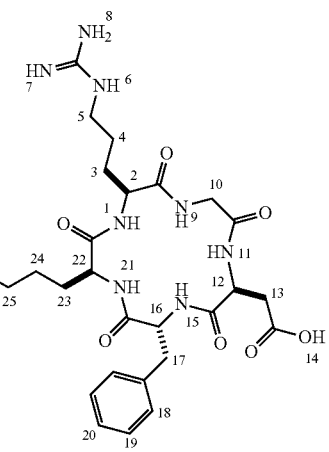

17

To a solution of DBCO-PEG4-N-hydroxy succinimidyl (NHS) ester (Compound 15, purchased from Click Chemistry Tools, 117 mg, 0.178 mmol) and c(RGDfK)·2TFA (Compound 16, purchased from FutureChem, 142 mg, 0.174 mmol) in DMSO-$d_6$ (1.6 mL) was slowly added N,N-diisopropylethylamine (DIEA, 91 µL, 0.522 mmol). The reaction mixture was stirred at room temperature for 5 h under a dry Ar atmosphere and concentrated under reduced pressure. The crude mixture was chromatographed on a silica gel column (70:30:6 $CH_2Cl_2$/MeOH/$H_2O$) to give 138 mg (117 µmol, 68%) of Compound 17.

$R_f$: 0.45 [silica gel, 70:30:6 $CH_2Cl_2$/MeOH/$H_2O$];

$^1$H NMR (600 MHz, DMSO-$d_6$) δ 8.54-8.43 (m, 1H, $H_1$), 8.32-8.13 (m, 3H, $H_6$, $H_{11}$, and $H_{21}$), 7.88 (m, 1H, $H_{27}$), 7.77-7.56 (m, 2H, $H_{15}$ and $H_{12'}$), 7.63 (d, 1H, J=8.4 Hz, $H_{8'}$), 7.48-7.43 (m, 1H, $H_{1'}$), 7.52-7.48 (m, 1H, $H_{3'}$), 7.48-7.43 (m, 2H, $H_{2'}$ and $H_{4'}$), 7.42-7.37 (m, 1H, $H_{7'}$), 7.35 (t, 1H, J=8.1 Hz, $H_{6'}$), 7.32-7.28 (m, 1H, $H_{5'}$), 7.25-7.12 (m, 5H, $H_{18}$, $H_{19}$, and $H_{20}$), 5.04 (d, 1H, J=15 Hz, $H_{9'}$), 4.70-4.60 (m, 1H, $H_{16}$), 4.59-4.47 (m, 1H, $H_2$), 4.43-4.27 (m, 1H, $H_{22}$), 4.25-4.07 (m, 2H, $H_{10}$ and $H_{12}$), 3.63 (d, 1H, J=15 Hz, $H_{9'}$), 3.58 (t, 2H, J=7.6 Hz, $H_{23'}$), 3.55-3.33 (m, 19H, $H_{14'}$, $H_{15'}$, $H_{16'}$, $H_{17'}$, $H_{18'}$, $H_{19'}$, $H_{20'}$, $H_{21'}$, $H_{22'}$, and $H_{17}$), 3.16-3.06 (m, 2H, $H_5$), 3.04-2.89 (m, 3H, $H_{26}$ and $H_{11'}$), 2.75 (d, 1H, J=17 Hz, $H_{13}$), 2.64-2.61 (m, 1H, $H_{17}$), 2.46-2.40 (m, 1H, $H_{10'}$), 2.30 (t, 2H, J=7.3 Hz, $H_{24'}$), 2.17 (t, 2H, J=7.0 Hz, $H_{13'}$), 2.12-1.94 (m, 1H, $H_{13}$), 1.74-1.78 (m, 1H, $H_{10'}$), 1.75-1.41 (m, 6H, $H_3$, $H_4$, and $H_{23}$), 1.42-1.31 (m, 1H, $H_{25}$), 1.29-1.12 (m, 1H, $H_{24}$);

HRMS (ESI) Calcd for $C_{59}H_{80}N_{11}O_{15}$ (M+H)$^+$: 1182.5835, Found: 1182.5829.

Example 1

Preparation of Dendrimer Conjugate (1a)

Step 1: Partial Derivatization of the Core with Azido-PEG Units [Preparation of Dendrimer Conjugate (7)]

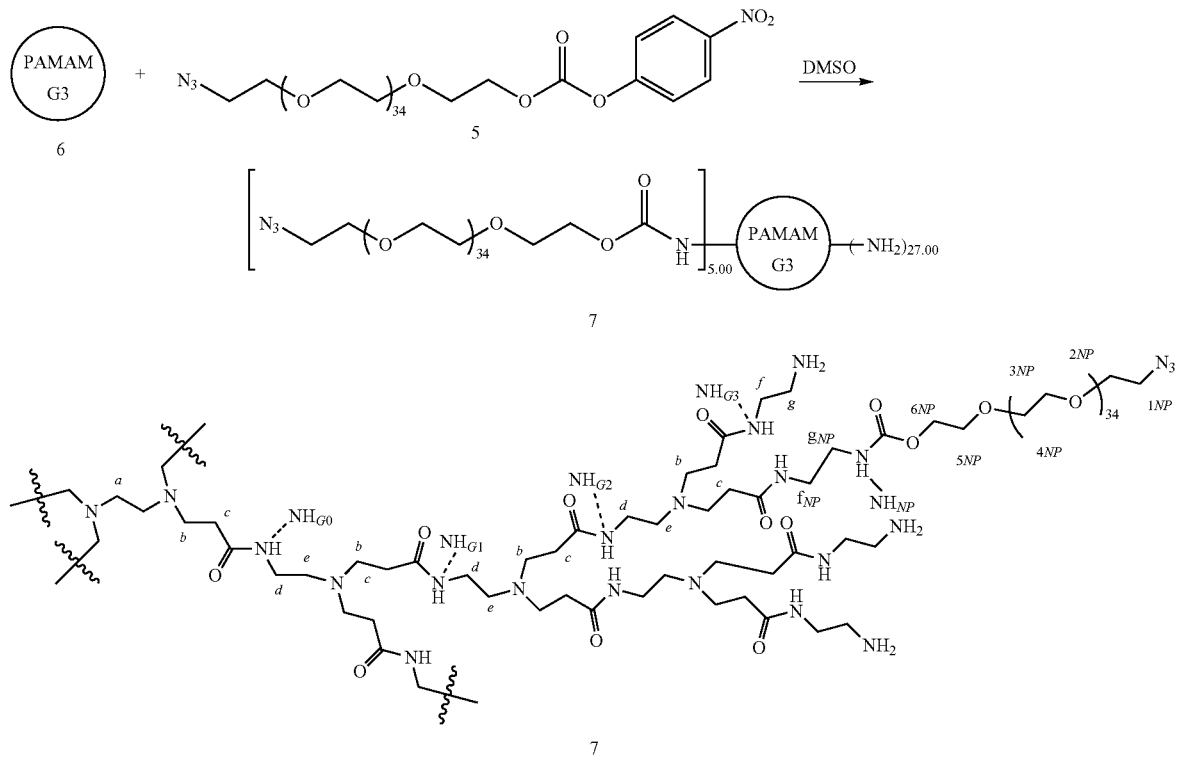

The methanolic solution of amine-terminated third generation (G3) polyamidoamine (PAMAM) dendrimer with ethylenediamine core (Compound 6, purchased from Dendritech) was dried in vacuo for 6 h and the resulting solid was weighed (266 mg, 38.6 μmol). The anhydrous dimethyl sulfoxide (DMSO, 20 mL) was added to this dried Compound 6 to dissolve completely, and then to this stirred solution was slowly added a solution of Compound 5 (42 mol % purity, 869 mg, 0.231 mmol) obtained in Preparational Example 1 in DMSO (5.7 mL). The reaction was stirred at room temperature for 33 h under a dry Ar atmosphere. Next, the reaction mixture was dialyzed (model: Spectra/Por Regenerated Cellulose (RC) membrane, MWCO 3500, manufacturer: Spectrum Laboratories) against methanol (×2, for 2 h each) with stirring to remove DMSO and small molecular reagents such as Compound 5. After removal of the solvent under reduced pressure, the crude mixture was loaded on a SEC column (model: Bio-Beads S-X1, H 41 cm×O.D. 4.5 cm, manufacturer: Bio-Rad) in DMF to isolate the target Compound 7. The yellowish SEC fractions were combined, concentrated under reduced pressure, and dried in vacuo to give 516 mg of Compound 7.

$^1$H NMR (600 MHz, DMSO-$d_6$) δ 7.22 (br s, 5.00H, NH$_{NP}$ of major isomer), 6.81 (br s, 0.43H, NH$_{NP}$ of minor isomer), 4.04 (t, 10.89H, J=4.2 Hz, H$_{6NP}$), 3.63-3.37 (m, 797.48H, H$_{1NP}$, H$_{2NP}$, H$_{3NP}$, H$_{4NP}$, and H$_{5NP}$), 3.16-2.95 (m, 152.23H, H$_d$, H$_f$, H$_{fNP}$, and H$_{gNP}$), 2.70-2.54 (m, 163.40H, H$_b$ and H$_g$), 2.43 (m, 61.11H, H$_e$ and H$_a$), 2.20 (m, 120.00H, H$_c$).

Step 2: Partial Derivatization of the Core with Fluorophore and Precursor for Radiolabeling [Preparation of Dendrimer Conjugate (2a)]

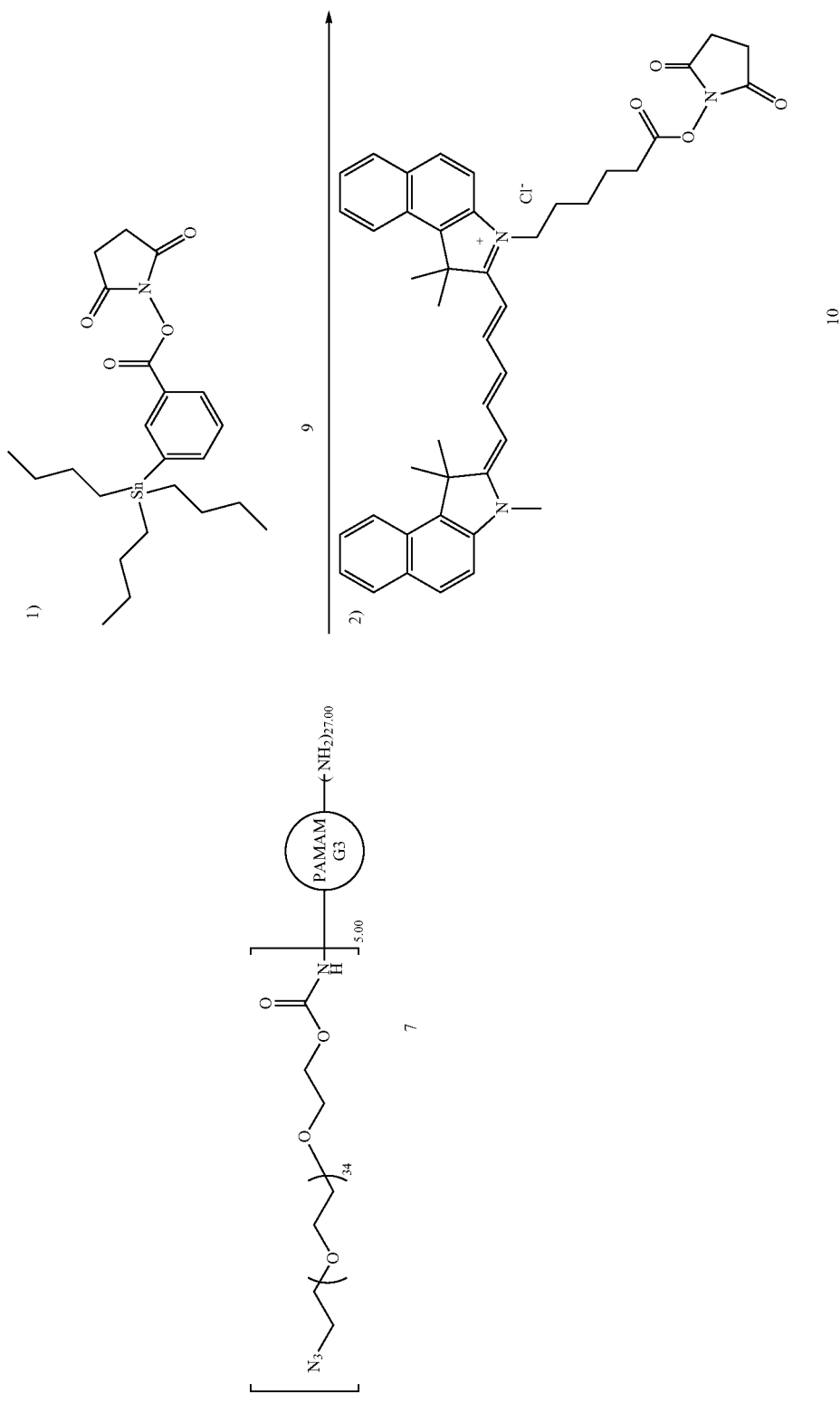

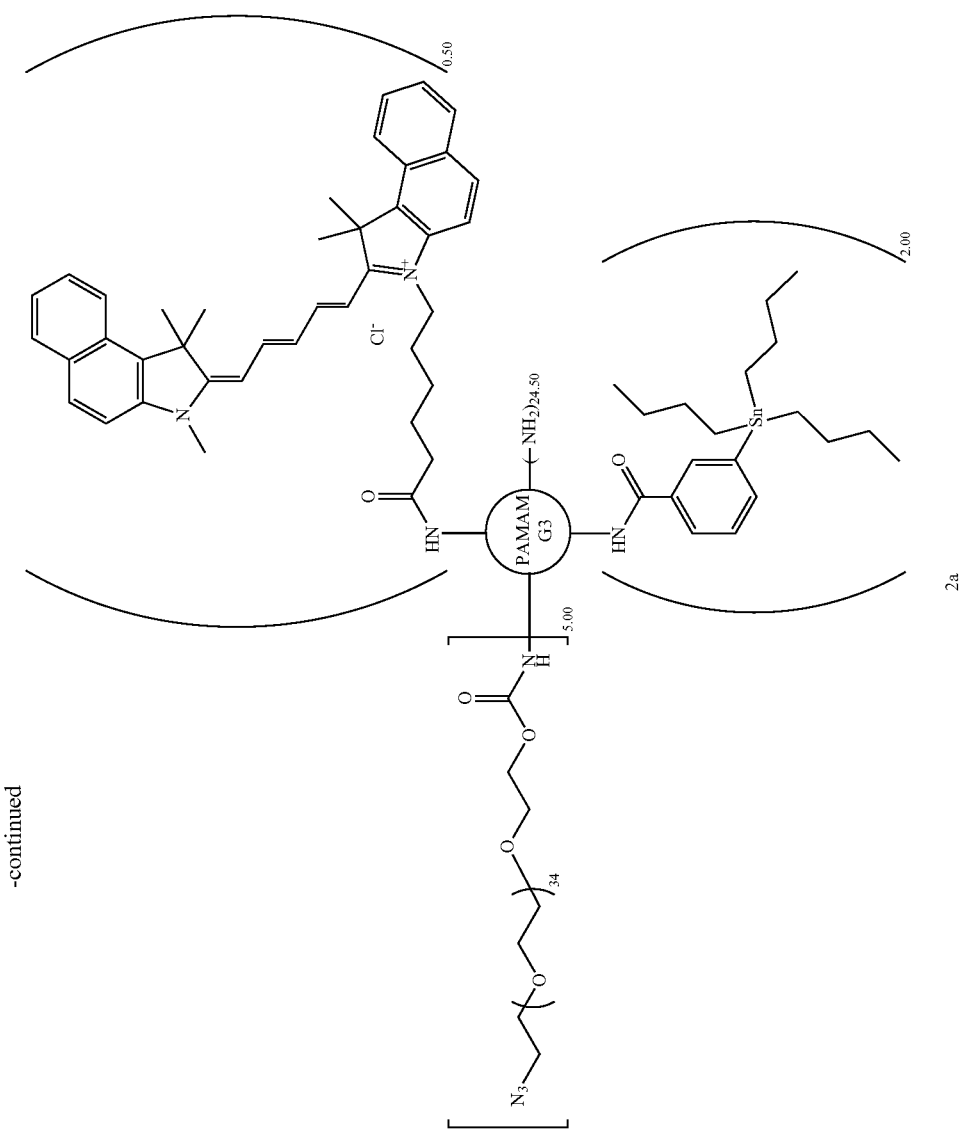

-continued
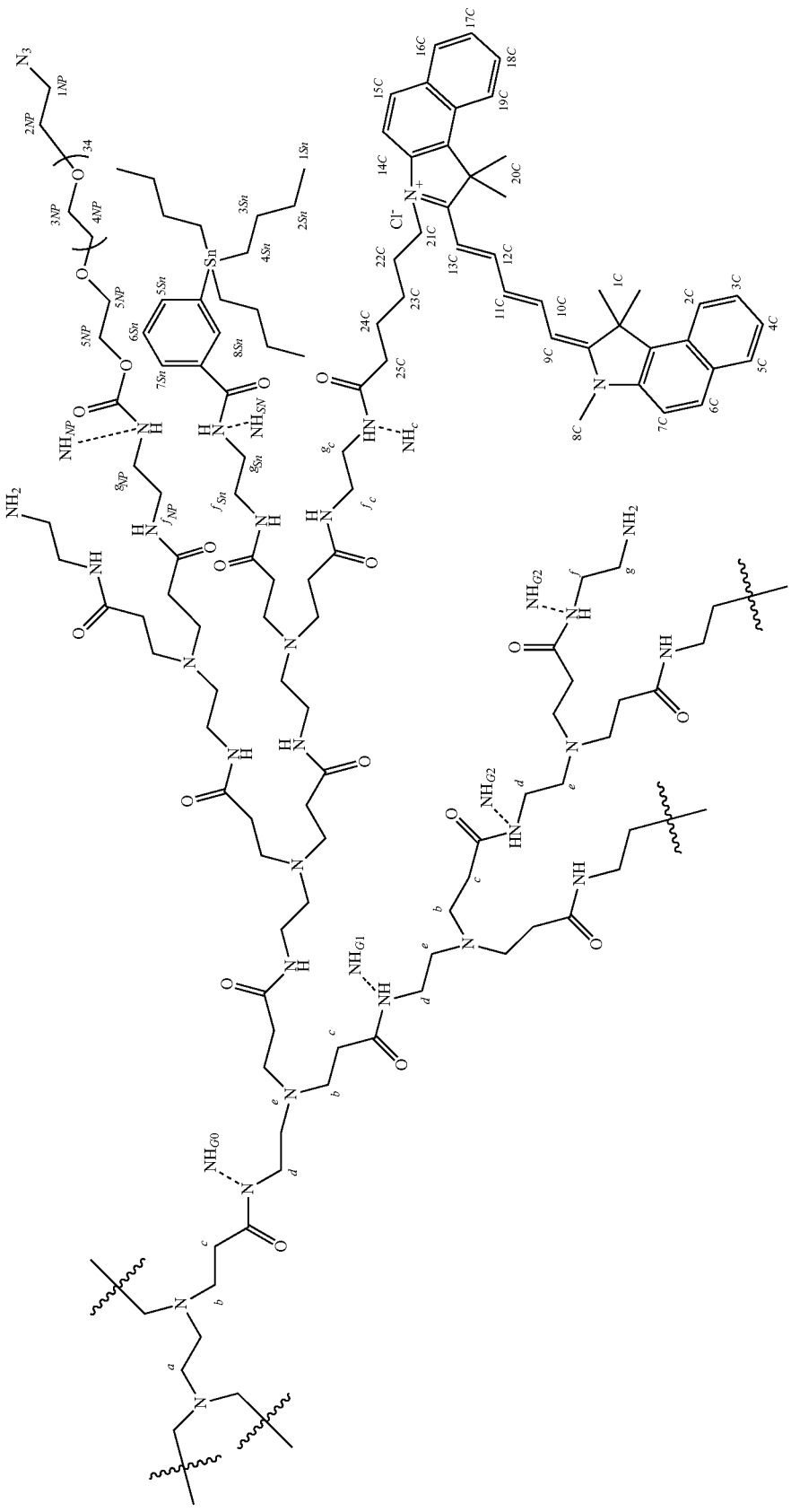

Compound 7 (220 mg, 14.7 μmol) obtained in Step 1 was dissolved completely in DMSO (8.0 mL) with vigorous sonication. To this stirred solution was added DIEA (10.0 μL, 58.7 μmol) followed by a solution of 3-(tri-n-butylstannyl)benzoyl NHS ester (Compound 9, purchased from Texas Biochemicals, 16.3 mg, 30.9 μmol) in DMSO (1.8 mL) dropwise over a 4-min period. The reaction was stirred at room temperature for 24 h under a dry Ar atmosphere. Subsequently, to this stirred solution was slowly added a solution of Cy5.5 NHS ester (Compound 10, purchased from Lumiprobe, 95% purity, 5.53 mg, 7.72 μmol) in DMSO-$d_6$ (400 μL). The reaction was protected from light and stirred at room temperature for 65 h. The crude mixture of Compound 2a was divided into six equal portions by volume and five of them were saved for surface modification reactions. One of six divided portions containing Compound 2a (1.70 mL, ca. 2.45 μmol) was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 37.5 cm×O.D. 3 cm, manufacturer: Bio-Rad) in DMF. The SEC fractions containing the product were combined, concentrated under reduced pressure, and dried extensively in vacuo to give 44.8 mg of Compound 2a.

$^1$H NMR (600 MHz, DMSO-$d_6$) δ 4.03 (m, 9.99H, $H_{6NP}$), 3.64-3.38 (m, 751.31H, $H_{1NP}$, $H_{2NP}$, $H_{3NP}$, $H_{4NP}$, and $H_{5NP}$), 3.17-2.96 (m, 139.79H, $H_d$, $H_f$, $H_{fNP}$, $H_{gNP}$, $H_{fSn}$, and $H_{gSn}$), 2.73-2.53 (m, 138.85H, $H_b$ and $H_g$), 2.43 (m, 64.12H, $H_e$ and $H_a$), 2.19 (m, 121.94H, $H_c$), 1.51 (m, 16.06H, $H_{4Sn}$), 1.28 (m, 15.95H, $H_{3Sn}$), 1.06 (m, 12.60H, $H_{2Sn}$), 0.84 (t, 18.00H, J=6.7 Hz, $H_{1Sn}$).

Step 3: Attachment of Ligand Moieties to the Azide End of PEG by Click Reaction [Preparation of Dendrimer Conjugate (1a)]

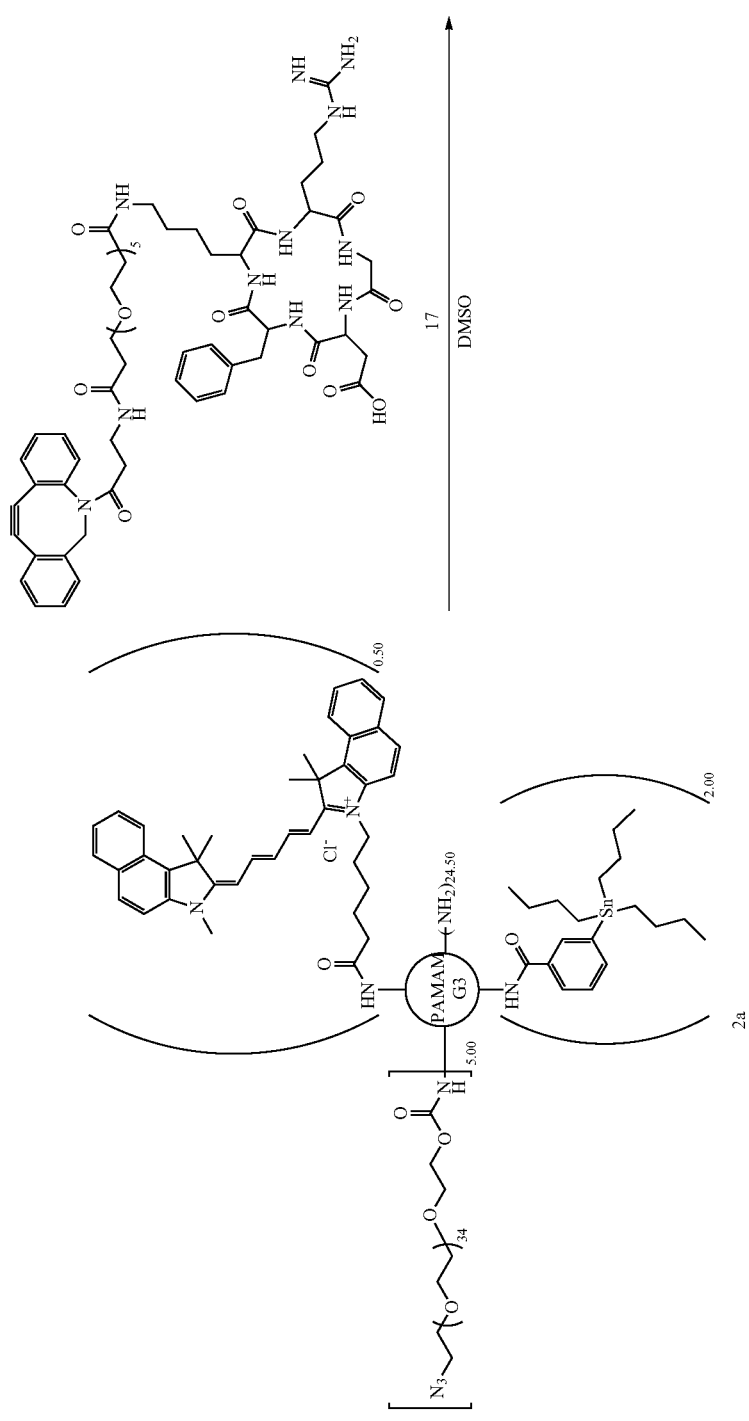

-continued
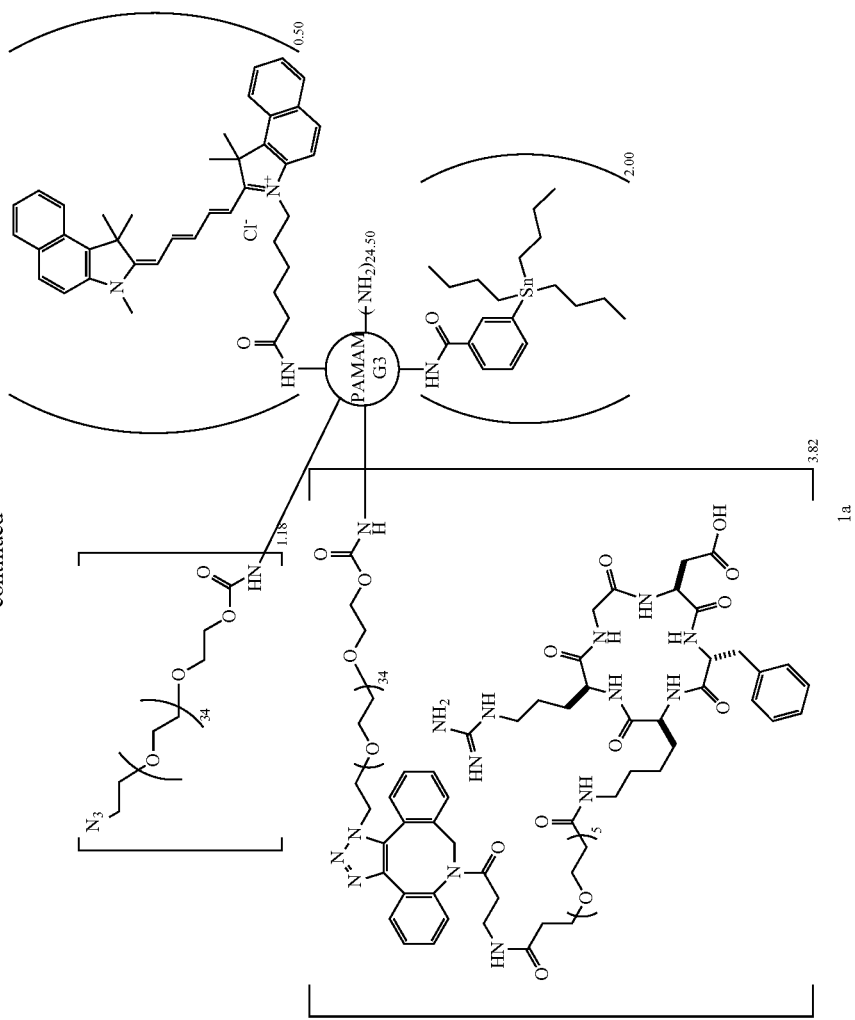

-continued
1a
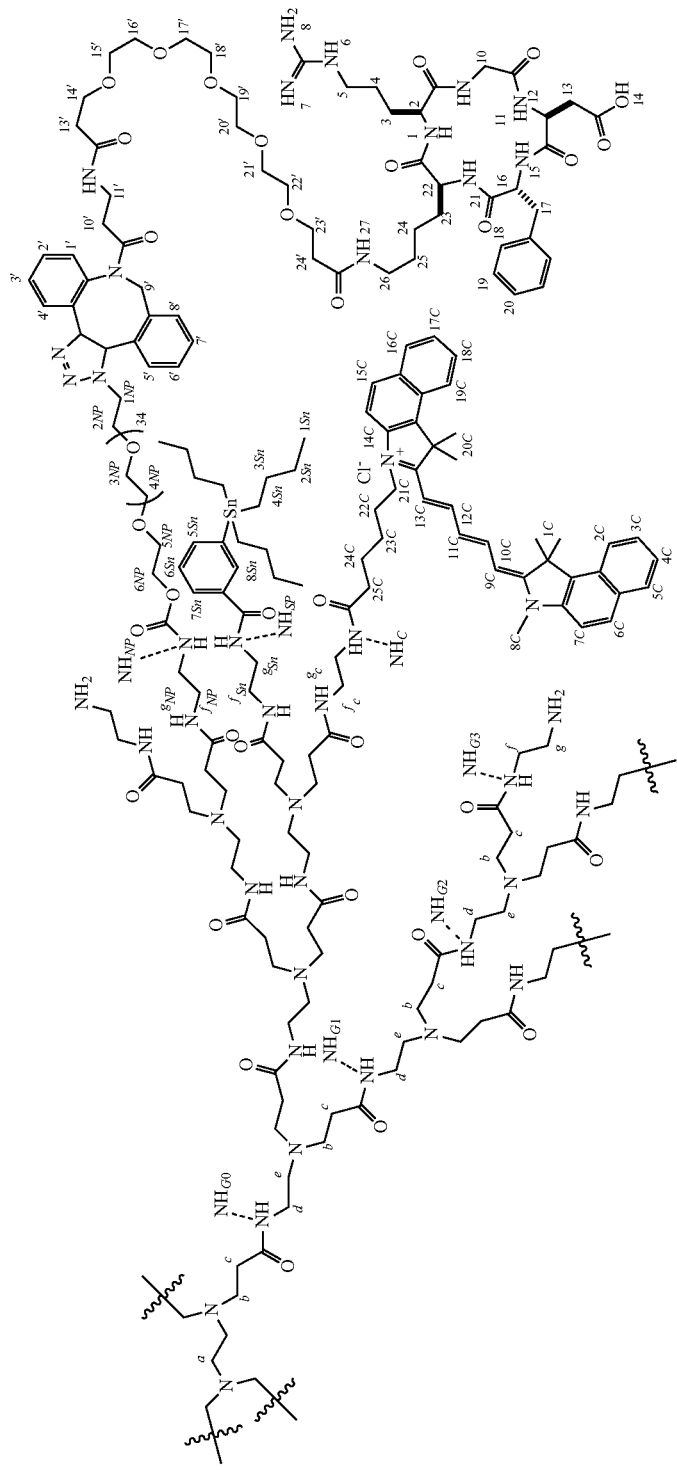

To a solution of Compound 2a (35.3 mg, 2.05 μmol) obtained in Step 2 in DMSO-$d_6$ (1.24 mL) was added a solution of Compound 17 (21.2 mg, 17.9 μmol) obtained in Preparational Example 2 in DMS-$d_6$ (160 μL). The reaction was protected from light and stirred at room temperature for 24 h. In a dark room, the crude mixture was purified by a preparative SEC (model: Bio-Beads S-X1, H 39.5 cm×O.D. 3 cm, manufacturer: Bio-Rad) in DMF. The SEC fractions containing the product were combined and dried extensively in vacuo to give Compound 1a' (structure not shown). Unfortunately, the analysis of Compound 1a' by $^1$H NMR in DMSO-$d_6$ indicated only ca. 3.47 RGD moieties were attached out of ca. five available azide groups of Compound 2a. In an attempt to bring the RGD attachment to completion, another round of click reaction was pursued by dissolving Compound 17 (14.8 mg, 12.48 μmol) obtained in Preparational Example 2 and Compound 1a' (ca. 2.05 μmol) in DMSO-$d_6$ (1.4 mL). The reaction was protected from light and stirred at room temperature for 24 h under a dry Ar atmosphere. In a dark room, the crude mixture was purified by SEC using three different columns consecutively: Bio-Beads S-X1 (H 31 cm×O.D. 3 cm, manufacturer: Bio-Rad) in DMF, Sephadex LH-20 (H 37 cm×O.D. 3 cm) in methanol, and Sephadex G-25 (H 37 cm×O.D. 4.5 cm) in deionized water. The SEC fractions containing the product were combined, concentrated under reduced pressure, and dried extensively in vacuo to give 16.5 mg of Compound 1a.

$^1$H NMR (600 MHz, DMSO-$d_6$) δ 5.90, 4.48 (ABq, 3.82H, $H_{9'}$), 5.84, 4.45 (ABq, 3.82H, $H_{9'}$), 0.84 (m, 18.00H, J=6.4 Hz, $H_{1Sn}$);

MS (MALDI-TOF, DHB matrix) $M_n$ 24322.86, $M_w$ 24763.67, PDI 1.02.

Example 2

Preparation of Dendrimer Conjugate (1b)

Step 1: Partial Modification of the Residual Surface Groups [Preparation of Dendrimer Conjugate (2b)]

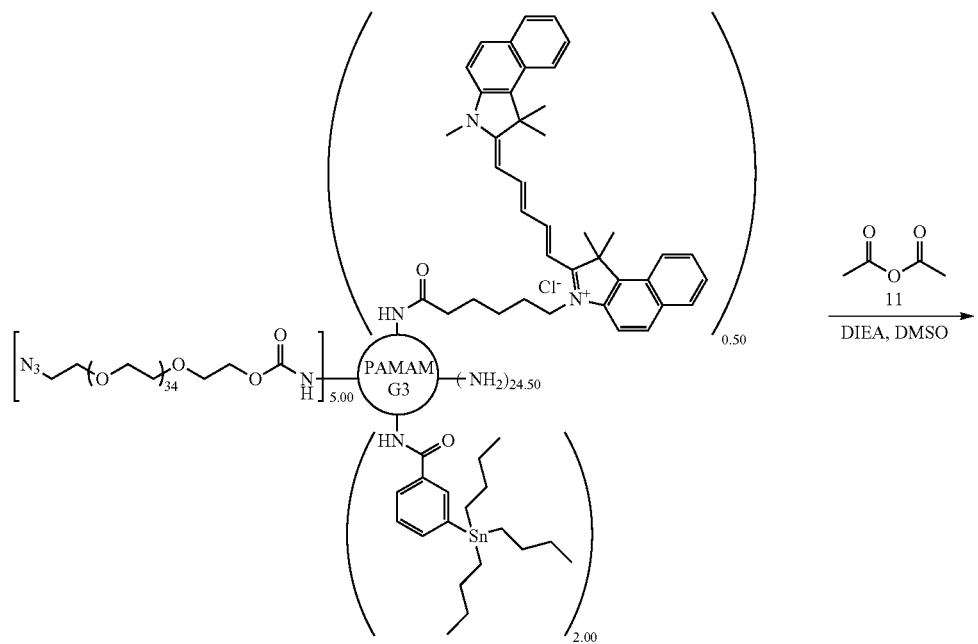

2a

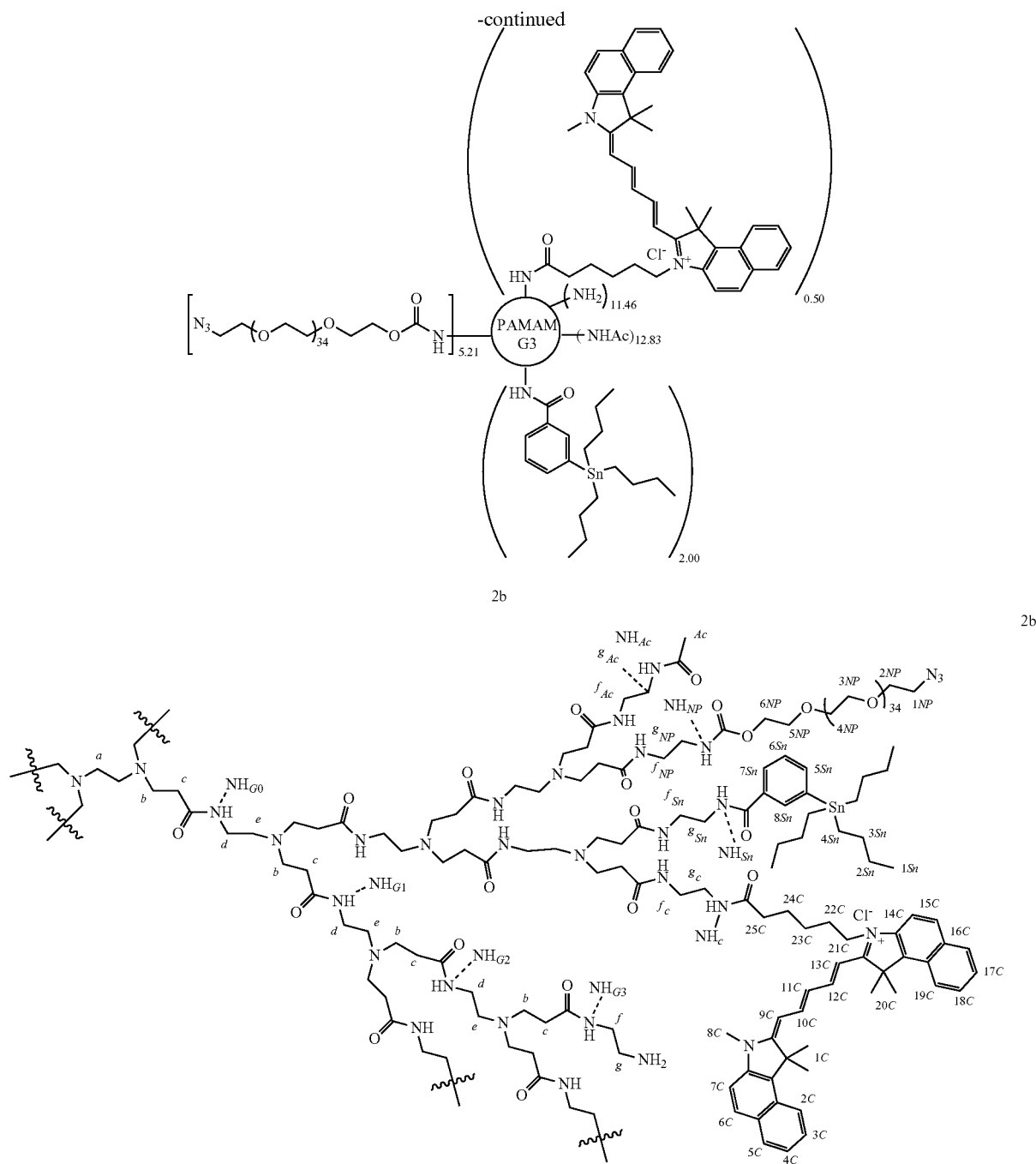

To a portion of the crude reaction mixture of Compound 2a (1.70 mL, ca. 2.45 μmol) obtained in Step 2 of Example 1 was added DIEA (9.0 μL, 48.9 μmol) followed by a 0.106 M solution of acetic anhydride (Ac$_2$O, Compound 11) in DMSO-d$_6$ (230 μL, 24.5 μmol) slowly. The reaction was protected from light and stirred at room temperature for 12 h under a dry Ar atmosphere. In a dark room, the crude mixture was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 37.5 cm×O.D. 3 cm, manufacturer: Bio-Rad) in DMF. The SEC fractions containing the product were combined, concentrated under reduced pressure, and dried extensively in vacuo to give 35.3 mg of Compound 2b.

$^1$H NMR (600 MHz, DMSO-d$_6$) δ 4.04 (m, 10.41H, H$_{6NP}$), 3.64-3.37 (m, 764.35H, H$_{1NP}$, H$_{2NP}$, H$_{3NP}$, H$_{4NP}$, and H$_{5NP}$), 3.19-2.89 (m, 165.52H, H$_d$, H$_f$, H$_{fNP}$, H$_{gNP}$, H$_{fSn}$, H$_{gSn}$, H$_{fAc}$ and H$_{gAc}$), 2.83-2.53 (m, 129.11H, H$_b$ and H$_e$), 2.42 (m, 60.33H, H$_e$ and H$_a$), 2.19 (m, 122.92H, H$_c$), 1.80 (s, 38.44H, H$_{Ac}$), 1.51 (m, 14.52H, H$_{4Sn}$), 1.28 (m, 14.71H, H$_{3Sn}$), 1.06 (m, 12.35H, H$_{2Sn}$), 0.84 (t, 18.00H, J=6.4 Hz, H$_{1Sn}$).

Step 2: Attachment of Ligand Moieties to the Azide End of PEG by Click Reaction [Preparation of Dendrimer Conjugate (1b)]

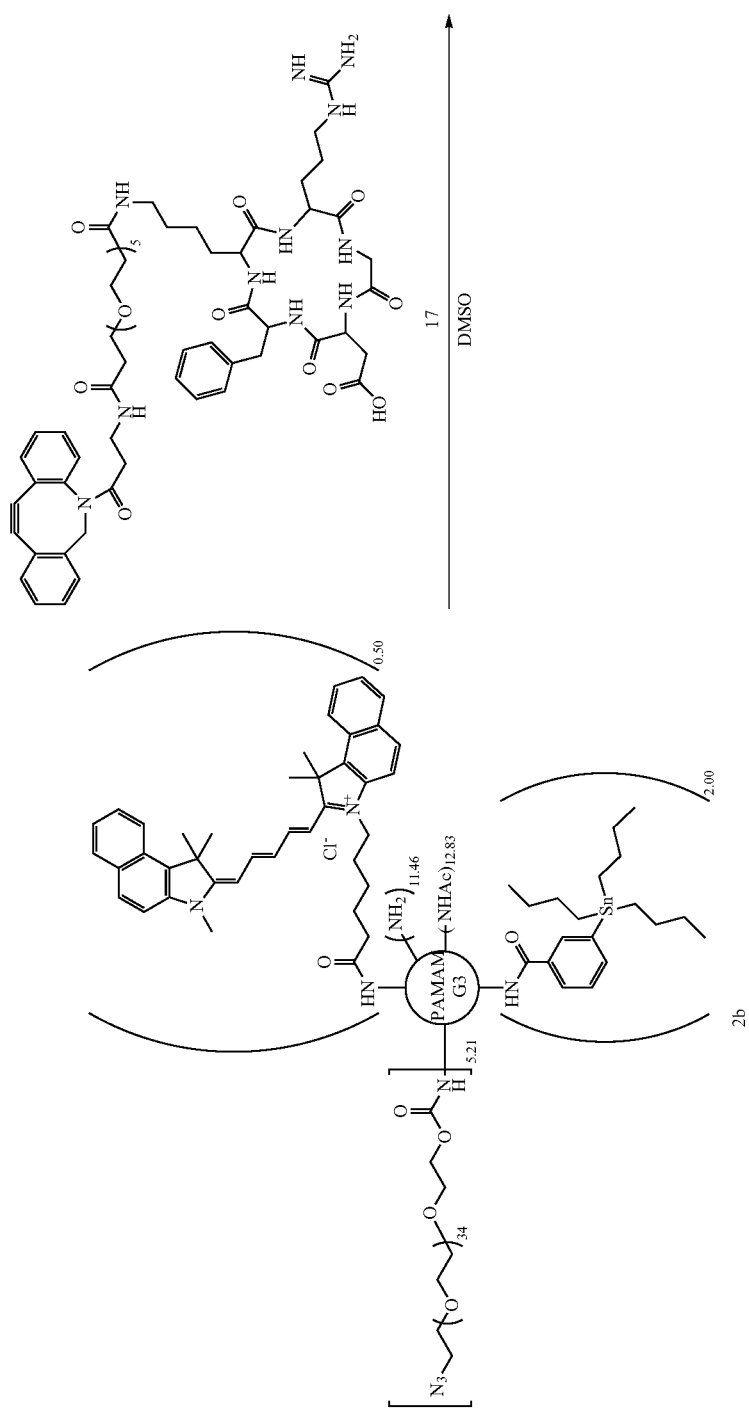

-continued
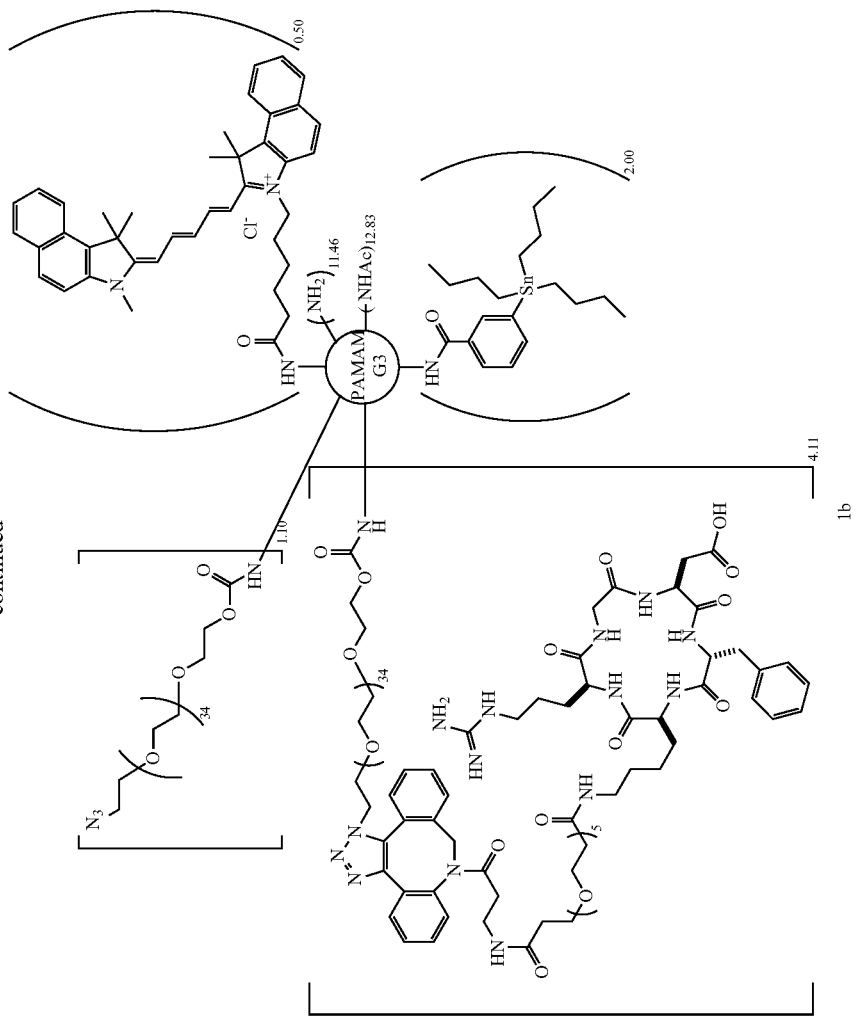

-continued
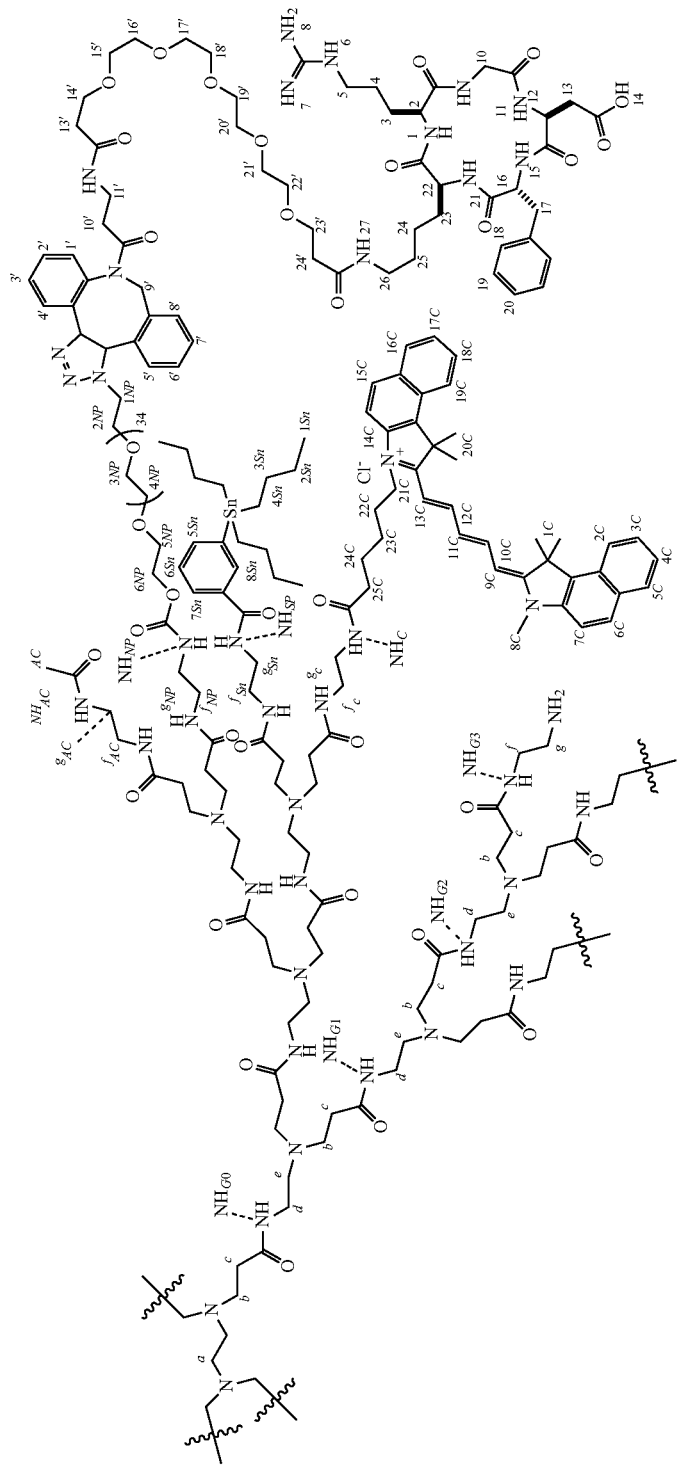

To a solution of Compound 2b (31.2 mg, 1.77 μmol) obtained in Step 1 in DMSO-$d_6$ (1.07 mL) was added a solution of Compound 17 (17.7 mg, 15.0 μmol) obtained in Preparational Example 2 in DMSO-$d_6$ (130 μL). The reaction was protected from light and stirred at room temperature for 24 h. In a dark room, the crude mixture was purified by a preparative SEC (model: Bio-Beads S-X1, H 36 cm×O.D. 3 cm, manufacturer: Bio-Rad) in DMF. The SEC fractions containing the product were combined and dried extensively in vacuo to give Compound 1b' (structure not shown). Unfortunately, the analysis of Compound 1b' by $^1$H NMR in DMSO-$d_6$ indicated only ca. 3.42 RGD moieties were attached out of ca. five available azide groups of Compound 2b. In an attempt to bring the RGD attachment to completion, another round of click reaction was pursued by adding a solution of Compound 17 (7.23 mg, 6.12 μmol) obtained in Preparational Example 2 in DMSO-$d_6$ (250 μL) to the solution of Compound 1b' (ca. 1.77 μmol) in DMSO-$d_6$ (950 μL). The reaction was protected from light and stirred at room temperature for 24 h under a dry Ar atmosphere. In a dark room, the crude mixture was purified by SEC twice: Bio-Beads S-X1 (H 32.5 cm×O.D. 3 cm, manufacturer: Bio-Rad) in DMF and Sephadex LH-20 (H 37.5 cm×O.D. 3 cm) in methanol. The SEC fractions containing the product were combined, concentrated under reduced pressure, and dried extensively in vacuo to give 31.7 mg of Compound 1b.

$^1$H NMR (600 MHz, DMSO-$d_6$) δ 5.90, 4.48 (ABq, 4.11H, $H_{9'}$), 5.84, 4.45 (ABq, 4.11H, $H_{9'}$), 0.84 (m, 18.00H, J=5.6 Hz, $H_{1Sn}$);

MS (MALDI-TOF, DHB matrix) $M_n$ 21054.77, $M_w$ 21943.62, PDI 1.04.

Example 3

Preparation of Dendrimer Conjugate (1c)

Step 1: Modification of the Residual Surface Groups [Preparation of Dendrimer Conjugate (2c)]

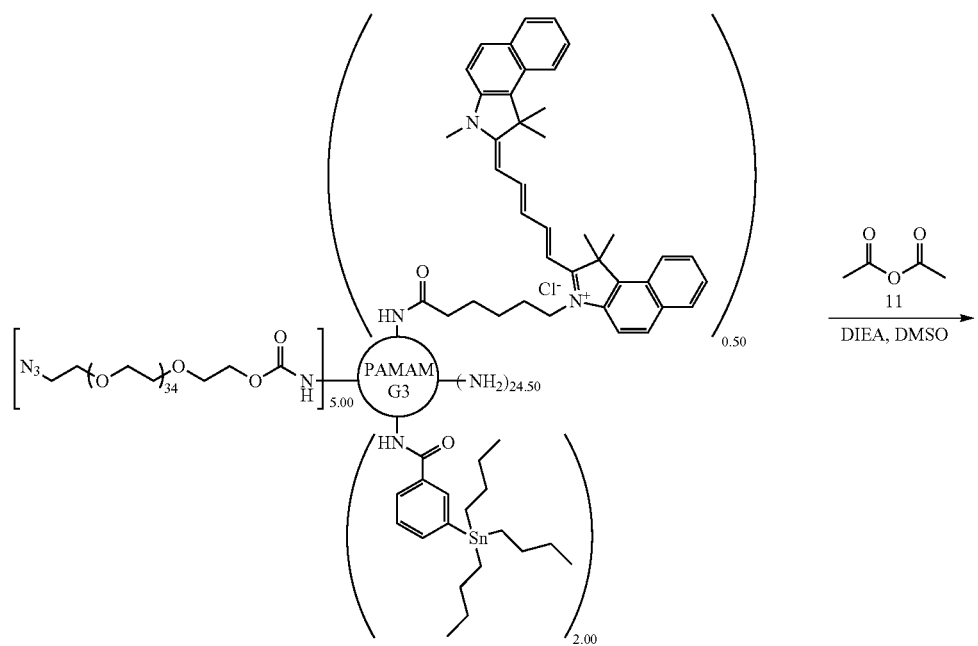

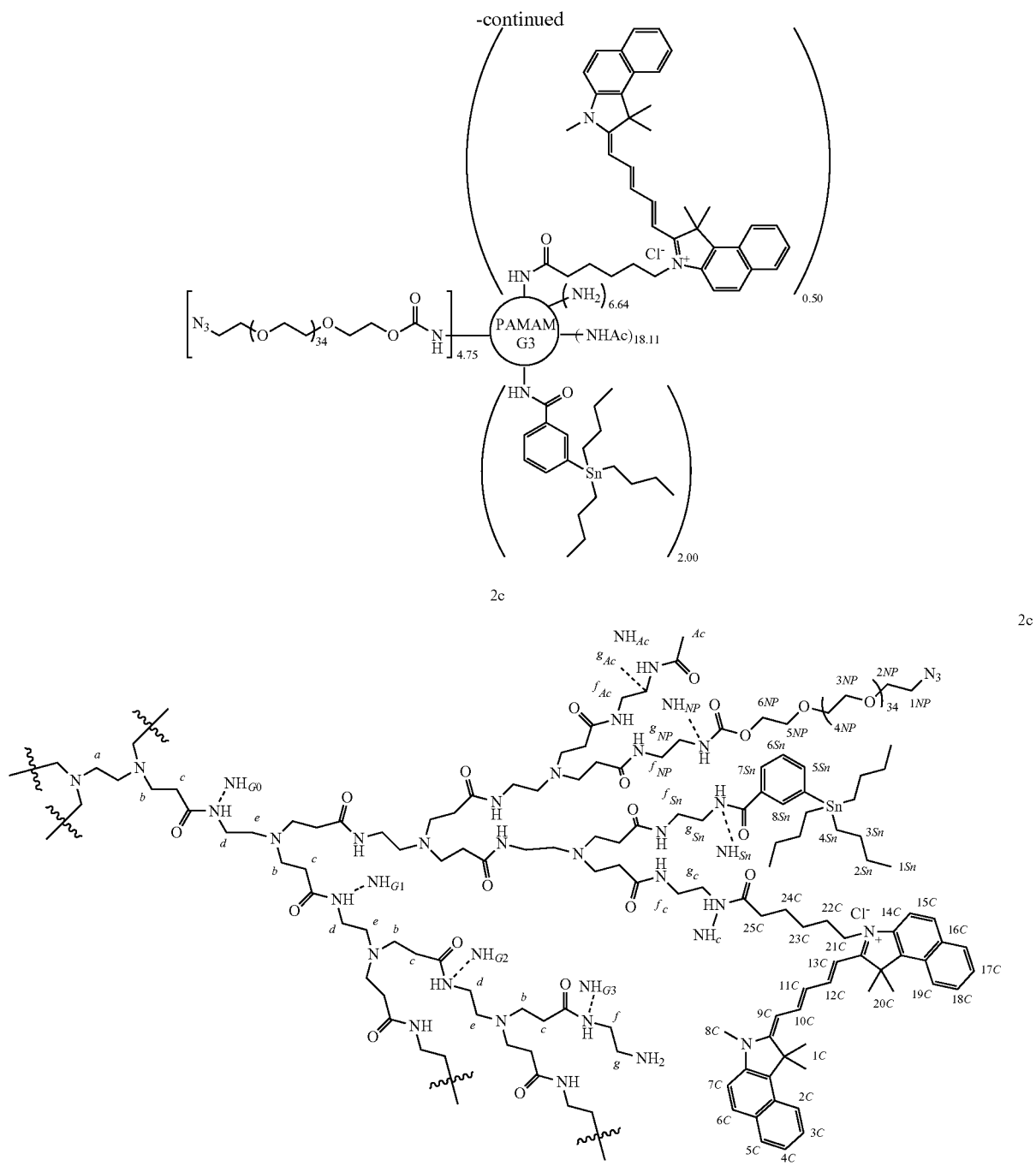

To a portion of the crude reaction mixture of Compound 2a (1.70 mL, ca. 2.45 μmol) obtained in Step 2 of Example 1 were added DIEA (21.0 μL, 122 μmol) and Ac$_2$O (Compound 11, 17 μL, 183 μmol) followed by DMSO-d$_6$ (200 μL). The reaction was protected from light and stirred at room temperature for 12 h under a dry Ar atmosphere. In a dark room, the crude mixture was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 35.5 cm×O.D. 3 cm, manufacturer: Bio-Rad) in DMF. The SEC fractions containing the product were combined, concentrated under reduced pressure, and dried extensively in vacuo to give 35.2 mg of Compound 2c.

$^1$H NMR (600 MHz, DMSO-d$_6$) δ 4.03 (m, 9.49H, H$_{6NP}$), 3.94-3.37 (m, 709.90H, H$_{1NP}$, H$_{2NP}$, H$_{3NP}$, H$_{4NP}$, and H$_{5NP}$), 3.26-2.92 (m, 171.65H, H$_d$, H$_f$, H$_{fNP}$, H$_{gNP}$, H$_{fSn}$, H$_{gSn}$, H$_{fAc}$, and H$_{gAc}$), 2.82-2.55 (m, 116.60H, H$_b$ and H$_g$), 2.42 (m, 56.76H, H$_e$ and H$_a$), 2.18 (m, 116.84H, H$_c$), 1.80 (s, 54.20H, H$_{Ac}$), 1.52 (m, 14.24H, H$_{4Sn}$), 1.28 (m, 17.04H, H$_{3Sn}$), 1.06 (m, 11.88H, H$_{2Sn}$), 0.84 (t, 18.00H, J=6.4 Hz, H$_{1Sn}$).

Step 2: Attachment of Ligand Moieties to the Azide End of PEG by Click Reaction [Preparation of Dendrimer Conjugate (1c)]

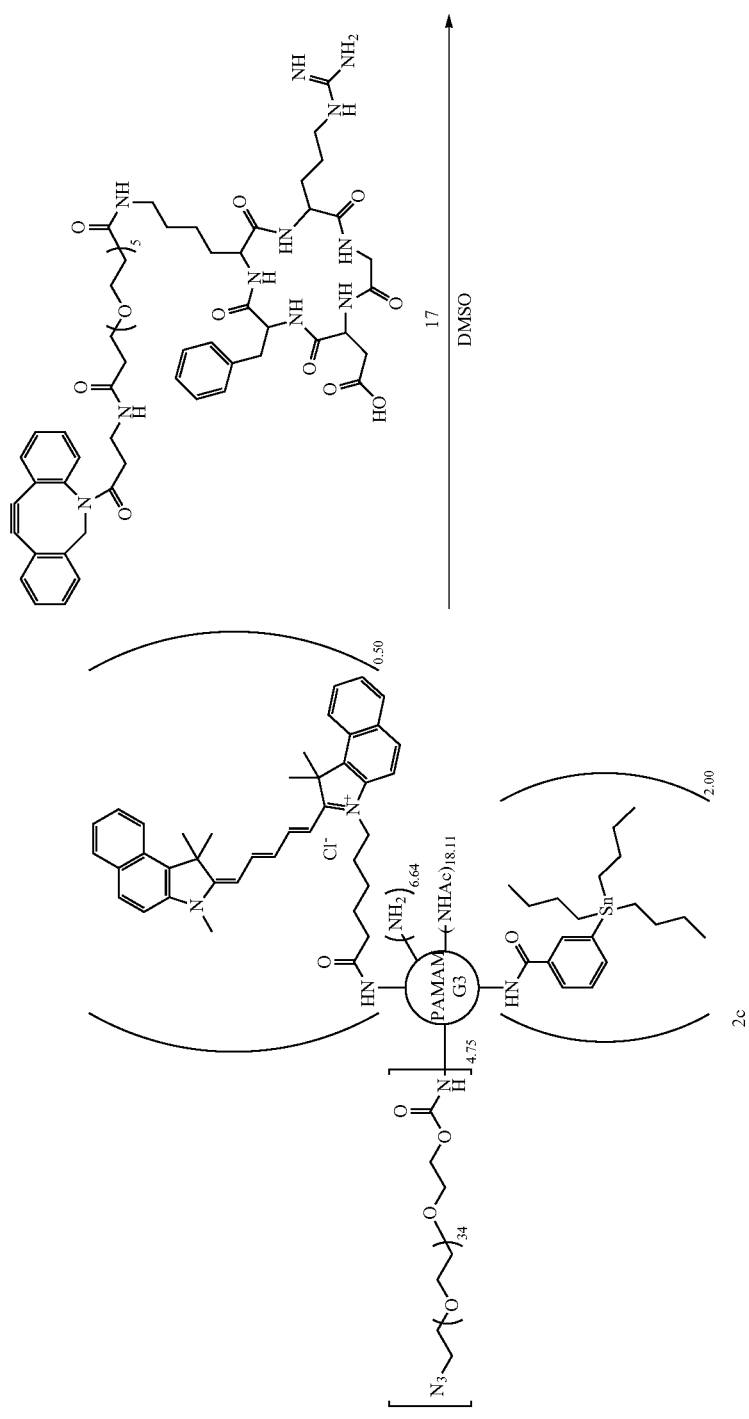

-continued
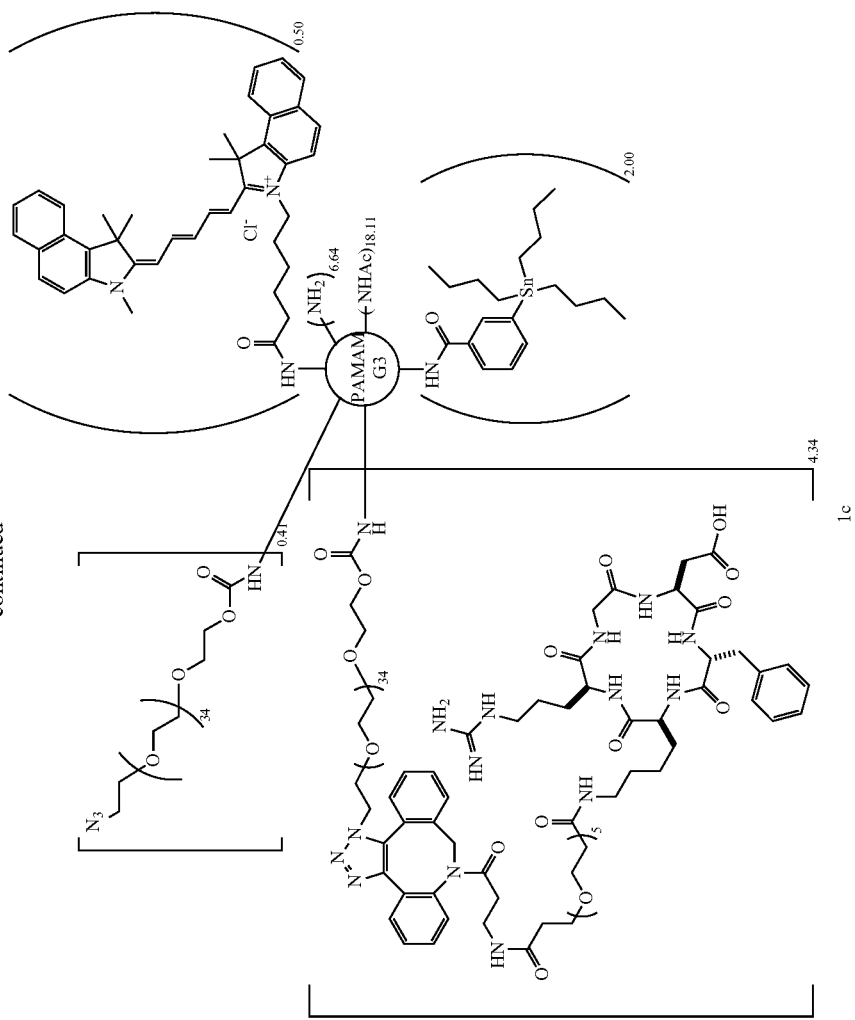

-continued
1c
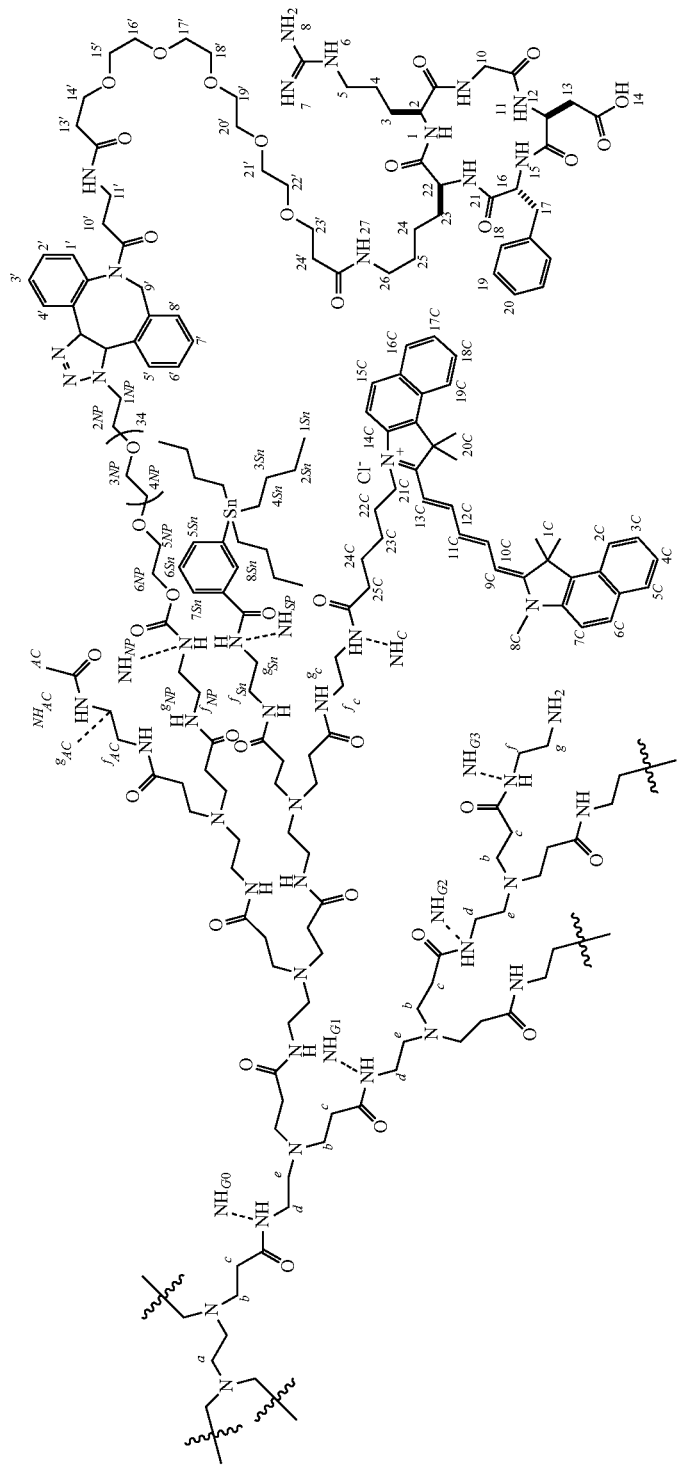

To a solution of Compound 2c (30.6 mg, 1.72 μmol) obtained in Step 1 in DMSO-$d_6$ (1.07 mL) was added a solution of Compound 17 (17.1 mg, 14.5 μmol) obtained in Preparational Example 2 in DMSO-$d_6$ (130 μL). The reaction was protected from light and stirred at room temperature for 24 h. In a dark room, the crude mixture was purified by a preparative SEC (model: Bio-Beads S-X1, H 38 cm×O.D. 3 cm, manufacturer: Bio-Rad) in DMF. The SEC fractions containing the product were combined and dried extensively in vacuo to give Compound 1c' (structure not shown). Unfortunately, the analysis of Compound 1c' by $^1$H NMR in DMSO-$d_6$ indicated only ca. 3.64 RGD moieties were attached out of ca. five available azide groups of Compound 2c. In an attempt to bring the RGD attachment to completion, another round of click reaction was pursued by dissolving Compound 17 (10.5 mg, 8.86 μmol) and Compound 1c' in DMSO-$d_6$ (1.2 mL). The reaction was protected from light and stirred at room temperature for 67 h under a dry Ar atmosphere. In a dark room, the crude mixture was purified by SEC twice: Bio-Beads S-X1 (H 39.5 cm×O.D. 3 cm, manufacturer: Bio-Rad) in DMF and Sephadex LH-20 (H 36.5 cm×O.D. 3 cm) in methanol. The SEC fractions containing the product were combined, concentrated under reduced pressure, and dried extensively in vacuo to give 34.2 mg of Compound 1c.

$^1$H NMR (600 MHz, DMSO-$d_6$) δ 5.90, 4.34 (ABq, 4.34H, $H_9$), 5.84, 4.45 (ABq, 4.34H, $H_{9'}$), 0.84 (m, 18.00H, J=6.2 Hz, $H_{1Sn}$);

MS (MALDI-TOF, DHB matrix) $M_n$ 20515.14, $M_w$ 21212.98, PDI 1.03.

Example 4

Preparation of Dendrimer Conjugate (1d)

Step 1: Modification of the Residual Surface Groups [Preparation of Dendrimer Conjugate (2d)]

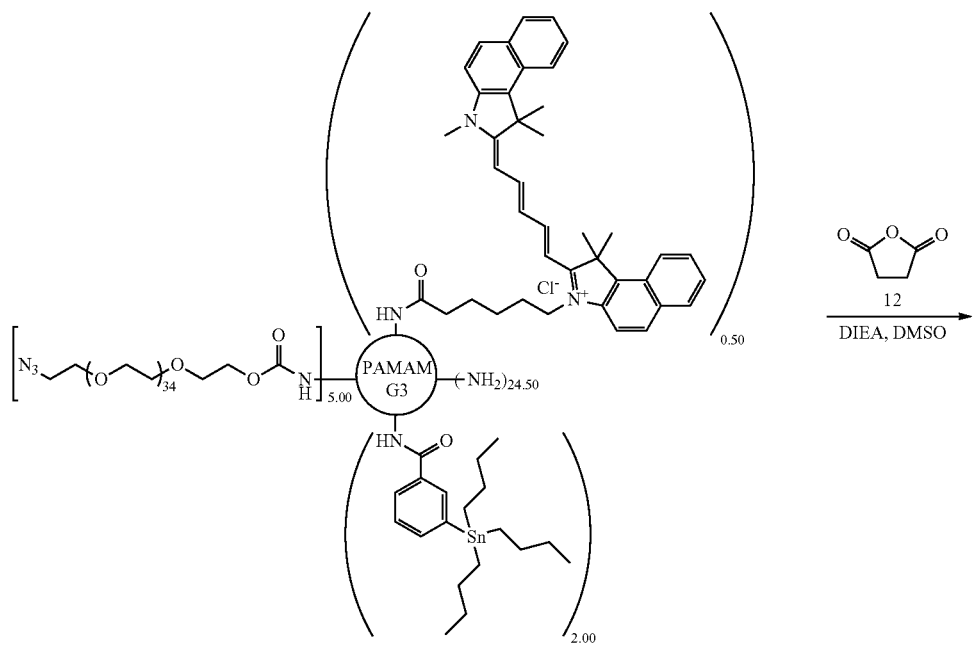

-continued

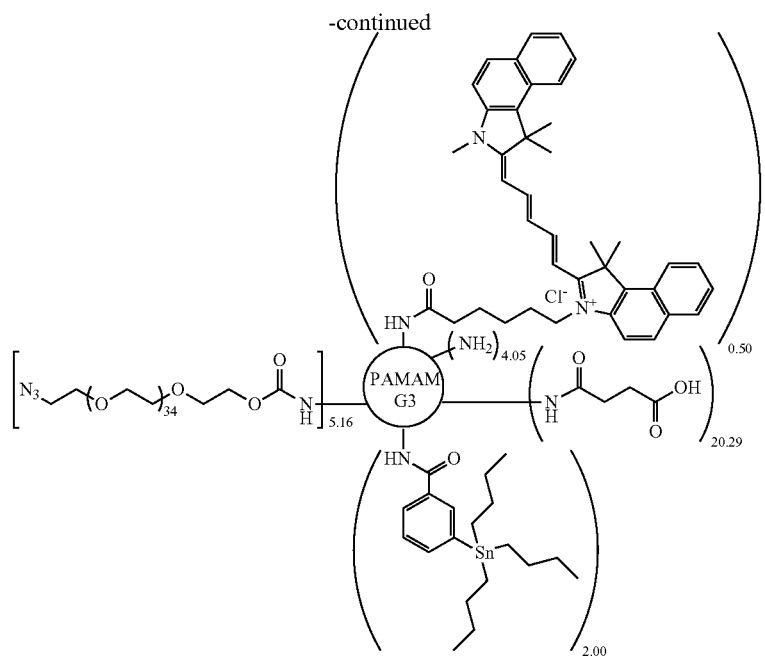

2d

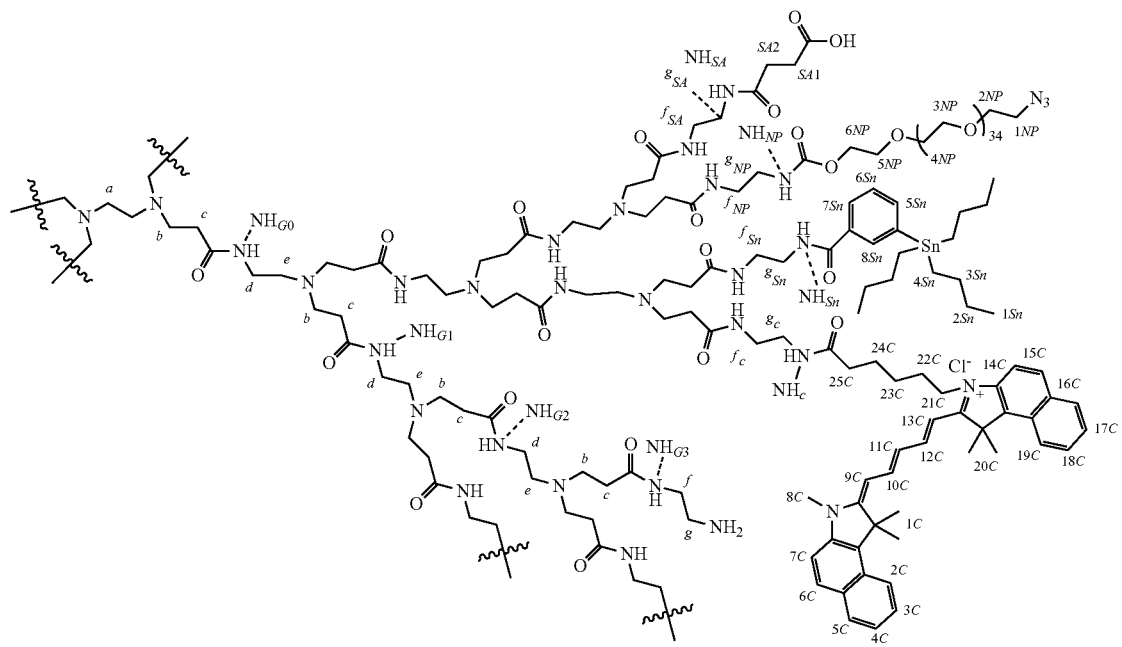

2d

To a portion of the crude reaction mixture of Compound 2a (1.70 mL, ca. 2.45 μmol) obtained in Step 2 of Example 1 were added succinic anhydride (Compound 12, 19.6 mg, 196 μmol) and DIEA (21.0 μL, 122 μmol) followed by DMSO-d$_6$ (200 μL). The reaction was protected from light and stirred at room temperature for 60 h under a dry Ar atmosphere. In a dark room, the crude mixture was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 38.5 cm×O.D. 3 cm, manufacturer: Bio-Rad) in DMF. The SEC fractions containing the product were combined, concentrated under reduced pressure, and dried extensively in vacuo to give 37.9 mg of Compound 2d.

$^1$H NMR (600 MHz, DMSO-d$_6$) δ 4.03 (m, 10.31H, H$_{6NP}$), 3.65-3.37 (m, 753.15H, H$_{1NP}$, H$_{2NP}$, H$_{3NP}$, H$_{4NP}$, and H$_{5NP}$), 3.18-2.91 (m, 164.65H, H$_d$, H$_f$, H$_{fNP}$, H$_{gNP}$, H$_{fSn}$, H$_{gSn}$, H$_{fSA}$, and H$_{gSA}$), 2.80-2.55 (m, 113.75H, H$_b$ and H$_g$), 2.46-2.34 (m, 108.41H, H$_e$, H$_a$, and H$_{SA2}$), 2.33-2.09 (m, 116.84H, H$_c$ and H$_{SA1}$), 1.50 (m, 14.49H, H$_{4Sn}$), 1.28 (m, 15.65H, H$_{3Sn}$), 1.06 (m, 11.60H, H$_{2Sn}$), 0.84 (t, 18.00H, J=7.0 Hz, H$_{1Sn}$).

Step 2: Attachment of Ligand Moieties to the Azide End of PEG by Click Reaction [Preparation of Dendrimer Conjugate (1d)]

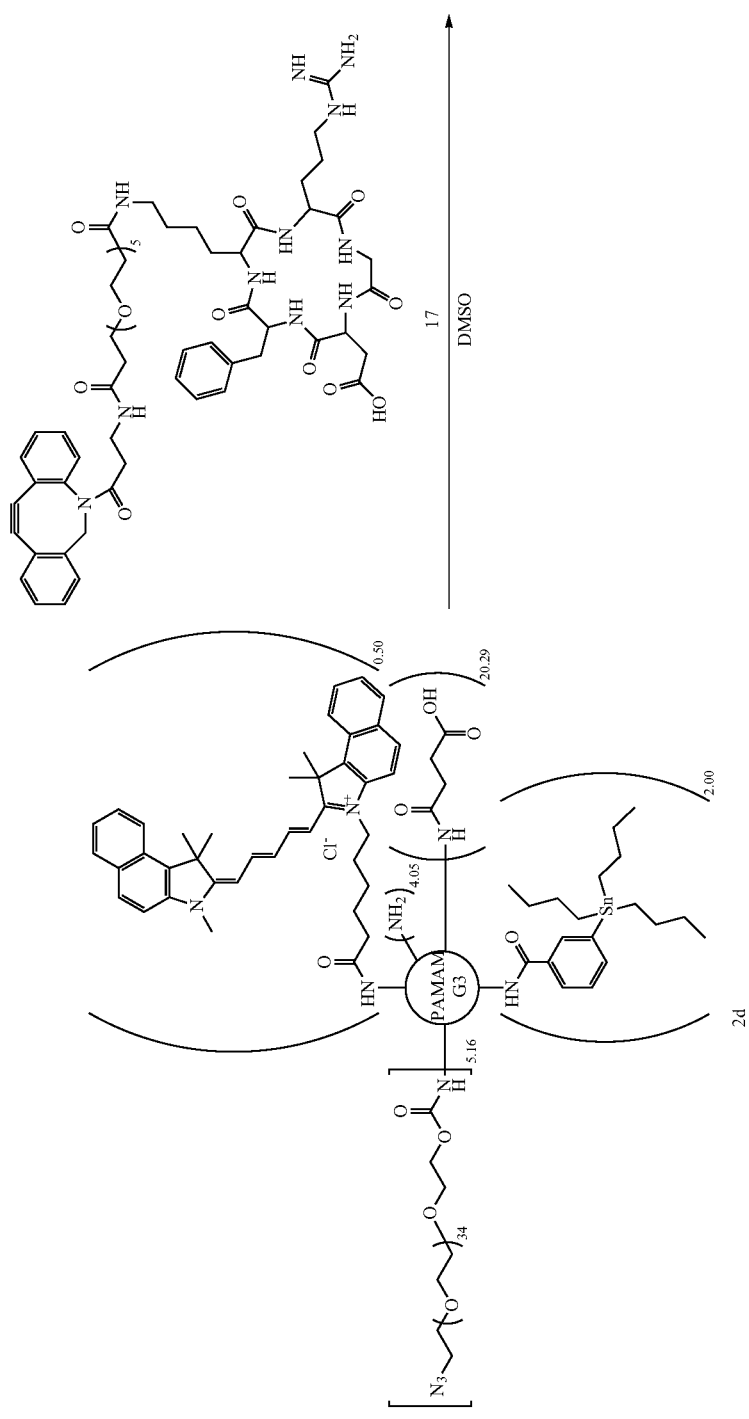

-continued
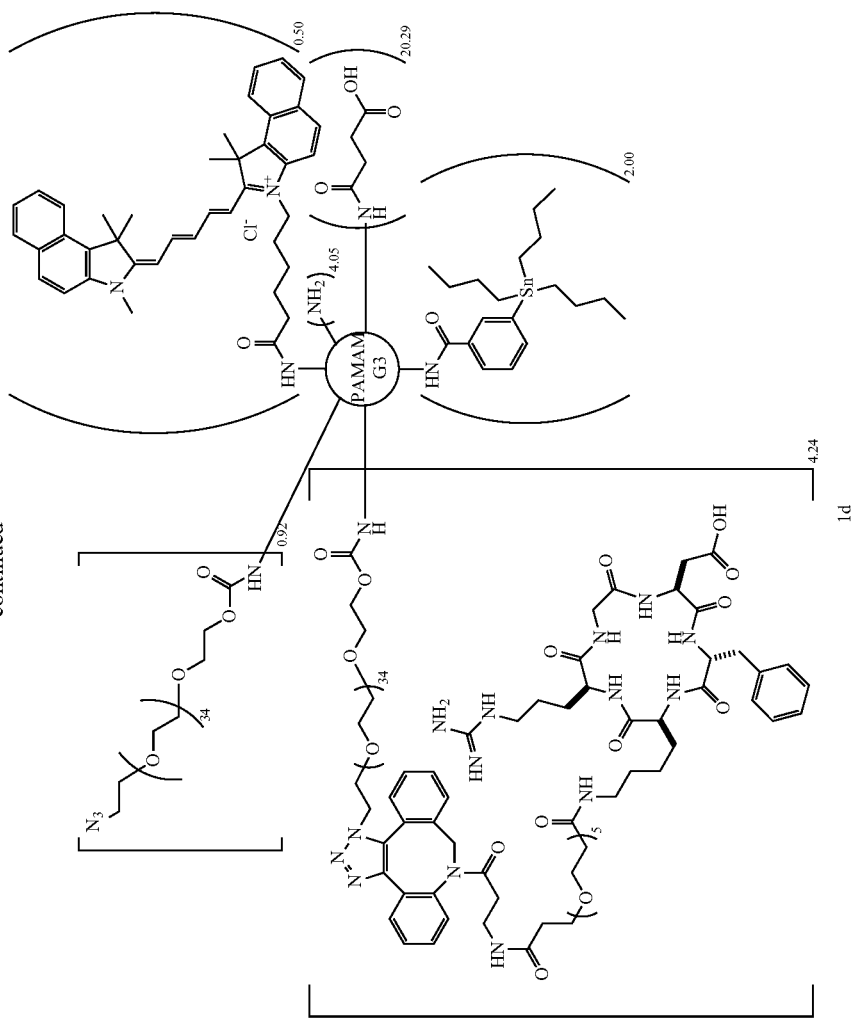
1d

-continued
1d
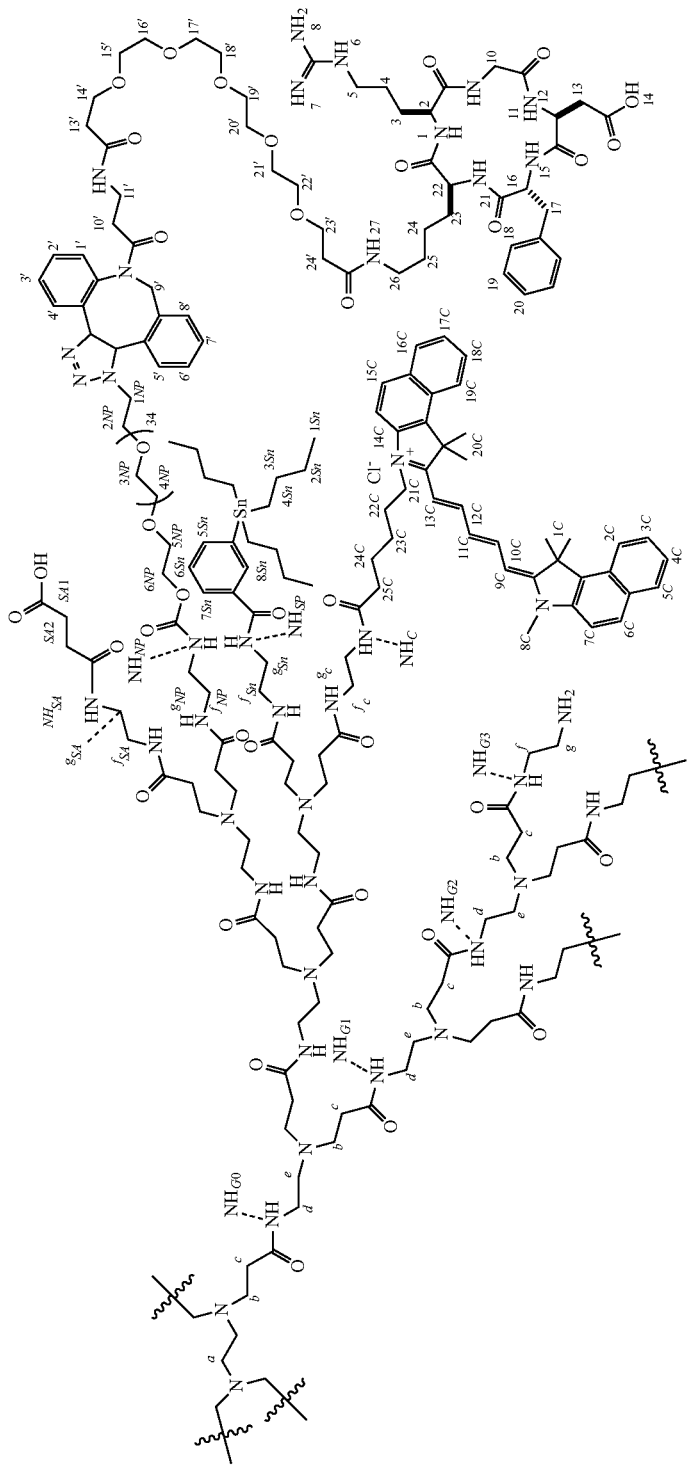

To a solution of Compound 2d (33.8 mg, 1.73 μmol) obtained in Step 1 in DMSO-$d_6$ (1.06 mL) was added a solution of Compound 17 (17.6 mg, 14.9 μmol) obtained in Preparational Example 2 in DMSO-$d_6$ (140 μL). The reaction was protected from light and stirred at room temperature for 24 h. In a dark room, the crude mixture was purified by a preparative SEC (model: Bio-Beads S-X1, H 38.5 cm×O.D. 3 cm, manufacturer: Bio-Rad) in DMF. The SEC fractions containing the product were combined and dried extensively in vacuo to give Compound 1d' (structure not shown). Unfortunately, the analysis of Compound 1d' by $^1$H NMR in DMSO-$d_6$ indicated only ca. 3.36 RGD moieties were attached out of ca. five available azide groups of Compound 2d. In an attempt to bring the RGD attachment to completion, another round of click reaction was pursued by adding a solution of Compound 17 (10.5 mg, 8.88 μmol) obtained in Preparational Example 2 in DMSO-$d_6$ (360 μL) to the solution of Compound 1d' (ca. 1.73 μmol) in DMSO-$d_6$ (840 μL). The reaction was protected from light and stirred at room temperature for 24 h under a dry Ar atmosphere. In a dark room, the crude mixture was purified by SEC twice: Bio-Beads S-X1 (H 38 cm×O.D. 3 cm, manufacturer: Bio-Rad) in DMF and Sephadex LH-20 (H 37 cm×O.D. 3 cm) in methanol. The SEC fractions containing the product were combined, concentrated under reduced pressure, and dried extensively in vacuo to give 37.1 mg of Compound 1d.

$^1$H NMR (600 MHz, DMSO-$d_6$) δ 5.91, 4.48 (ABq, 4.24H, $H_{9'}$), 5.85, 4.45 (ABq, 4.24H, $H_{9'}$), 0.84 (m, 18.00H, J=6.7 Hz, $H_{1Sn}$);

MS (MALDI-TOF, DHB matrix) $M_n$ 20869.54, $M_w$ 22071.56, PDI 1.06.

Example 5

Preparation of Dendrimer Conjugate (1e)

Step 1: Modification of the Residual Surface Groups [Preparation of Dendrimer Conjugate (2e)]

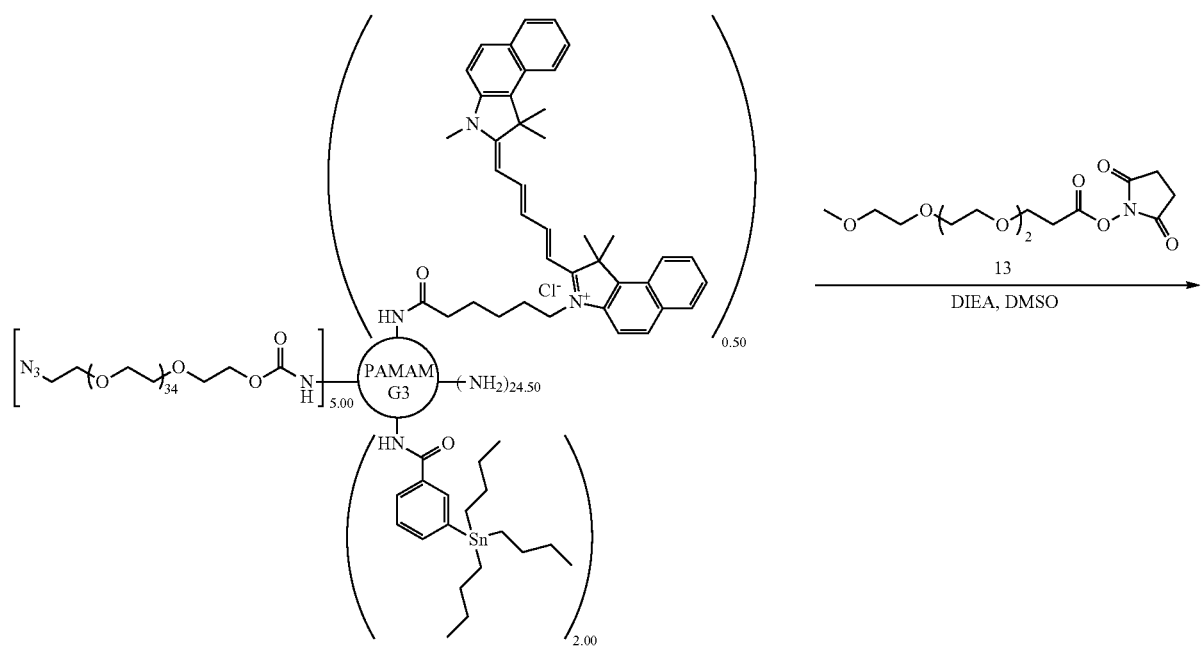

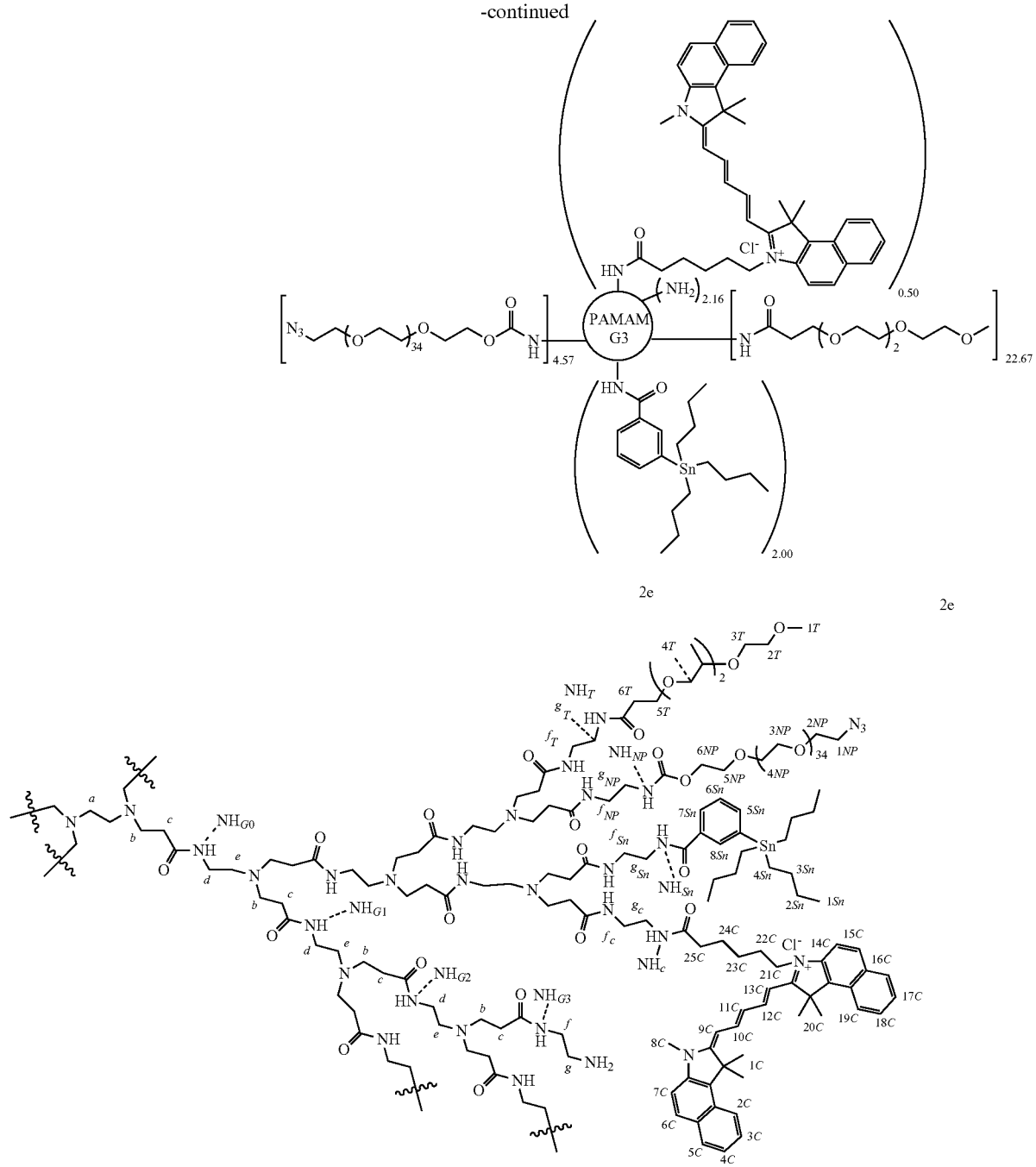

To a portion of the crude reaction mixture of Compound 2a (1.70 mL, ca. 2.45 μmol) obtained in Step 2 of Example 1 was added DIEA (21.0 μL, 122 μmol) followed by a solution of m-dPEG$_4$-NHS ester (purchased from Quanta BioDesign, MW 333.33; Compound 13, 59.7 mg, 183 μmol) in DMSO-d$_6$ (200 μL). The reaction was protected from light and stirred at room temperature for 12 h under a dry Ar atmosphere. In a dark room, the crude mixture was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 39 cm×O.D. 3 cm, manufacturer: Bio-Rad) in DMF. The SEC fractions containing the product were combined, concentrated under reduced pressure, and dried extensively in vacuo to give 41.9 mg of Compound 2e.

$^1$H NMR (600 MHz, DMSO-d$_6$) δ 4.03 (m, 9.33H, H$_{6NP}$), 3.64-3.37 (m, 976.30H, H$_{1NP}$, H$_{2NP}$, H$_{3NP}$, H$_{4NP}$, H$_{5NP}$, H$_{2T}$, H$_{3T}$, H$_{4T}$, and H$_{5T}$), 3.23 (s, 68.54H, H$_{1T}$), 3.16-2.97 (m, 169.91H, H$_d$, H$_f$, H$_{fNP}$, H$_{gNP}$, H$_{fSn}$, H$_{gSn}$, H$_{fT}$, and H$_{gT}$), 2.73-2.55 (m, 113.75H, H$_b$ and H$_g$), 2.42 (m, 60.58H, H$_e$ and H$_a$), 2.35-2.09 (m, 160.56H, H$_c$ and H$_{6T}$), 1.50 (m, 14.78H, H$_{4Sn}$), 1.28 (m, 16.93H, H$_{3Sn}$), 1.06 (m, 12.64H, H$_{2Sn}$), 0.84 (t, 18.00H, J=6.4 Hz, H$_{1Sn}$).

Step 2: Attachment of Ligand Moieties to the Azide End of PEG by Click Reaction [Preparation of Dendrimer Conjugate (1e)]

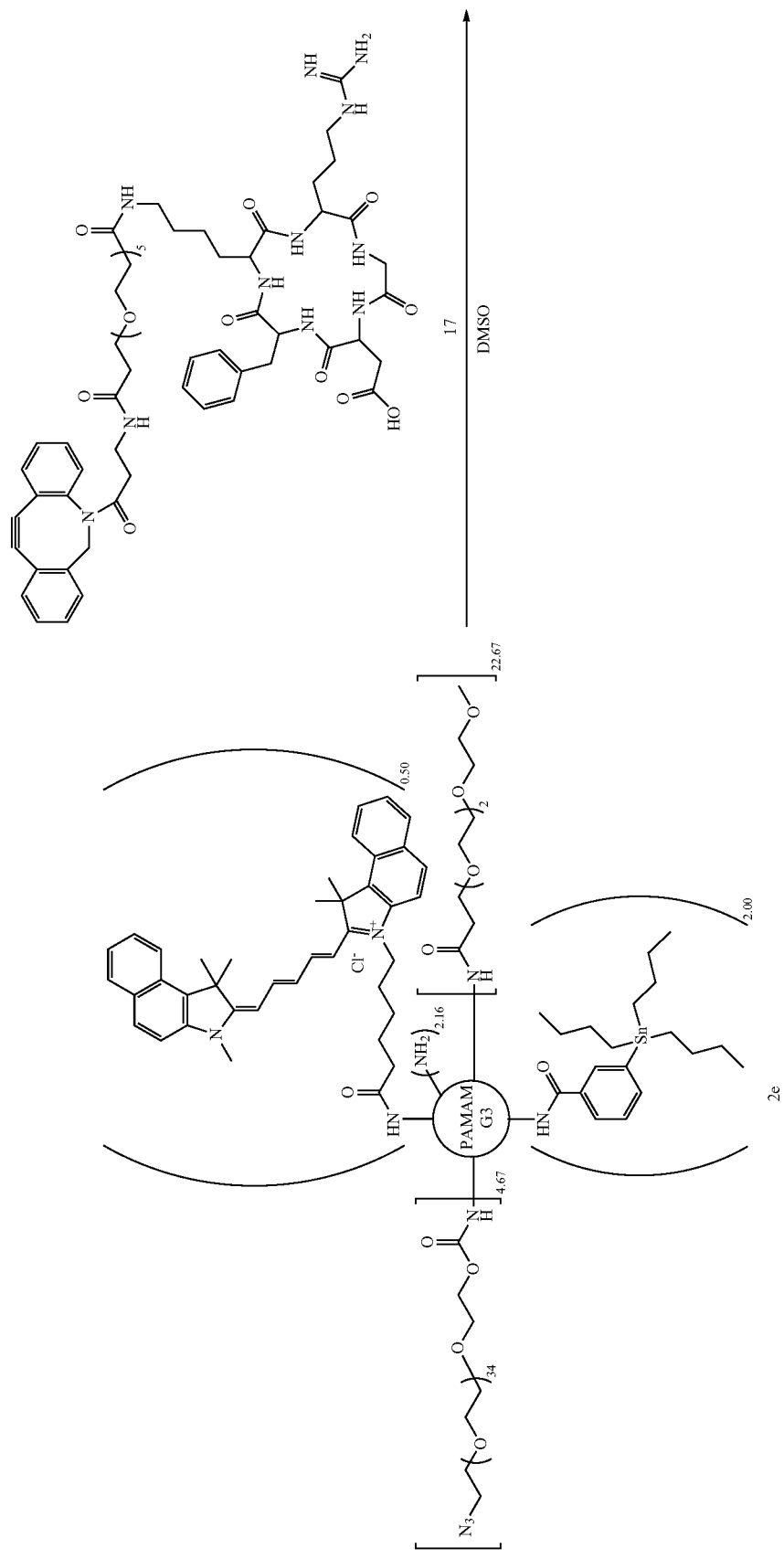

-continued
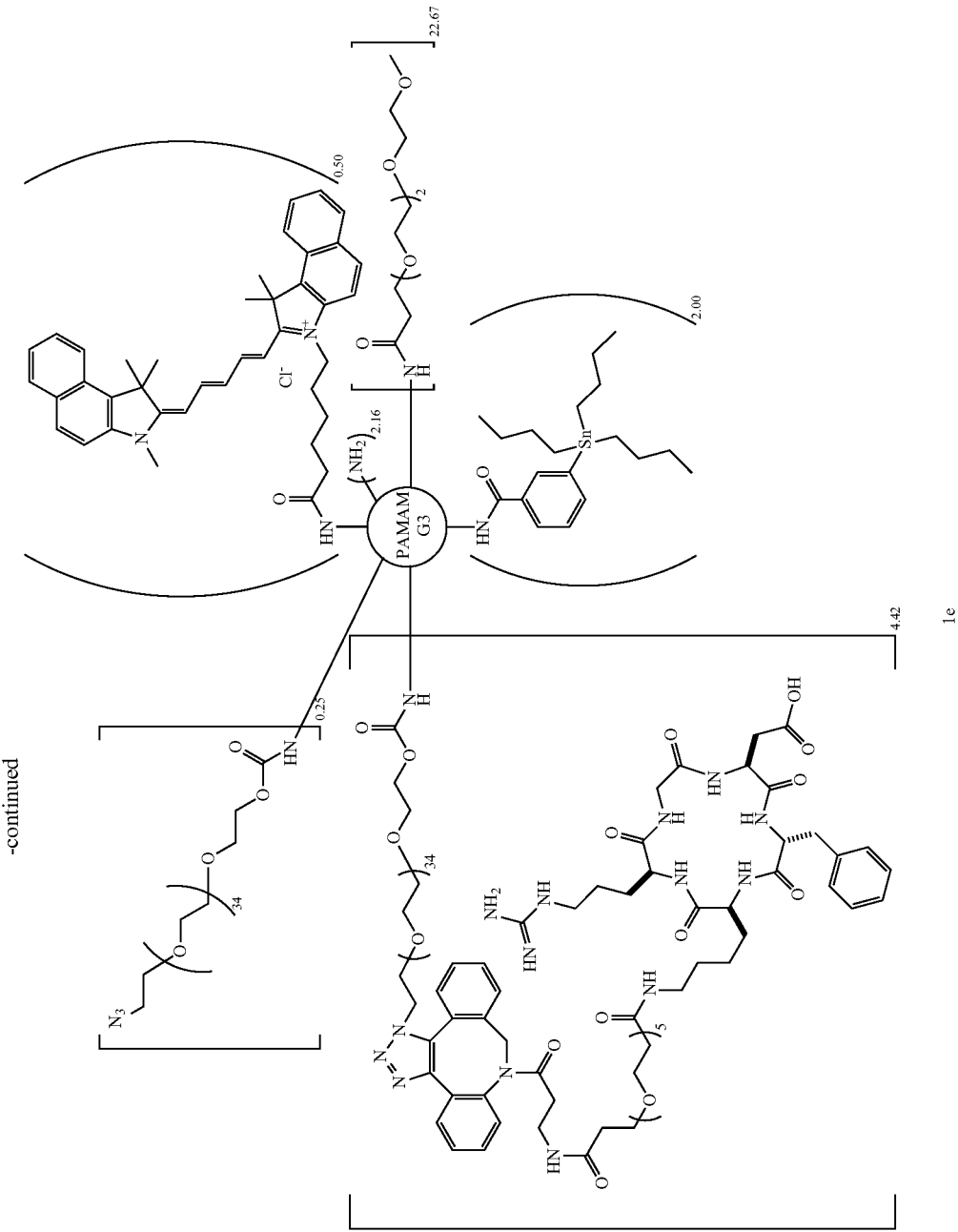

-continued
1e
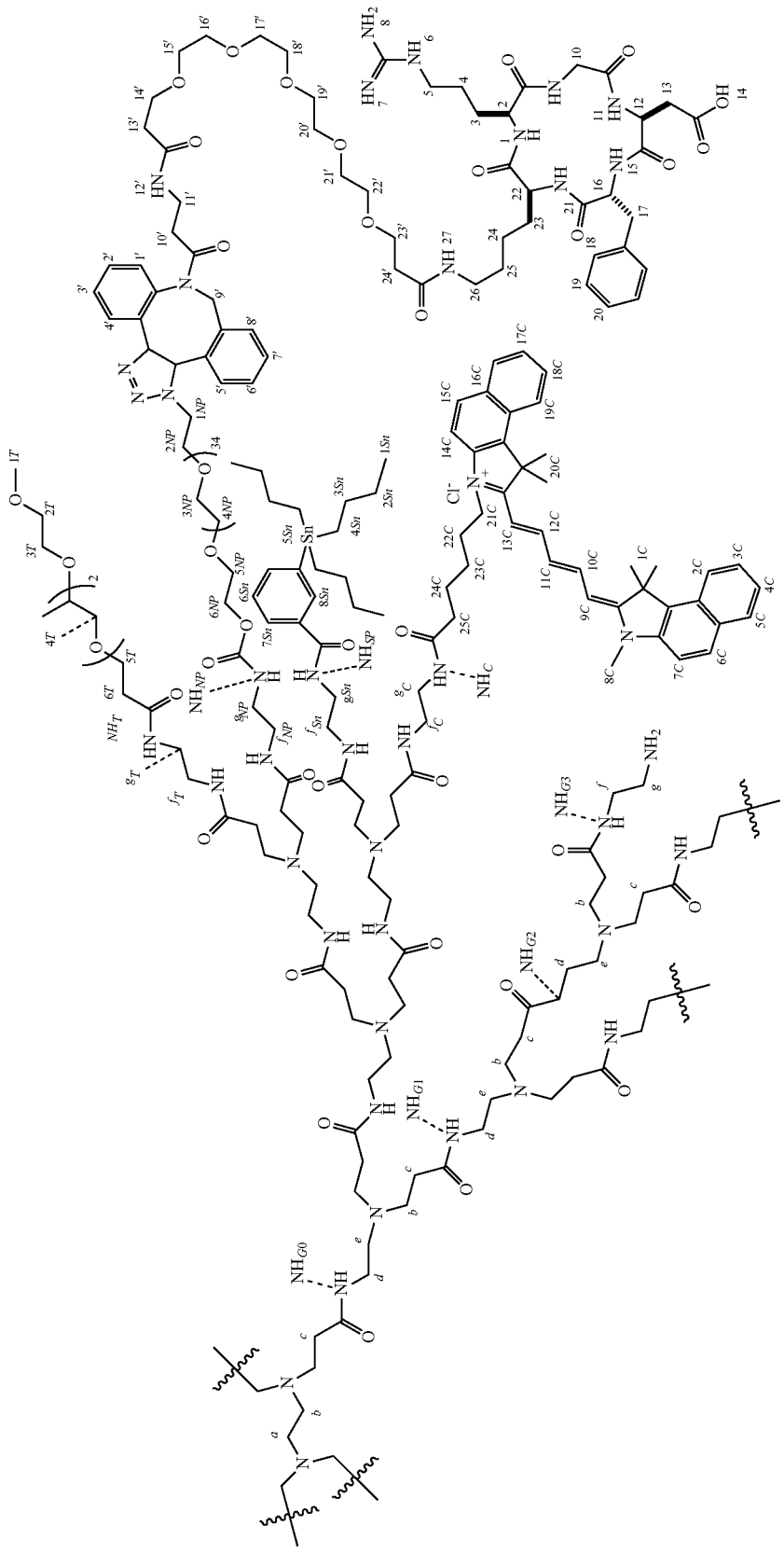

To a solution of Compound 2e (35.6 mg, 1.70 μmol) obtained in Step 1 in DMSO-$d_6$ (980 μL) was added a solution of Compound 17 (15.8 mg, 13.4 μmol) obtained in Preparational Example 2 in DMSO-$d_6$ (120 μL). The reaction was protected from light and stirred at room temperature for 24 h. In a dark room, the crude mixture was purified by a preparative SEC (model: Bio-Beads S-X1, H 38.5 cm×O.D. 3 cm, manufacturer: Bio-Rad) in DMF. The SEC fractions containing the product were combined and dried extensively in vacuo to give Compound 1e' (structure not shown). Unfortunately, the analysis of Compound 1e' by $^1$H NMR in DMSO-$d_6$ indicated only ca. 2.84 RGD moieties were attached out of ca. five available azide groups of Compound 2e. In an attempt to bring the RGD attachment to completion, another round of click reaction was pursued by dissolving Compound 17 (12.8 mg, 10.8 μmol) obtained in Preparational Example 2 and Compound 1e' (ca. 1.69 μmol) in DMSO-$d_6$ (1.1 mL). The reaction was protected from light and stirred at room temperature for 24 h under a dry Ar atmosphere. In a dark room, the crude mixture was purified by SEC twice: Bio-Beads S-X1 (H 31.5 cm×O.D. 3 cm, manufacturer: Bio-Rad) in DMF and Sephadex LH-20 (H 38 cm×O.D. 3 cm) in methanol. The SEC fractions containing the product were combined, concentrated under reduced pressure, and dried extensively in vacuo to give 38.2 mg of Compound 1e.

$^1$H NMR (600 MHz, DMSO-$d_6$) δ 5.91, 4.48 (ABq, 4.42H, $H_9$), 5.84, 4.51 (ABq, 4.42H, $H_{9'}$), 0.84 (m, 18.00H, J=6.7 Hz, $H_{1Sn}$);

MS (MALDI-TOF, DHB matrix) $M_n$ 22901.16, $M_w$ 23675.78, PDI 1.03.

Example 6

Preparation of Dendrimer Conjugate (1f)

Step 1: Modification of the Residual Surface Groups [Preparation of Dendrimer Conjugate (2f)

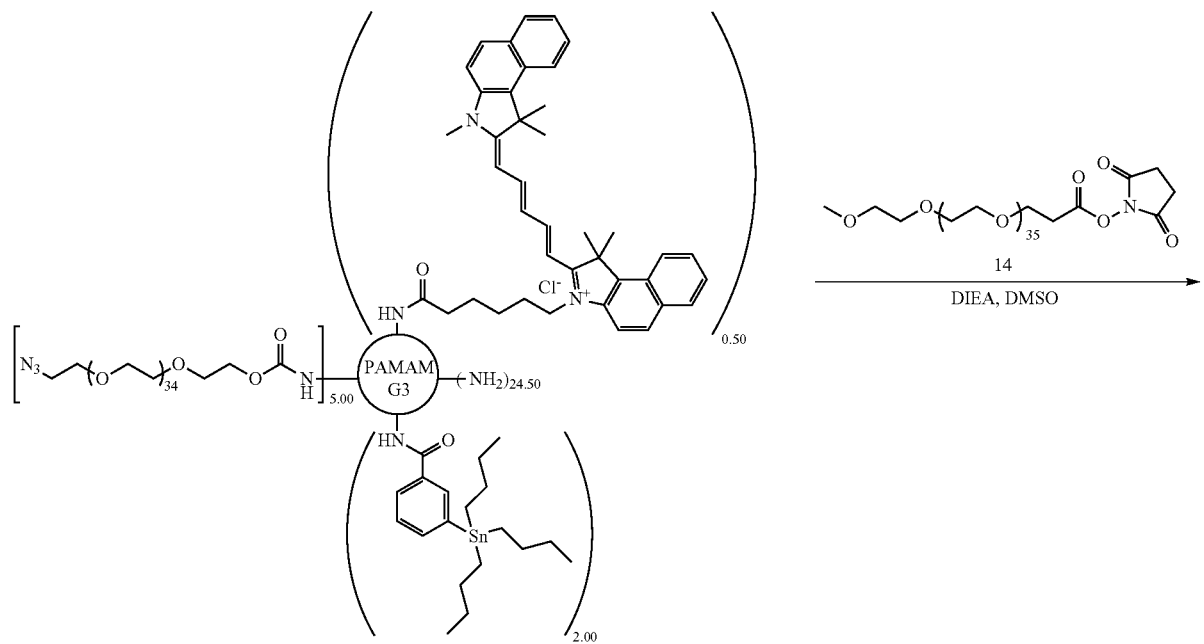

2a

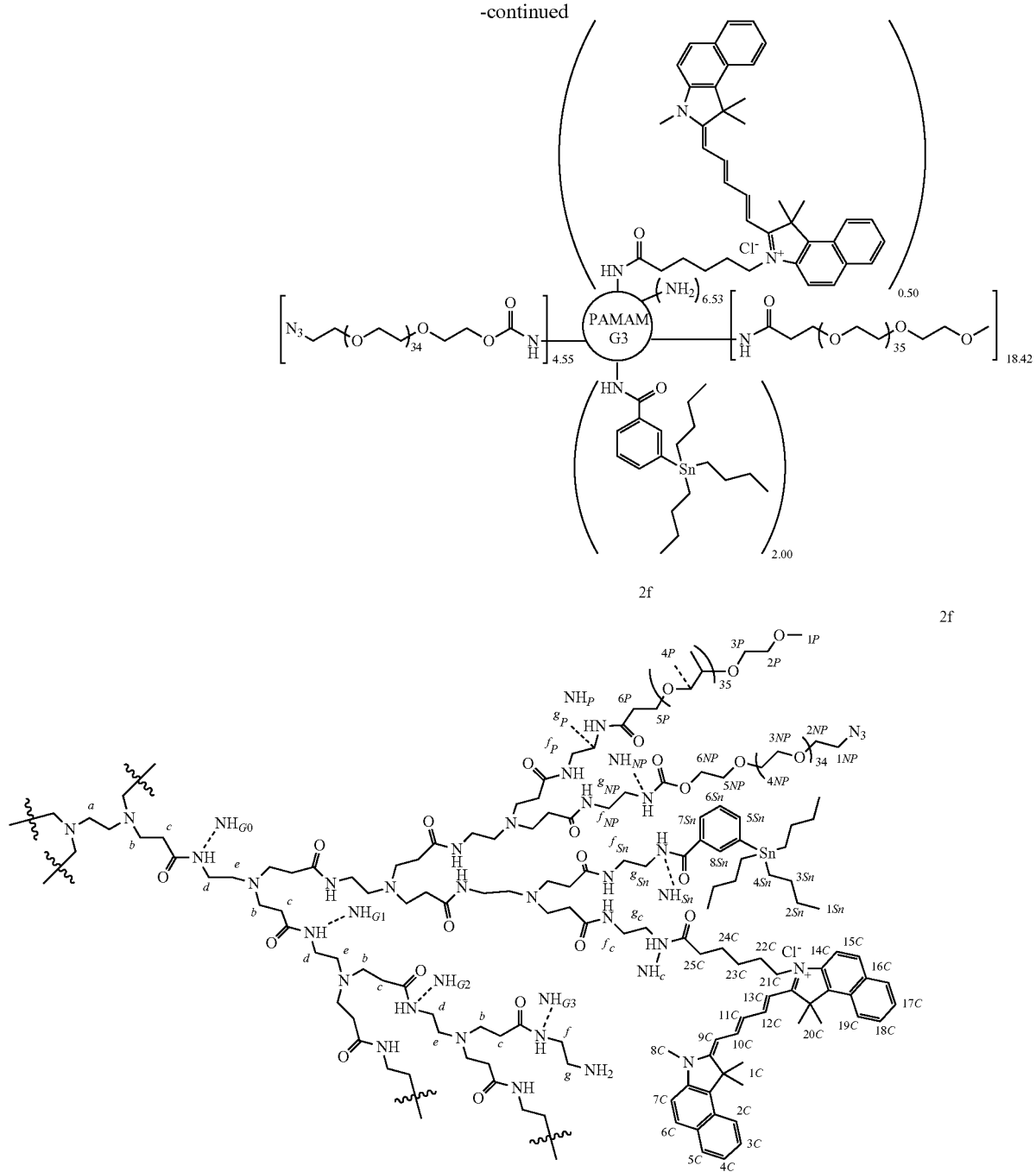

2f

To a portion of the crude reaction mixture of Compound 2a (1.70 mL, ca. 2.45 μmol) obtained in Step 2 of Example 1 was added DIEA (21.0 μL, 122 μmol) followed by m-dPEG$_{37}$-NHS ester (purchased from Quanta BioDesign, MW 1787.07; Compound 14, 328 mg, 184 μmol). The reaction was protected from light and stirred at room temperature for 12 h under a dry Ar atmosphere. In a dark room, the crude mixture was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 37 cm×O.D. 3 cm, manufacturer: Bio-Rad) in DMF. The SEC fractions containing the product were combined, concentrated under reduced pressure, and dried extensively in vacuo to give 89.9 mg of Compound 2f.

$^1$H NMR (600 MHz, DMSO-d$_6$) δ 4.03 (m, 9.10H, H$_{6NP}$), 3.64-3.38 (m, 3340.32H, H$_{1NP}$, H$_{2NP}$, H$_{3NP}$, H$_{4NP}$, H$_{5NP}$, H$_{2P}$, H$_{3P}$, H$_{4P}$, and H$_{5P}$) 3.24 (s, 60.82H, H$_{1P}$), 3.18-2.96 (m, 162.16H, H$_d$, H$_f$, H$_{fNP}$, H$_{gNP}$, H$_{fSn}$, H$_{gSn}$, H$_{fP}$, and H$_{gP}$), 2.74-2.56 (m, 103.45H, H$_b$ and H$_g$), 2.42 (m, 61.86H, H$_e$ and H$_a$), 2.35-2.09 (m, 155.18H, H$_c$ and H$_{6P}$), 1.50 (m, 14.60H, H$_{4Sn}$), 1.28 (m, 16.19H, H$_{3Sn}$), 1.06 (m, 12.14H, H$_{2Sn}$), 0.84 (t, 18.00H, J=6.4 Hz, H$_{1Sn}$).

Step 2: Attachment of Ligand Moieties to the Azide End of PEG by Click Reaction [Preparation of Dendrimer Conjugate (1f)]

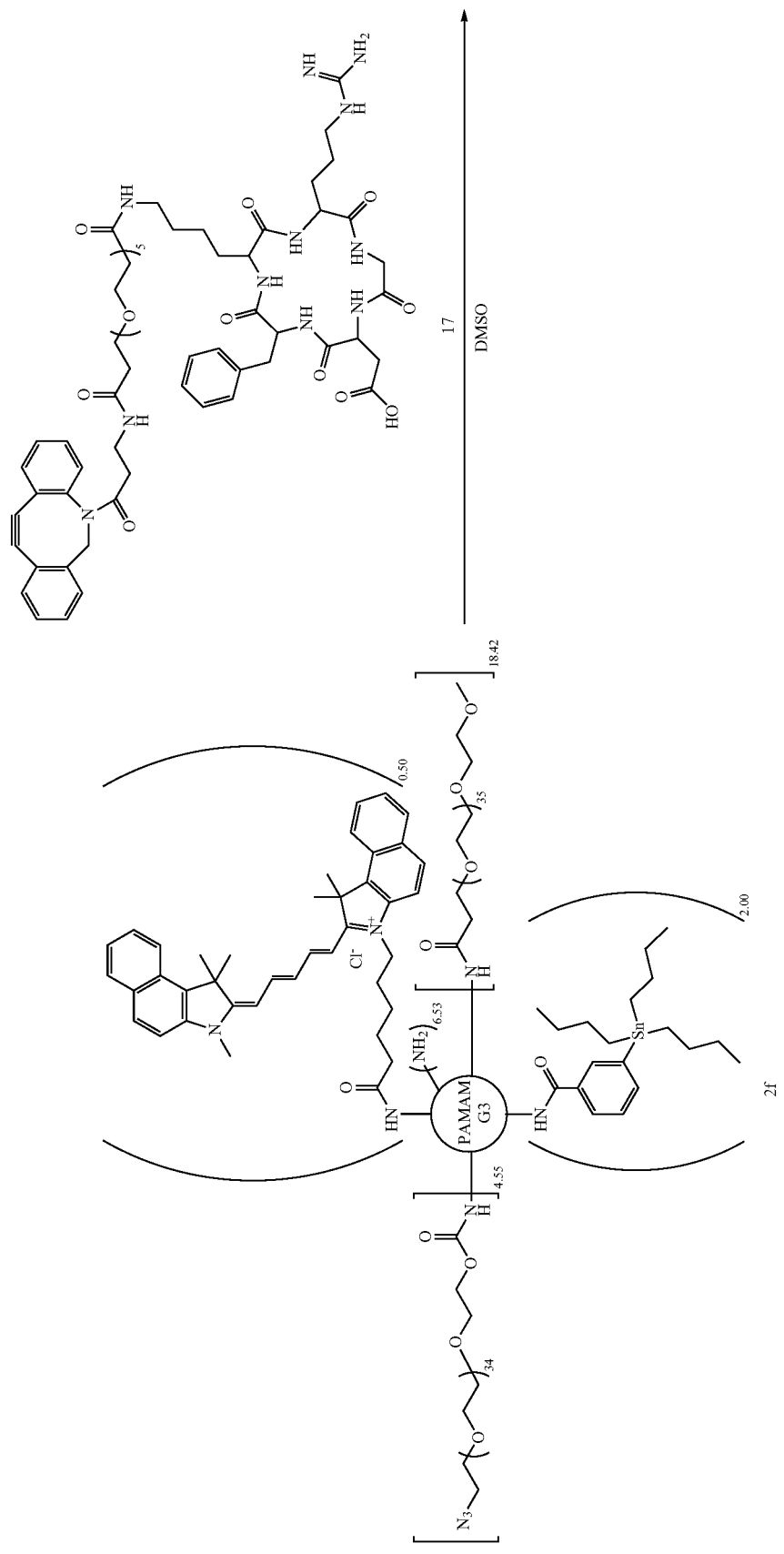

-continued
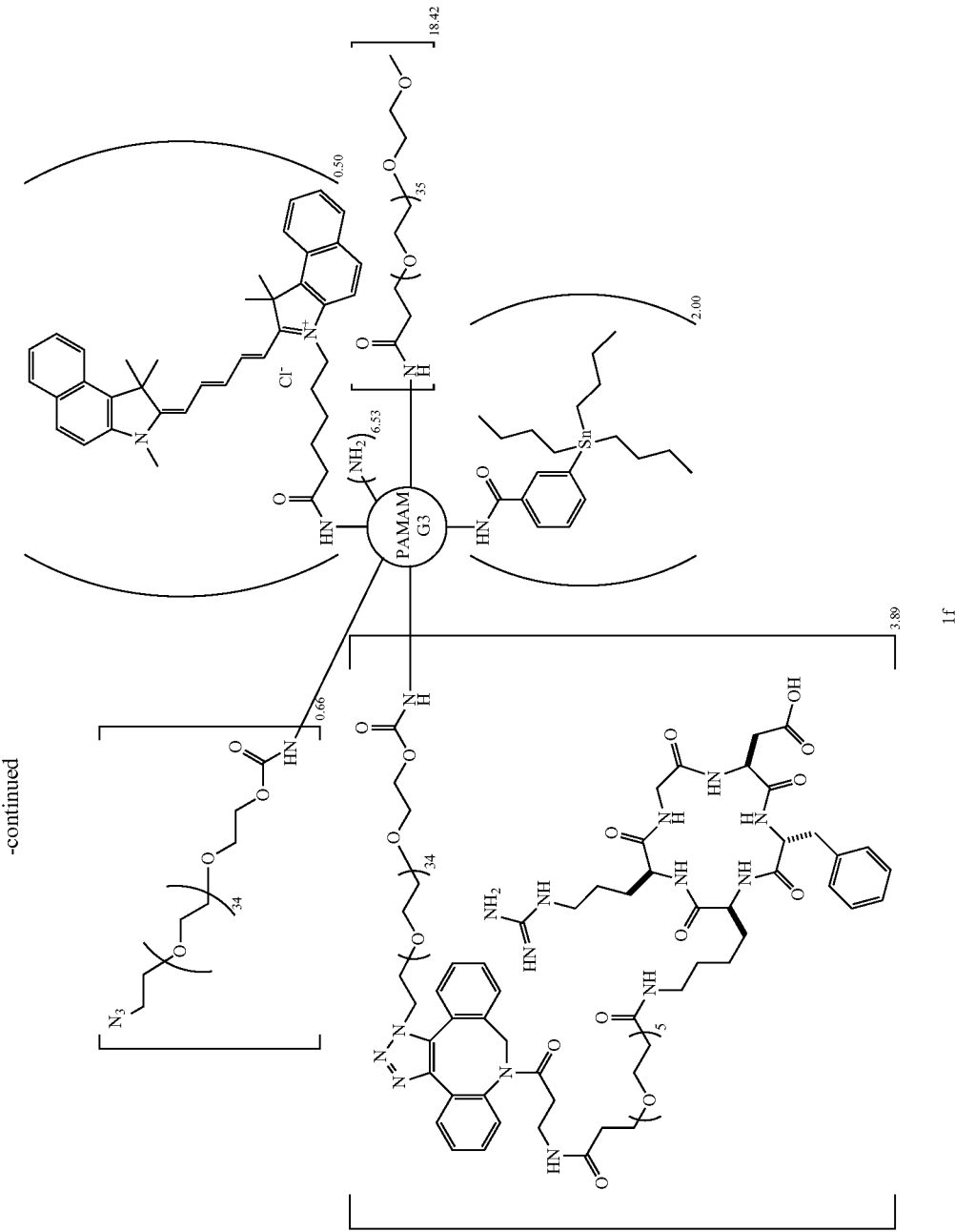
1f

-continued
1f
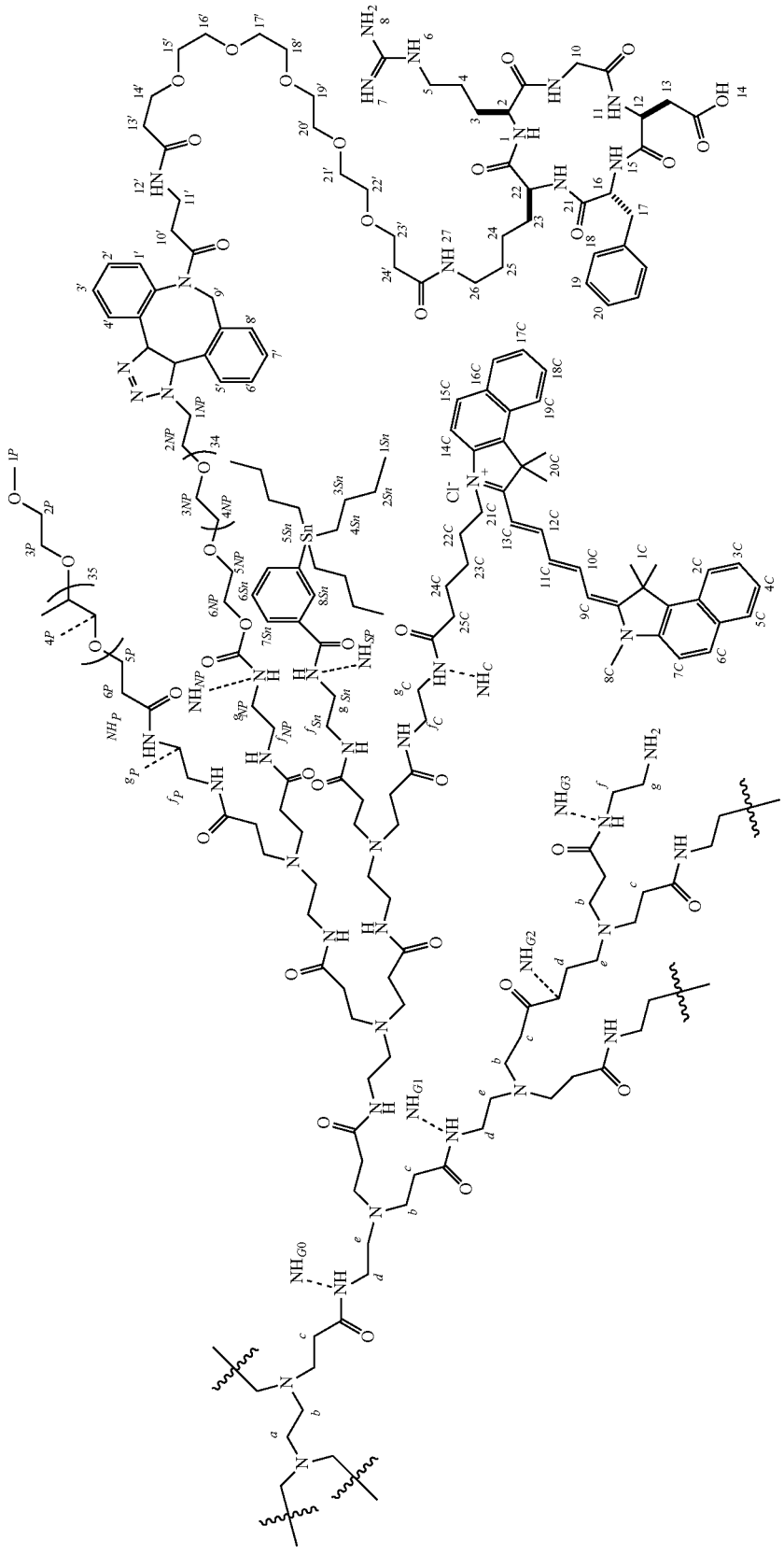

To a solution of Compound 2f (85.6 mg, 1.50 μmol) obtained in Step 1 in DMSO-$d_6$ (880 μL) was added a solution of Compound 17 (15.8 mg, 13.3 μmol) obtained in Preparational Example 2 in DMSO-$d_6$ (120 μL). The reaction was protected from light and stirred at room temperature for 24 h. In a dark room, the crude mixture was purified by a preparative SEC (model: Bio-Beads S-X1, H 40 cm×O.D. 4.5 cm, manufacturer: Bio-Rad) in DMF. The SEC fractions containing the product were combined and dried extensively in vacuo to give Compound 1f' (structure not shown). Unfortunately, the analysis of Compound 1f' by $^1$H NMR in DMSO-$d_6$ indicated only ca. 2.92 RGD moieties were attached out of ca. five available azide groups of Compound 2f. In an attempt to bring the RGD attachment to completion, another round of click reaction was pursued by adding a solution of Compound 17 (11.4 mg, 9.67 μmol) obtained in Preparational Example 2 in DMSO (400 μL) to the solution of Compound 1f' (ca. 1.69 μmol) in DMSO (600 μL). The reaction was protected from light and stirred at room temperature for 67 h under a dry Ar atmosphere. In a dark room, the crude mixture was purified by SEC twice: Bio-Beads S-X1 (H 38.5 cm×O.D. 4.5 cm, manufacturer: Bio-Rad) in DMF and Sephadex LH-20 (H 30 cm×O.D. 4.5 cm) in methanol. The SEC fractions containing the product were combined, concentrated under reduced pressure, and dried extensively in vacuo to give 86.1 mg of Compound 1f.

$^1$H NMR (600 MHz, DMSO-$d_6$) δ 5.91, 4.48 (ABq, 3.89H, $H_{9'}$), 5.84, 4.45 (ABq, 3.89H, $H_{9'}$), 0.84 (m, 18.00H, J=7.0 Hz, $H_{1Sn}$);

MS (MALDI-TOF, DHB matrix) $M_n$ 47052.00, $M_w$ 48559.83, PDI 1.03.

Example 7

Preparation of Dendrimer Conjugate (1g)

Step 1: Partial Derivatization of the Core with Azido-PEG Units [Preparation of Dendrimer conjugate (8)]

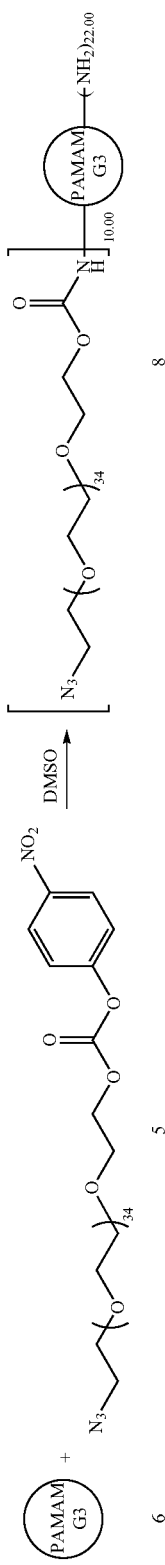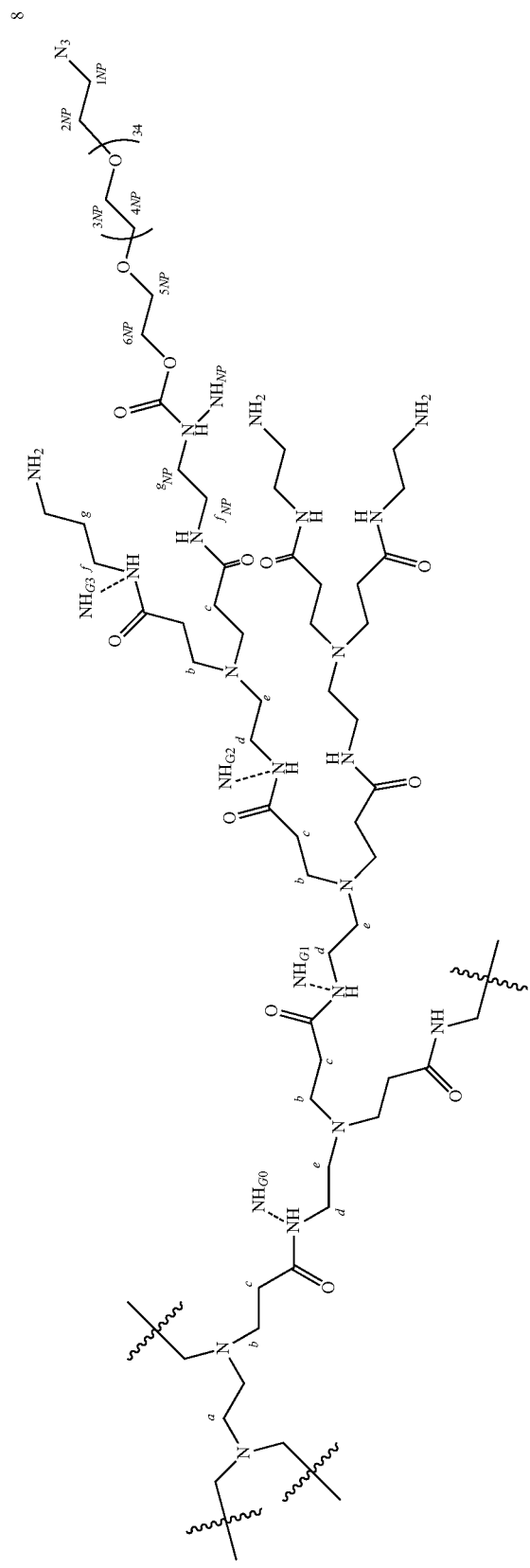

The methanolic solution of amine-terminated G3 PAMAM dendrimer (Compound 6, purchased from Dendritech) was dried in vacuo for 2 h and the resulting solid was weighed (237 mg, 34.4 μmol). The anhydrous DMSO (23 mL) was added to this dried Compound 6 to dissolve completely, and then to this stirred solution was slowly added a solution of Compound 5 (76 mol % purity, 793 mg, 344 μmol) obtained similarly as described in Preparational Example 1 in DMSO (? mL). The reaction was stirred at room temperature for 20 h under a dry Ar atmosphere. Next, the reaction mixture was dialyzed (model: Spectra/Por RC membrane, MWCO 3500, manufacturer: Spectrum Laboratories) against methanol (×2, for 12 h and 2 h, each) with stirring to remove DMSO and small molecular reagents such as Compound 5. After removal of the solvent under reduced pressure, the crude mixture was loaded on a SEC column (model: Bio-Beads S-X1, H 41.5 cm×O.D. 4.5 cm, manufacturer: Bio-Rad) in DMF to isolate the target Compound 8. The yellowish SEC fractions were combined, concentrated under reduced pressure, and dried in vacuo to give 390 mg of Compound 8.

$^1$H NMR (600 MHz, DMSO-$d_6$) δ 7.21 (br s, 9.99H, $NH_{NP}$ of major isomer), 6.80 (br s, 0.43H, $NH_{NP}$ of minor isomer), 4.04 (t, 20.16H, J=4.2 Hz, $H_{6NP}$), 3.65-3.37 (m, 1657.25H, $H_{1NP}$, $H_{2NP}$, $H_{3NP}$, $H_{4NP}$, and $H_{5NP}$), 3.15-2.98 (m, 170.98H, $H_d$, $H_f$, $H_{fNP}$, and $H_{gNP}$), 2.72-2.53 (m, 164.81H, $H_b$ and $H_g$), 2.20 (m, 120.00H, $H_c$).

Step 2: Partial Derivatization of the Core with Fluorophore and Precursor for Radiolabeling [Preparation of Dendrimer Conjugate (2g)]

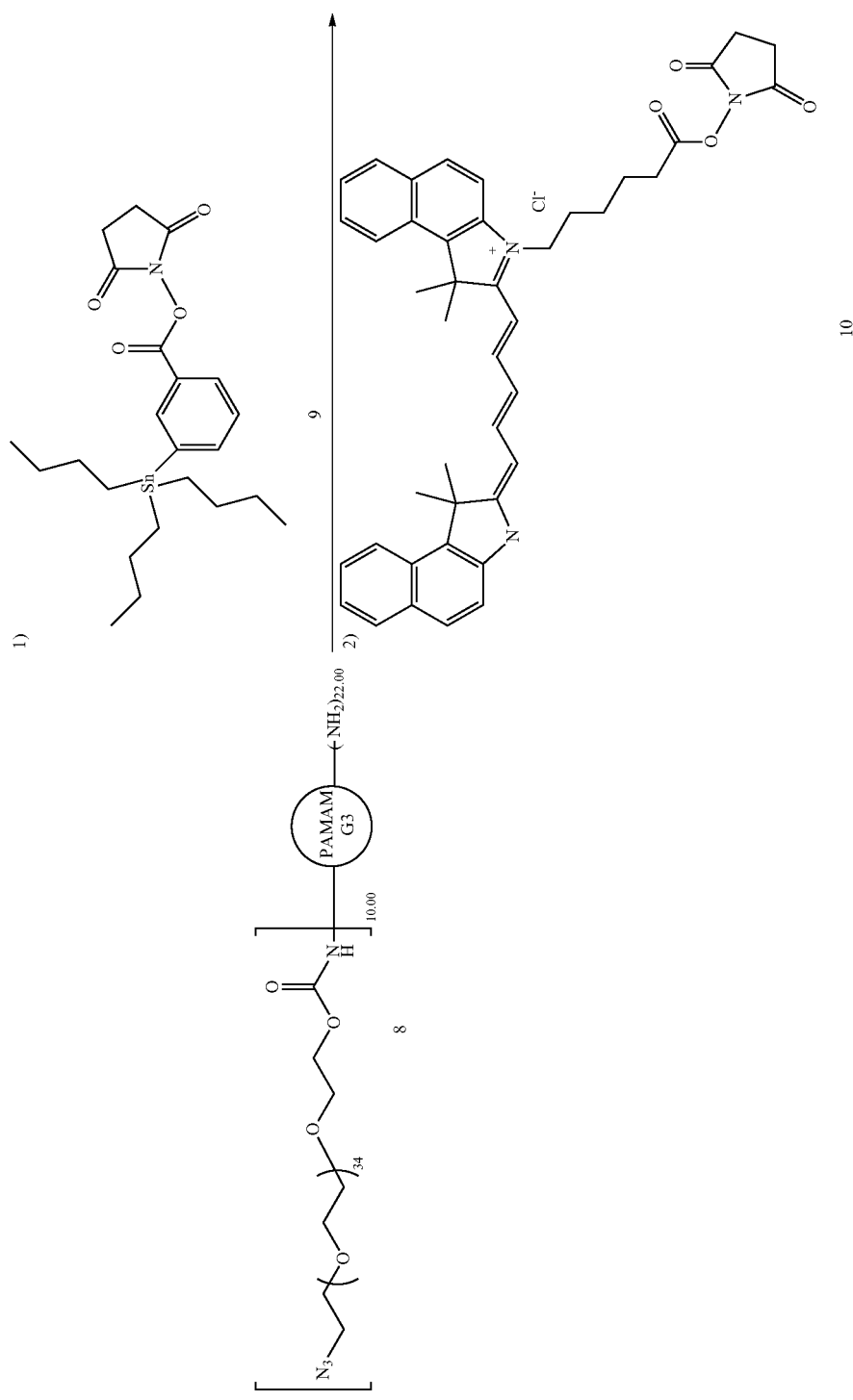

-continued
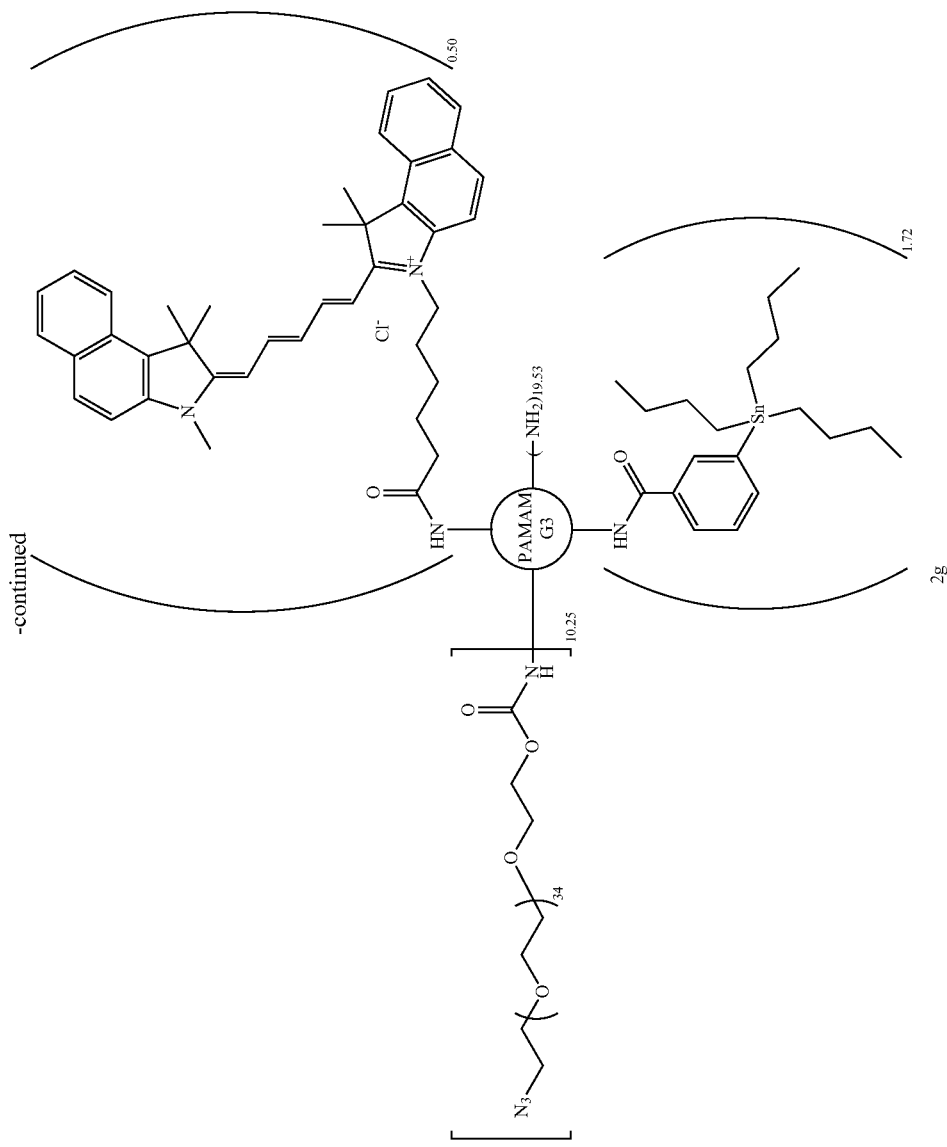

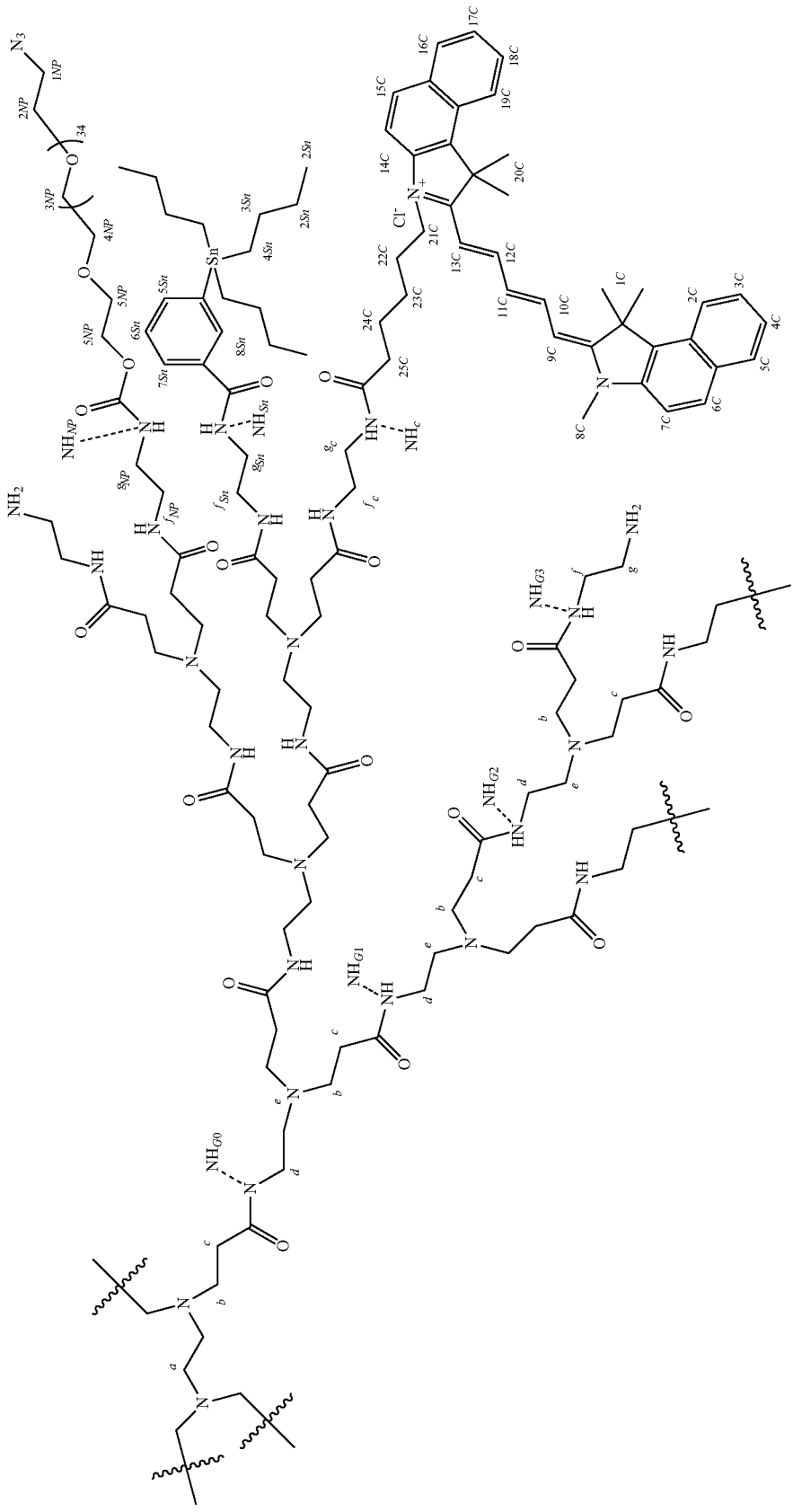

Compound 8 (379 mg, 16.6 µmol) obtained in Step 1 was dissolved completely in DMSO (8.0 mL) with vigorous sonication. To this stirred solution was added DIEA (11.6 µL, 66.5 µmol) followed by a solution of 3-(tri-n-butylstannyl)benzoyl NHS ester (Compound 9, purchased from Texas Biochemicals, 15.8 mg, 31.1 µmol) in DMSO (3.0 mL) dropwise over a 7-min period. The reaction was stirred at room temperature for 24 h under a dry Ar atmosphere. Subsequently, to this stirred solution was slowly added a solution of Cy5.5 NHS ester (Compound 10, purchased from Lumiprobe, 95% purity, 6.27 mg, 8.75 µmol) in DMSO-$d_6$ (300 µL). The reaction was protected from light and stirred at room temperature for 20 h. The crude mixture of Compound 2g was divided into four portions and three of them were saved for surface modification reactions. One of four divided portions containing Compound 2g (1.74 mL, ca. 2.56 µmol) was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 37 cm×O.D. 3 cm, manufacturer: Bio-Rad) in DMF. The SEC fractions containing the product were combined, concentrated under reduced pressure, and dried extensively in vacuo to give 67.4 mg of Compound 2g.

$^1$H NMR (600 MHz, DMSO-$d_6$) δ 4.03 (m, 20.50H, $H_{6NP}$), 3.64-3.37 (m, 1540.16H, $H_{1NP}$, $H_{2NP}$, $H_{3NP}$, $H_{4NP}$, and $H_{5NP}$), 3.18-2.94 (m, 160.24H, $H_d$, $H_f$, $H_{fNP}$, $H_{gNP}$, $H_{fSn}$, and $H_{gSn}$), 2.80-2.59 (m, 127.48H, $H_b$ and $H_g$), 2.43 (m, 58.58H, $H_e$ and $H_a$), 2.19 (m, 120.70H, $H_c$), 1.51 (m, 12.58H, $H_{4sn}$), 1.28 (m, 11.47H, $H_{3Sn}$), 1.06 (m, 10.42H, $H_{2Sn}$), 0.84 (t, 15.50H, J=6.2 Hz, $H_{1Sn}$).

Step 3: Attachment of Ligand Moieties to the Azide End of PEG by Click Reaction [Preparation of Dendrimer Conjugate (1g)]

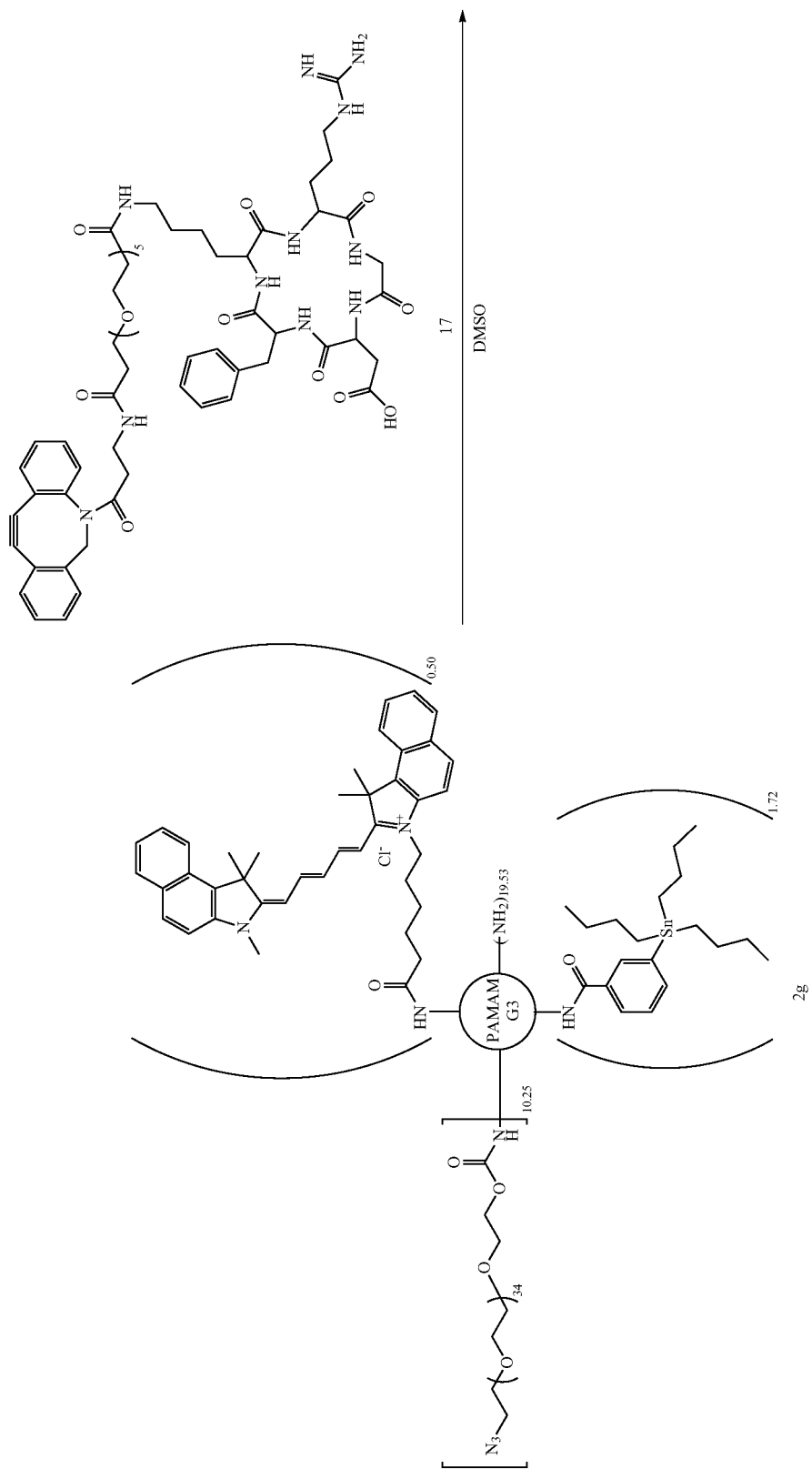

-continued
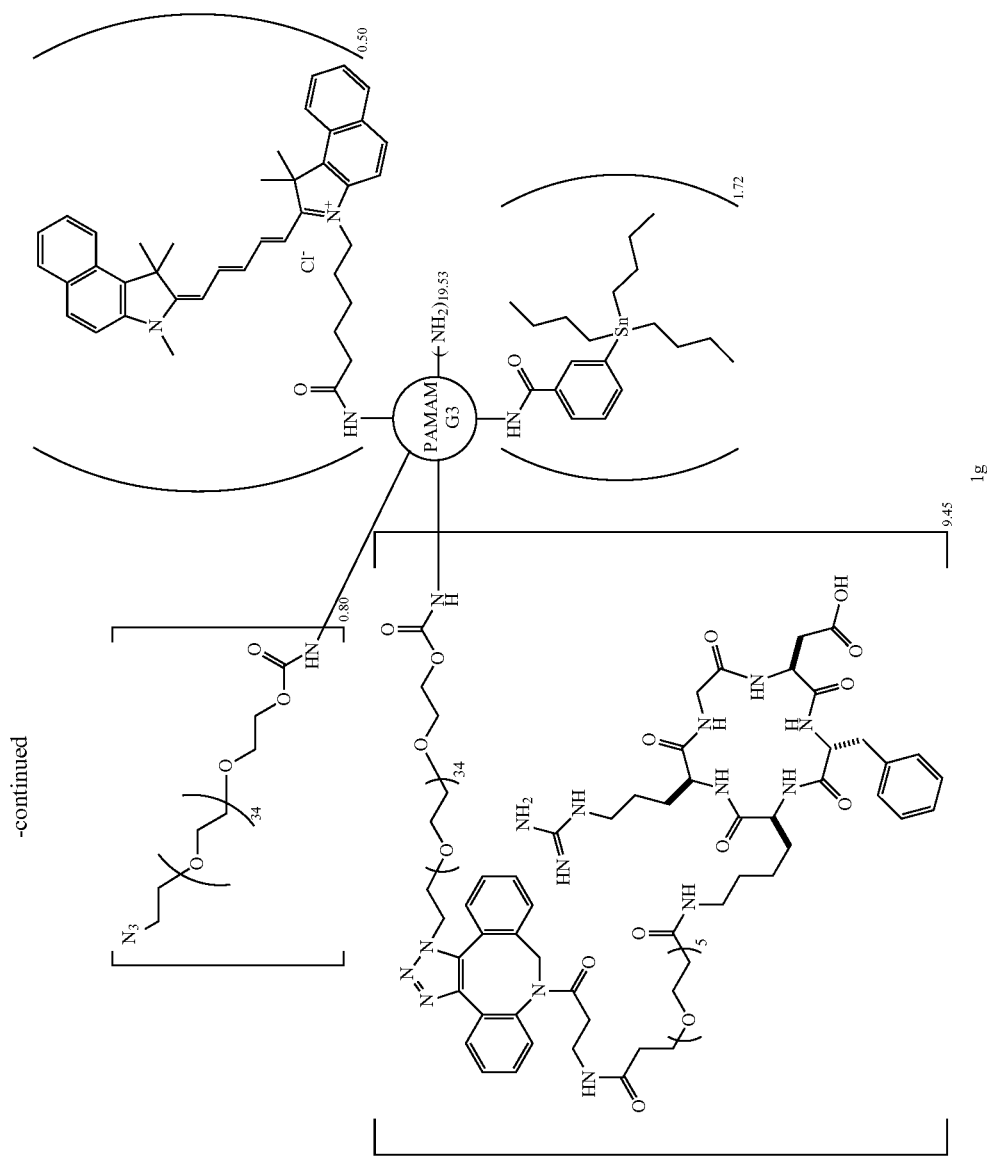
1g

-continued
1g
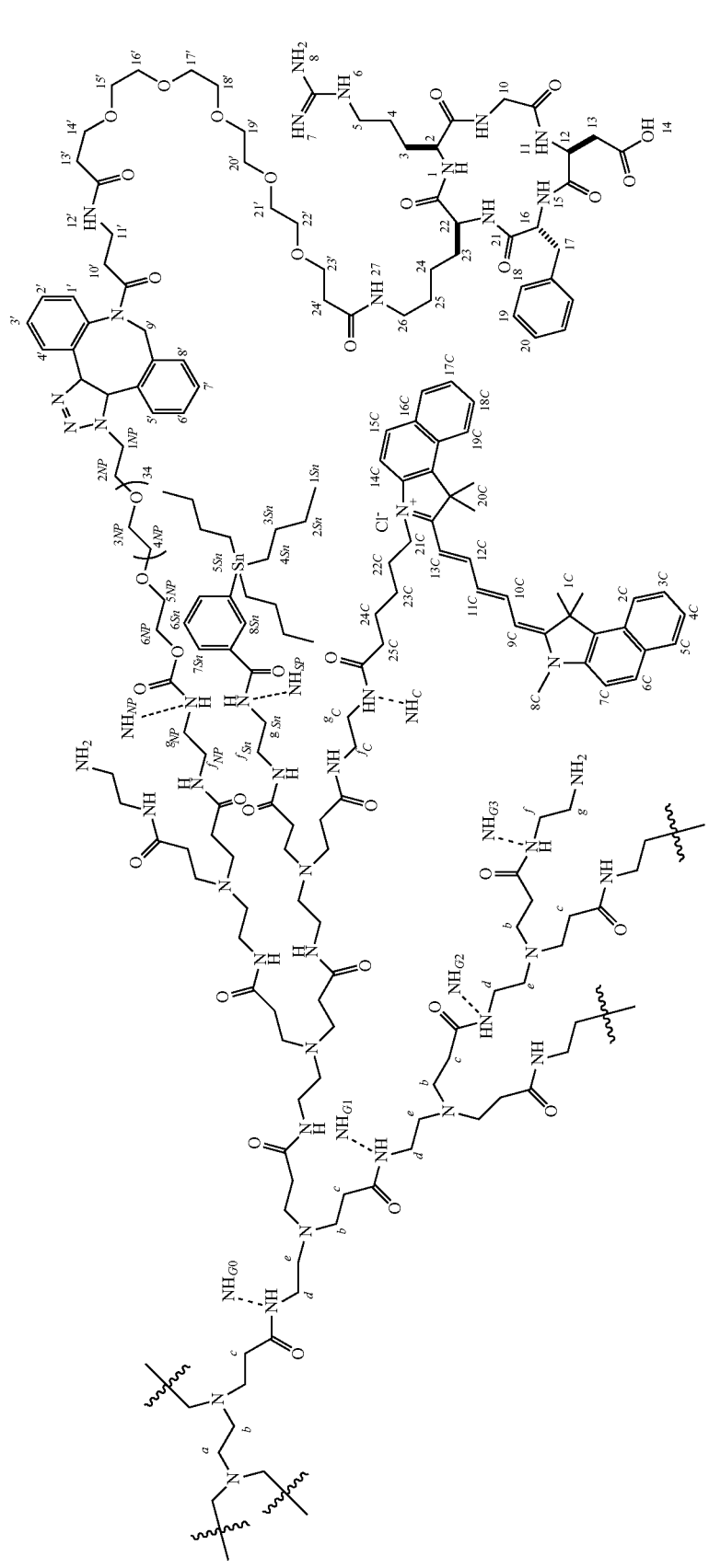

To a solution of Compound 2g (53.7 mg, 2.08 μmol) obtained in Step 2 in DMSO (1.2 mL) was added a solution of Compound 17 (32.0 mg, 27.1 μmol) obtained in Preparational Example 2 in DMSO (160 μL). The reaction was protected from light and stirred at room temperature for 66 h. In a dark room, the crude mixture was purified by a preparative SEC (model: Bio-Beads S-X1, H 37.5 cm×O.D. 3.0 cm, manufacturer: Bio-Rad) in DMF. The SEC fractions containing the product were combined and dried extensively in vacuo to give Compound 1g' (structure not shown). Unfortunately, the analysis of Compound 1g' by $^1$H NMR in DMSO-$d_6$ indicated only ca. 4.17 RGD moieties were attached out of ca. ten available azide groups of Compound 2g. In an attempt to bring the RGD attachment to completion, another round of click reaction was pursued by adding a solution of Compound 17 (34.0 mg, 28.8 μmol) obtained in Preparational Example 2 in DMSO-$d_6$ (580 μL) to the solution of Compound 1g' (ca. 2.08 μmol) in DMSO-$d_6$ (800 μL). The reaction was protected from light and stirred at room temperature for 24 h under a dry Ar atmosphere. In a dark room, the crude mixture was purified by SEC twice: Bio-Beads S-X1 (H 33.5 cm×O.D. 3 cm, manufacturer: Bio-Rad) in DMF and Sephadex LH-20 (H 39.5 cm×O.D. 3 cm) in methanol. The SEC fractions containing the product were combined, concentrated under reduced pressure, and dried extensively in vacuo to give 48.6 mg of Compound 1g.

$^1$H NMR (600 MHz, DMSO-$d_6$) δ 5.91, 4.48 (ABq, 9.63H, $H_9$'), 5.81, 4.45 (ABq, 9.63H, $H_9$'), 0.84 (m, 15.50H, J=6.2 Hz, $H_{1,Sn}$);

MS (MALDI-TOF, DHB matrix) $M_n$ 31227.02, $M_w$ 32764.19, PDI 1.05.

Example 8

Preparation of Dendrimer Conjugate (1h)

Step 1: Modification of the Residual Surface Groups [Preparation of Dendrimer Conjugate (2h)]

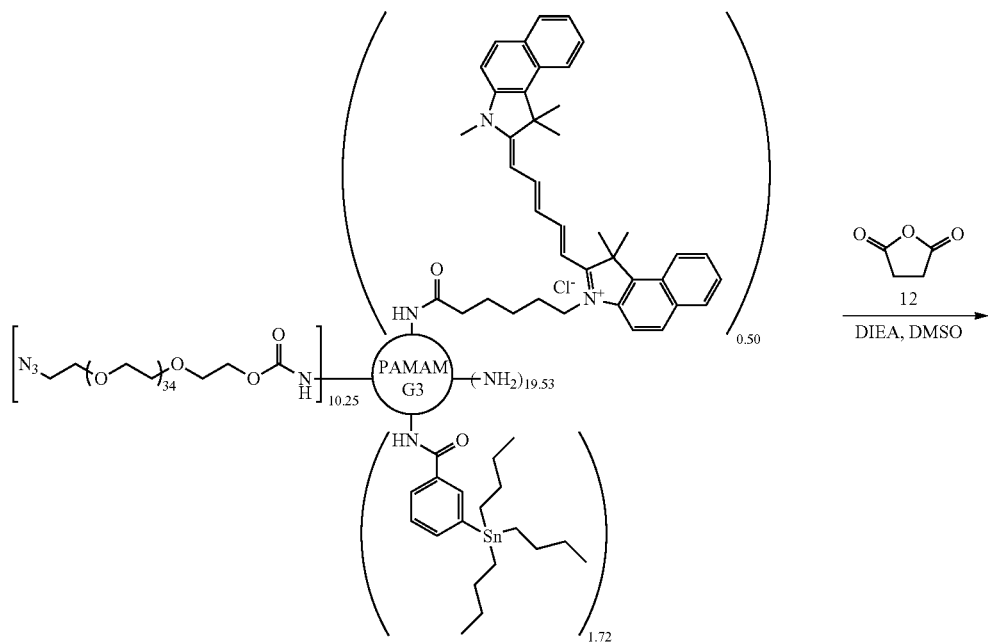

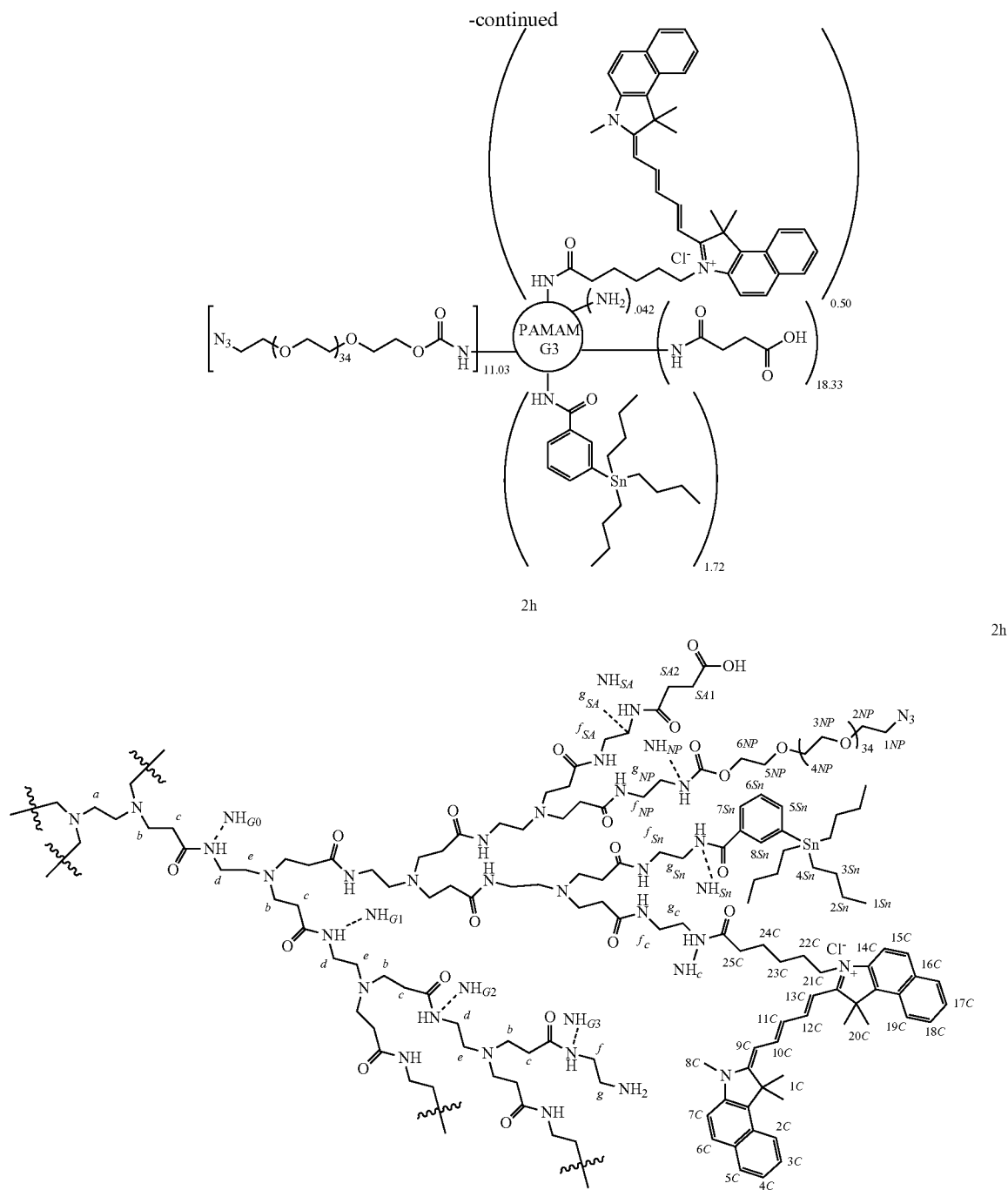

2h

To a portion of the crude reaction mixture of Compound 2g (1.74 mL, ca. 2.56 µmol) obtained in Step 2 of Example 7 were added succinic anhydride (Compound 12, 15.4 mg, 154 µmol) and DIEA (18.0 µL, 102 µmol). The reaction was protected from light and stirred at room temperature for 48 h under a dry Ar atmosphere. In a dark room, the crude mixture was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 39.0 cm×O.D. 3 cm, manufacturer: Bio-Rad) in DMF. The SEC fractions containing the product were combined, concentrated under reduced pressure, and dried extensively in vacuo to give 61.7 mg of Compound 2h.

$^1$H NMR (600 MHz, DMSO-d$_6$) δ 4.04 (m, 22.06H, H$_{6NP}$), 3.70-3.34 (m, 1638.38H, H$_{1NP}$, H$_{2NP}$, H$_{3NP}$, H$_{4NP}$, and H$_{5NP}$), 3.18-2.95 (m, 193.07H, H$_d$, H$_f$, H$_{fNP}$, H$_{gNP}$, H$_{fSn}$, H$_{gSn}$, H$_{fSA}$, and H$_{gSA}$), 2.80-2.57 (m, 121.76H, H$_b$ and H$_e$), 2.48-2.09 (m, 253.30H, H$_e$, H$_a$, H$_{SA2}$, H$_c$, and H$_{SA1}$), 1.51 (m, 12.00H, H$_{4Sn}$), 1.28 (m, 12.78H, H$_{3Sn}$), 1.06 (m, 10.14H, H$_{2Sn}$), 0.84 (t, 15.50H, J=6.7 Hz, H$_{1Sn}$).

Step 2: Attachment of Ligand Moieties to the Azide End of PEG by Click Reaction [Preparation of Dendrimer Conjugate (1h)]

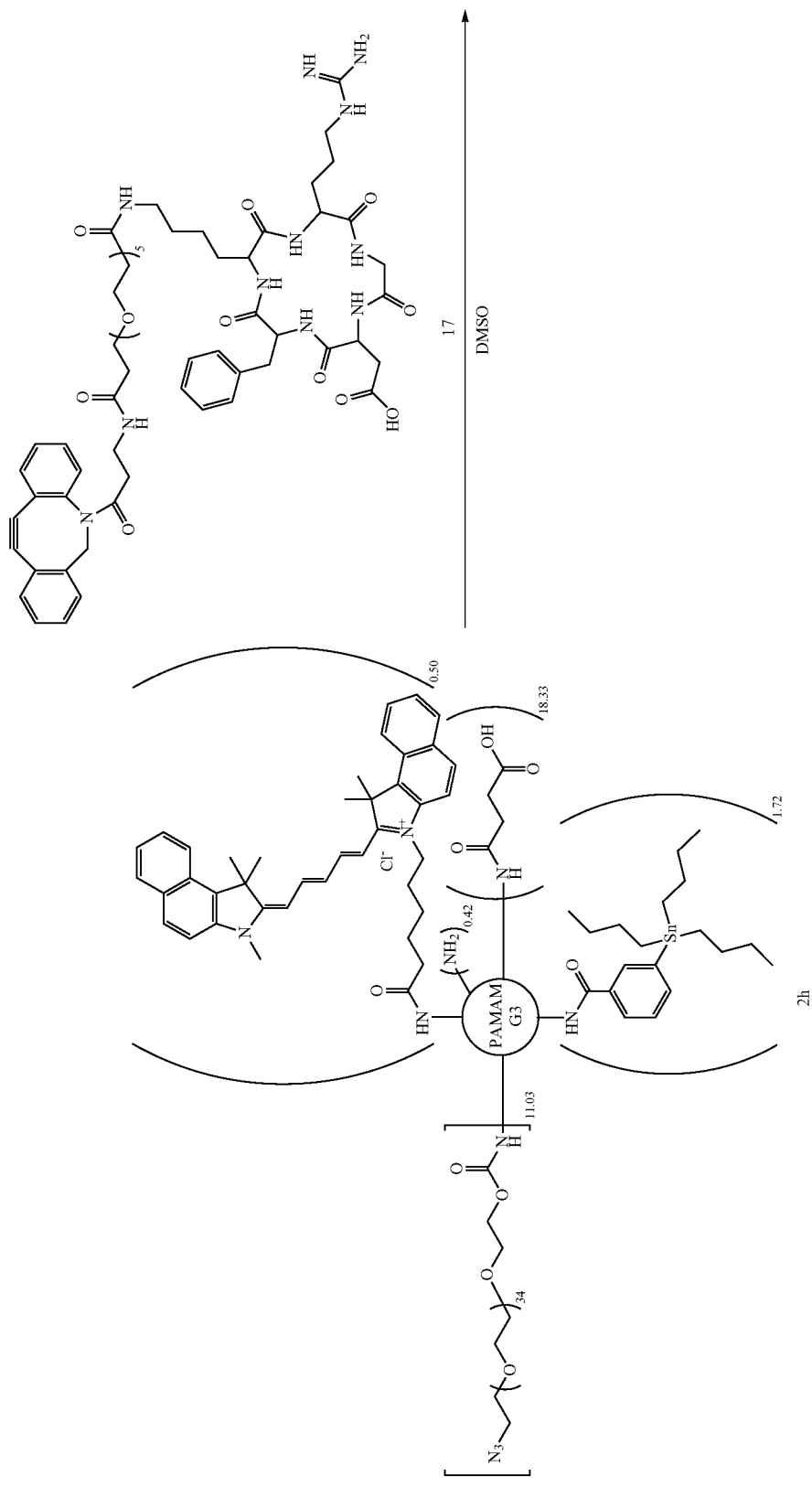

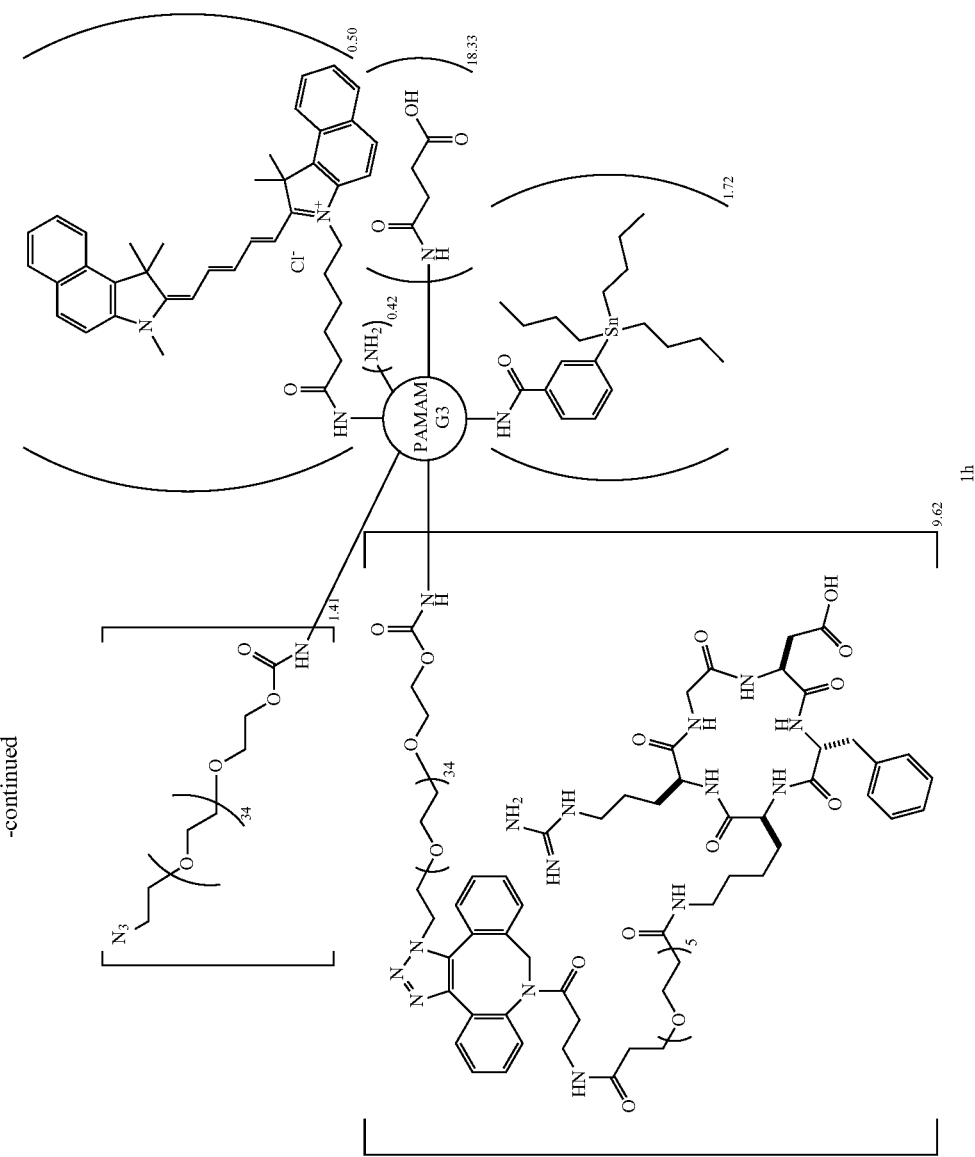

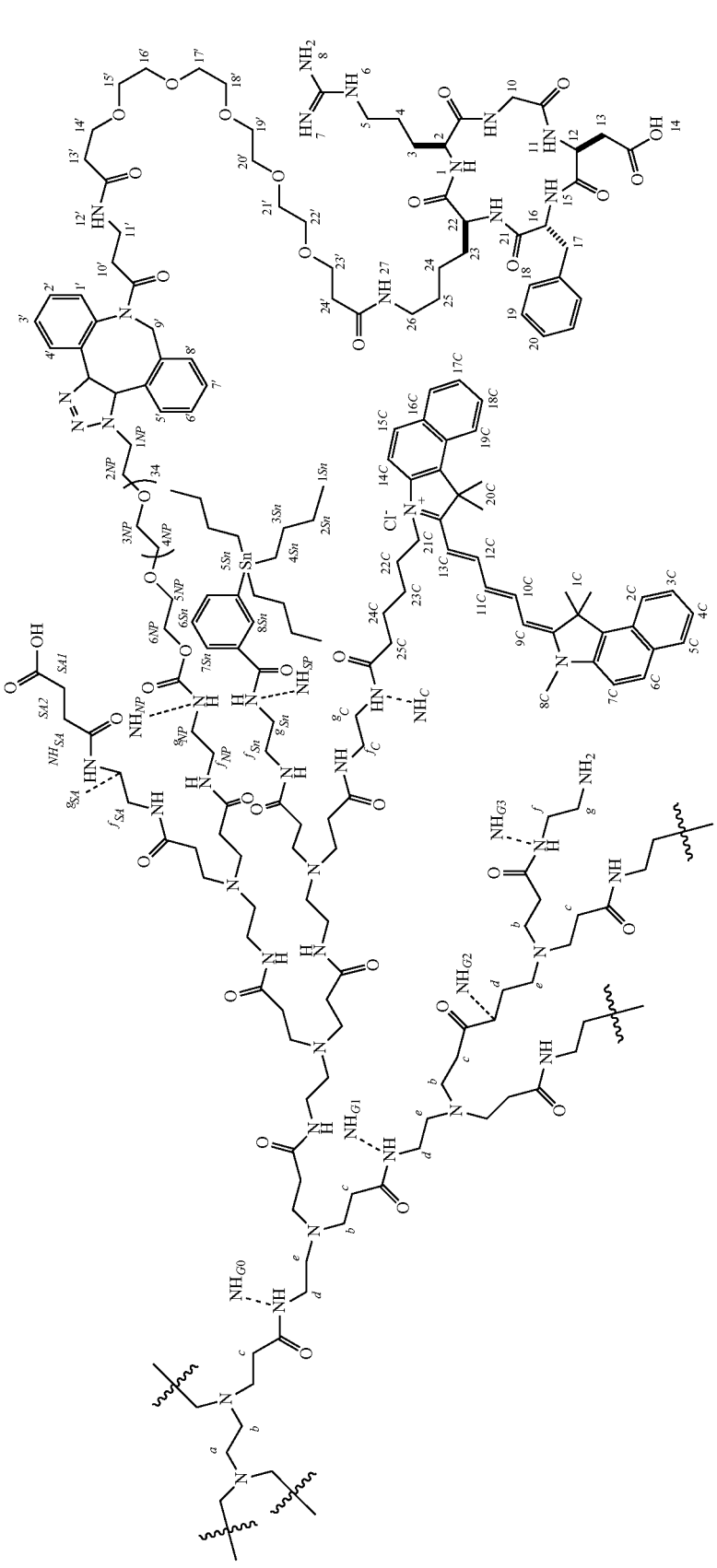
1h

To a solution of Compound 2h (51.19 mg, 1.91 μmol) obtained in Step 1 in DMSO (1.1 mL) was added a solution of Compound 17 (28.8 mg, 24.3 μmol) obtained in Preparational Example 2 in DMSO (150 μL). The reaction was protected from light and stirred at room temperature for 66 h. In a dark room, the crude mixture was purified by a preparative SEC (model: Bio-Beads S-X1, H 39 cm×O.D. 3 cm, manufacturer: Bio-Rad) in DMF. The SEC fractions containing the product were combined and dried extensively in vacuo to give Compound 1h' (structure not shown). Unfortunately, the analysis of Compound 1h' by $^1$H NMR in DMSO-$d_6$ indicated only ca. 4.05 RGD moieties were attached out of ca. 11 available azide groups of Compound 2h. In an attempt to bring the RGD attachment to completion, another round of click reaction was pursued by adding a solution of Compound 17 (31.7 mg, 26.8 μmol) obtained in Preparational Example 2 in DMSO-$d_6$ (500 μL) to the solution of Compound 1h' (ca. 1.91 μmol) in DMSO-$d_6$ (800 μL). The reaction was protected from light and stirred at room temperature for 24 h under a dry Ar atmosphere. In a dark room, the crude mixture was purified by SEC twice: Bio-Beads S-X1 (H 32.5 cm×O.D. 3 cm, manufacturer: Bio-Rad) in DMF and Sephadex LH-20 (H 39 cm×O.D. 3 cm) in methanol. The SEC fractions containing the product were combined, concentrated under reduced pressure, and dried extensively in vacuo to give 68.3 mg of Compound 1h.

$^1$H NMR (600 MHz, DMSO-$d_6$) δ 5.91, 4.48 (ABq, 9.62H, $H_{9'}$), 5.84, 4.45 (ABq, 9.62H, $H_{9'}$), 0.84 (m, 15.50H, J=6.7 Hz, $H_{1,Sn}$);

MS (MALDI-TOF, DHB matrix) $M_n$ 30635.72, $M_w$ 32879.84, PDI 1.07.

Example 9

Preparation of Dendrimer Conjugate (1i)

Step 1: Modification of the Residual Surface Groups [Preparation of Dendrimer Conjugate (2i)]

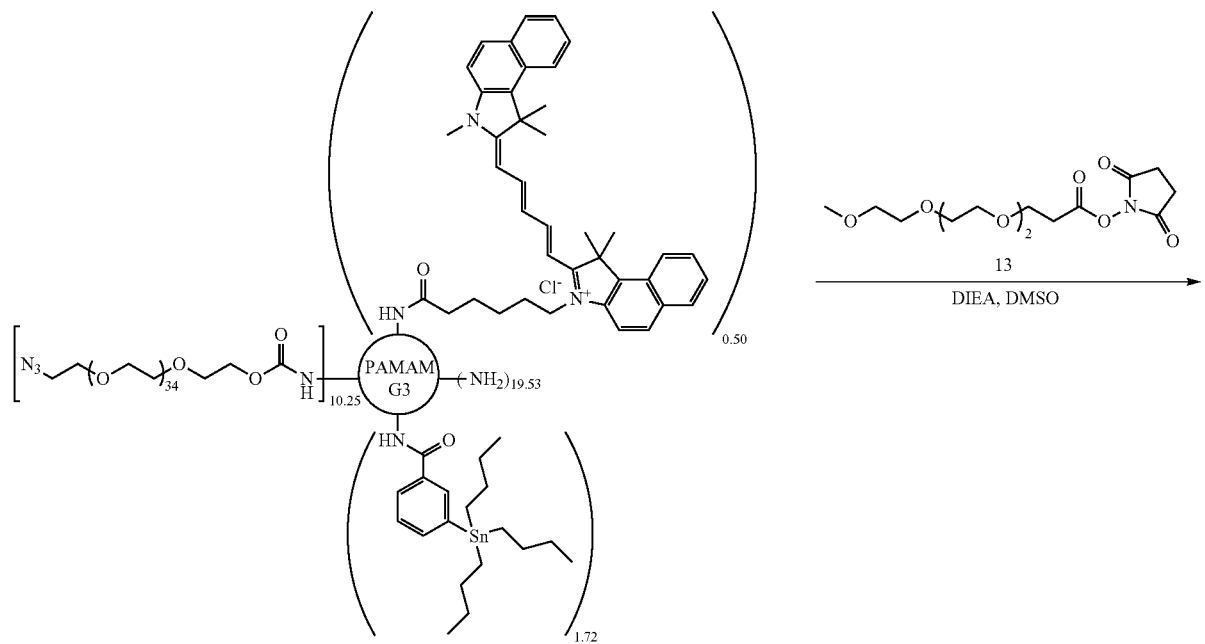

2g

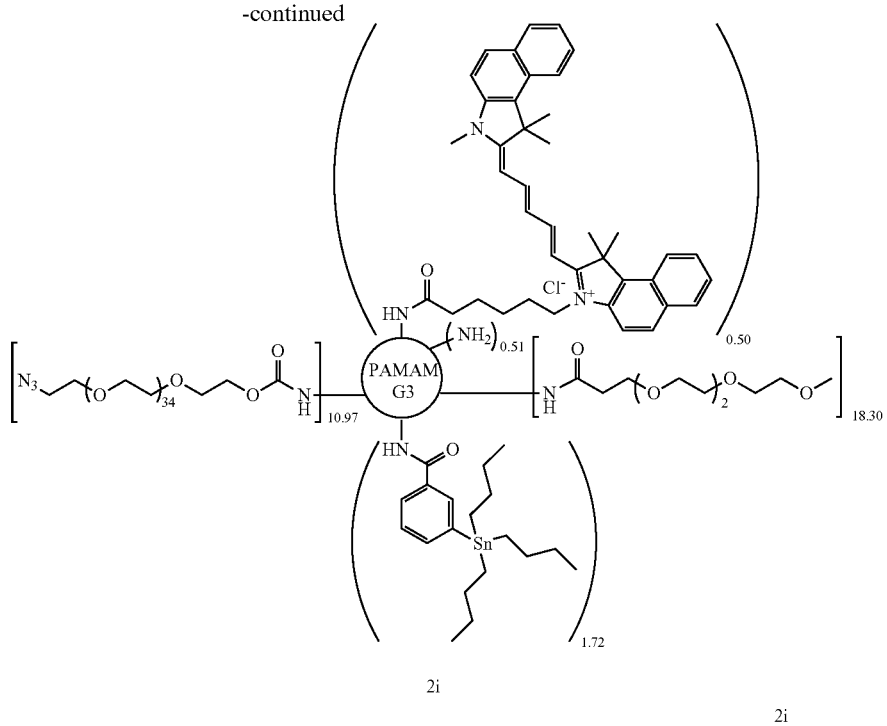

2i

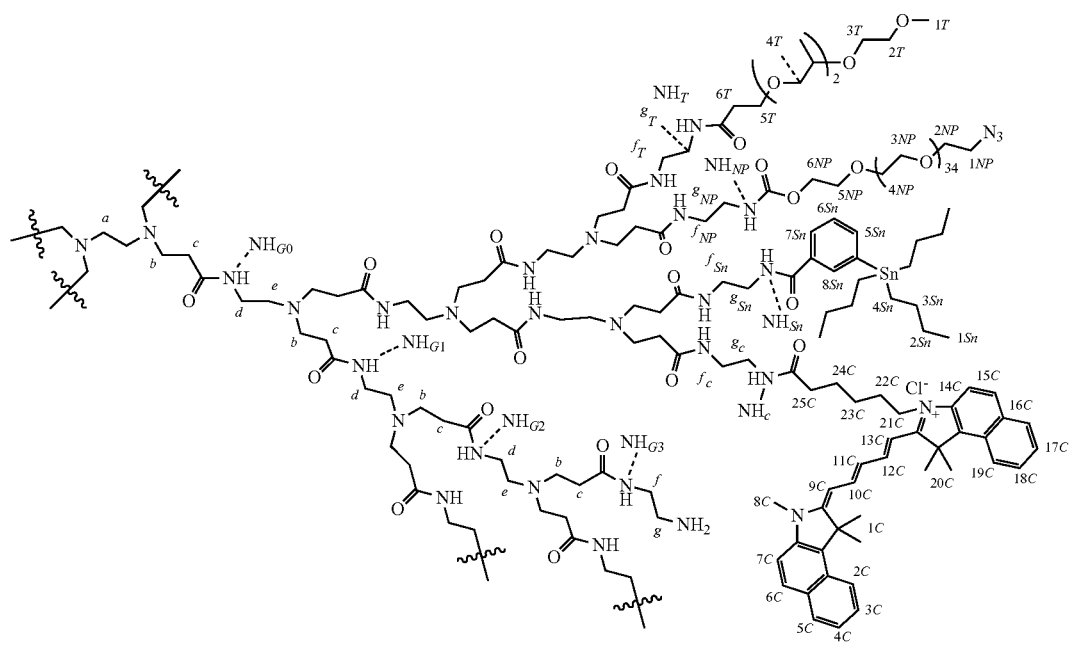

2i

To a portion of the crude reaction mixture of Compound 2g (2.60 mL, ca. 3.84 µmol) obtained in Step 2 of Example 7 was added a solution of m-dPEG$_4$-NHS ester (Compound 13, 76.7 mg, 230 µmol) in DMSO-d$_6$ (180 µL) followed by DIEA (26.7 µL, 154 µmol). The reaction was protected from light and stirred at room temperature for 48 h under a dry Ar atmosphere. In a dark room, the crude mixture was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 40.5 cm×O.D. 4.5 cm, manufacturer: Bio-Rad) in DMF. The SEC fractions containing the product were combined, concentrated under reduced pressure, and dried extensively in vacuo to give 102.1 mg of Compound 2i.

$^1$H NMR (600 MHz, DMSO-d$_6$) δ 4.03 (m, 21.86H, H$_{6NP}$), 3.65-3.36 (m, 1831.05H, H$_{1NP}$, H$_{2NP}$, H$_{3NP}$, H$_{4NP}$, H$_{5NP}$, H$_{2T}$, H$_{3T}$, H$_{4T}$, and H$_{5T}$), 3.23 (s, 56.31H, H$_{1T}$), 3.16-2.97 (m, 181.17H, H$_d$, H$_f$, H$_{fNP}$, H$_{gNP}$, H$_{fSn}$, H$_{gSn}$, H$_{fT}$, and H$_{gT}$), 2.71-2.57 (m, 120.10H, H$_b$ and H$_g$), 2.42 (m, 60.63H, H$_e$ and H$_a$), 2.45-2.10 (m, 162.36H, H$_c$ and H$_{6T}$), 1.50 (m, 13.17H, H$_{4Sn}$), 1.28 (m, 10.85H, H$_{3Sn}$), 1.06 (m, 11.28H, H$_{2Sn}$), 0.84 (t, 15.50H, J=6.7 Hz, H$_{1Sn}$).

Step 2: Attachment of Ligand Moieties to the Azide End of PEG by Click Reaction [Preparation of Dendrimer Conjugate (1i)]

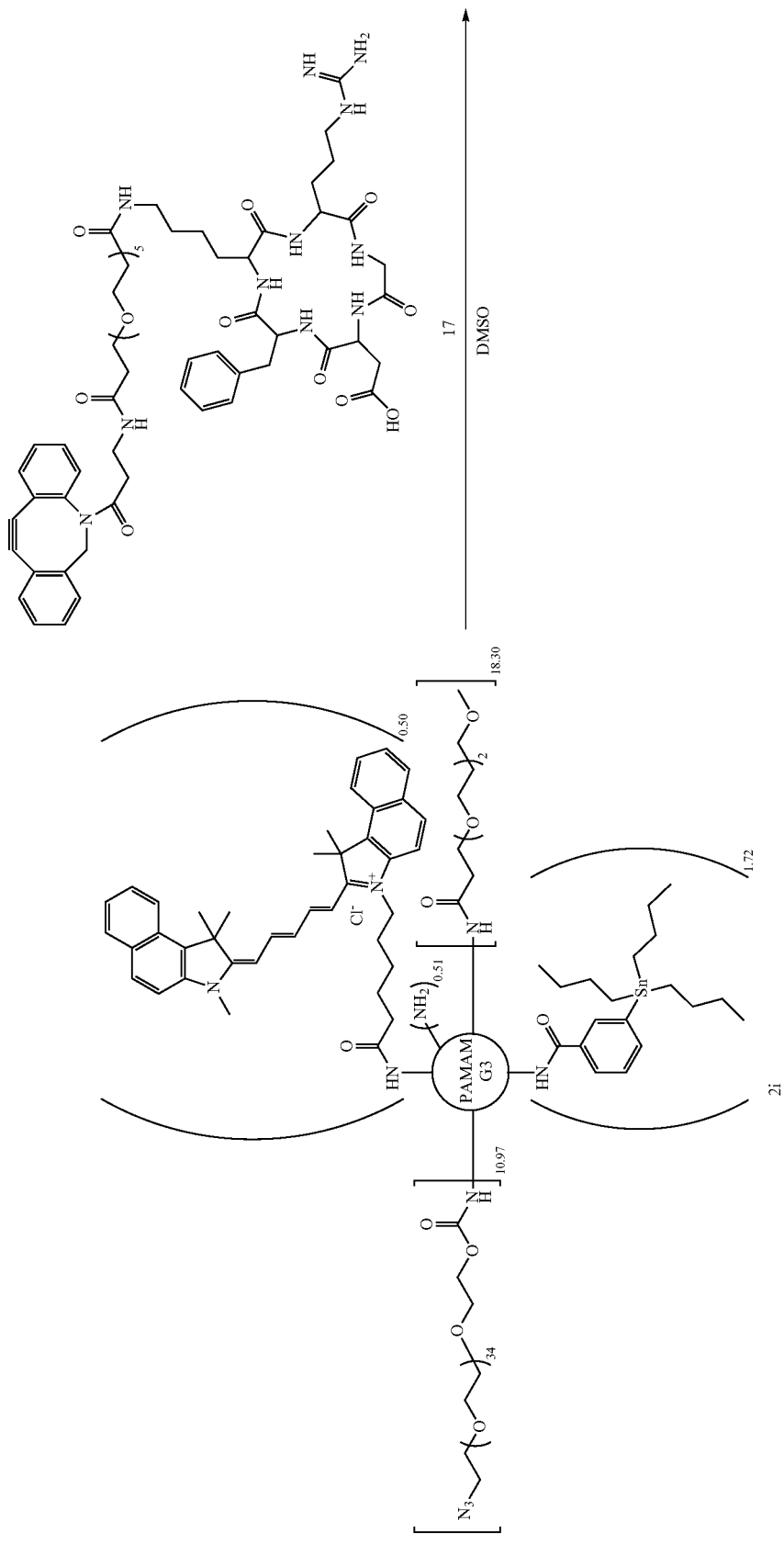

-continued
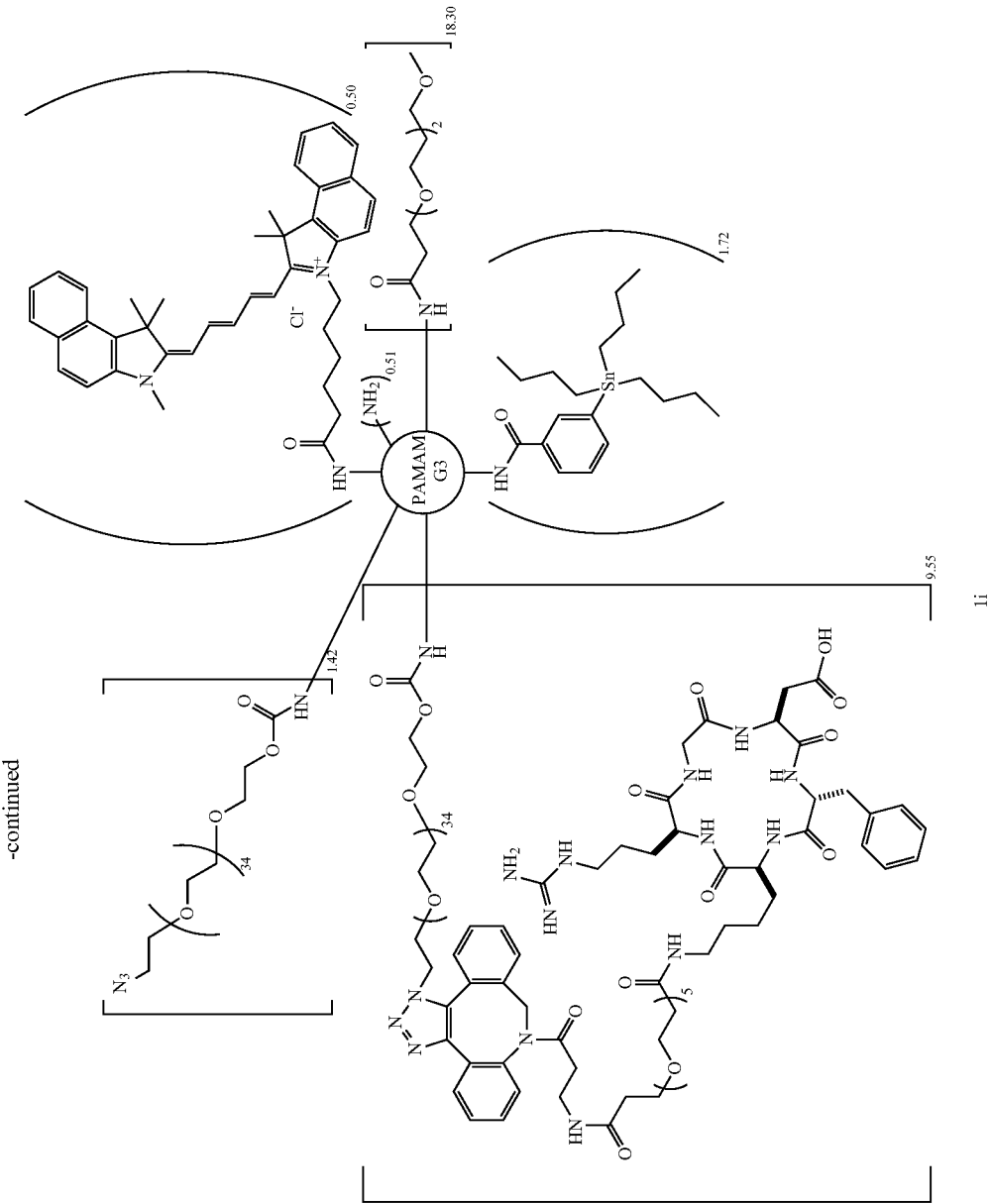
1i

1i
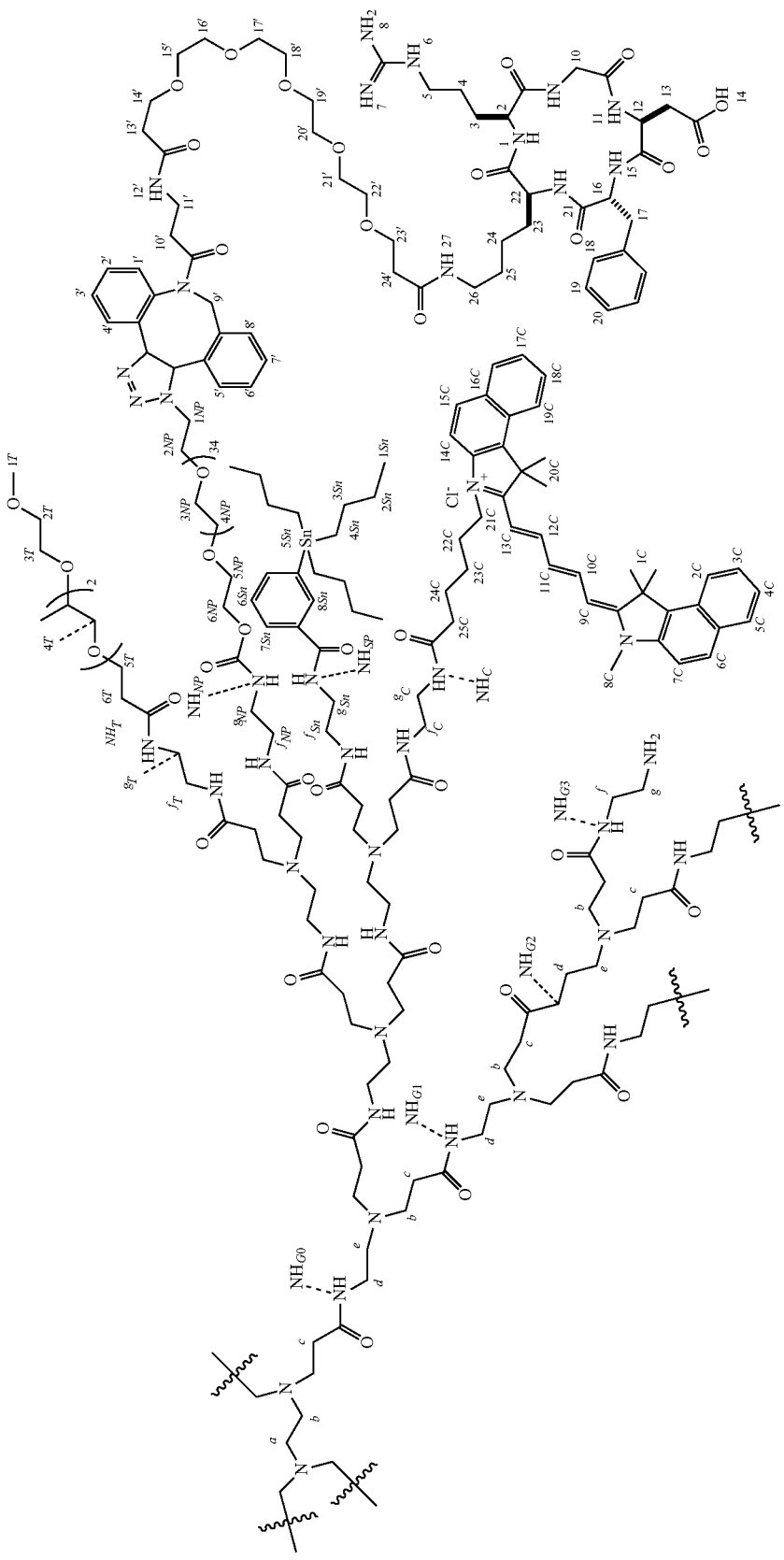

To a solution of Compound 2i (92.9 mg, 3.15 μmol) obtained in Step 1 in DMSO (1.8 mL) was added a solution of Compound 17 (47.3 mg, 40.0 μmol) obtained in Preparational Example 2 in DMSO (240 μL). The reaction was protected from light and stirred at room temperature for 66 h. In a dark room, the crude mixture was purified by a preparative SEC (model: Bio-Beads S-X1, H 41.5 cm×O.D. 4.5 cm, manufacturer: Bio-Rad) in DMF. The SEC fractions containing the product were combined and dried extensively in vacuo to give Compound 1i' (structure not shown). Unfortunately, the analysis of Compound 1i' by $^1$H NMR in DMSO-$d_6$ indicated only ca. 3.90 RGD moieties were attached out of ca. 11 available azide groups of Compound 2i. In an attempt to bring the RGD attachment to completion, another round of click reaction was pursued by adding a solution of Compound 17 (35.9 mg, 30.4 μmol) obtained in Preparational Example 2 in DMSO-$d_6$ (1.1 mL) to the solution of Compound 1i' (ca. 3.15 μmol) in DMSO-$d_6$ (1.0 mL). The reaction was protected from light and stirred at room temperature for 48 h under a dry Ar atmosphere. In a dark room, the crude mixture was purified by SEC twice: Bio-Beads S-X1 (H 31.5 cm×O.D. 4.5 cm, manufacturer: Bio-Rad) in DMF and Sephadex LH-20 (H 38.5 cm×O.D. 4.5 cm) in methanol. The SEC fractions containing the product were combined, concentrated under reduced pressure, and dried extensively in vacuo to give 99.7 mg of Compound 1i.

$^1$H NMR (600 MHz, DMSO-$d_6$) δ 5.91, 4.48 (ABq, 9.55H, $H_{9'}$), 5.81, 4.45 (ABq, 9.55H, $H_{9'}$), 0.84 (m, 15.50H, J=6.7 Hz, $H_{1,Sn}$);

MS (MALDI-TOF, DHB matrix) $M_n$ 29797.73, $M_w$ 31372.41, PDI 1.05.

Example 10

Preparation of Dendrimer Conjugate (1j)

Step 1: Modification of the Residual Surface Groups [Preparation of Dendrimer Conjugate (2j)]

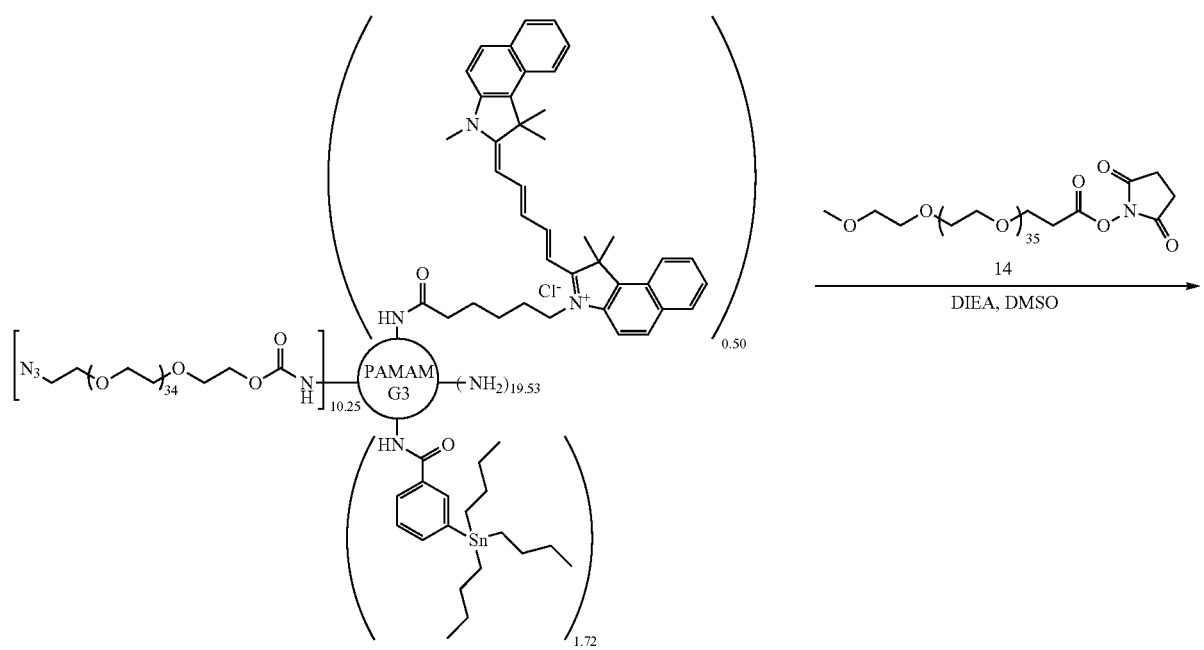

2g

-continued

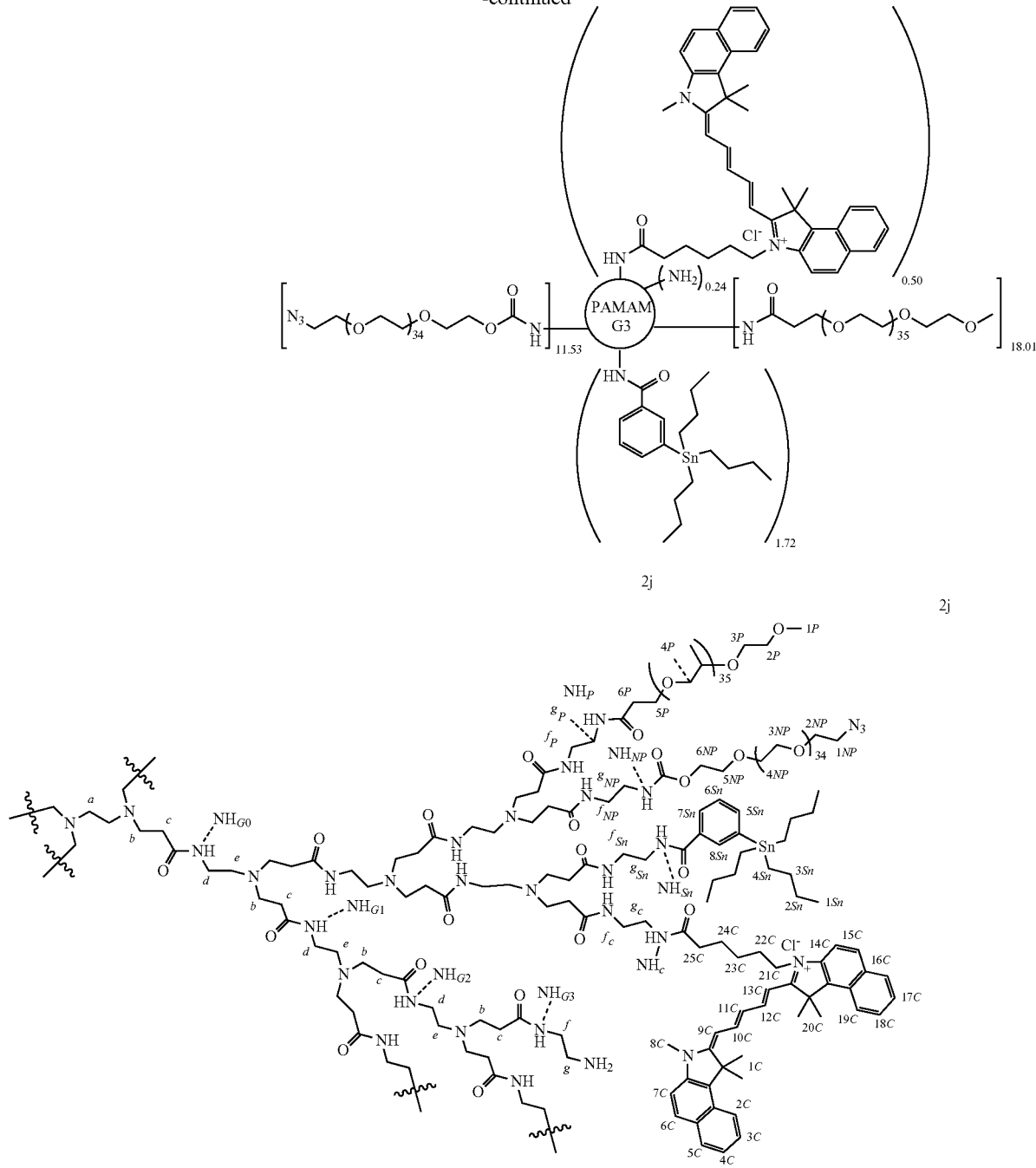

2j

2j

To a portion of the crude reaction mixture of Compound 2g (1.74 mL, ca. 2.56 μmol) obtained in Step 2 of Example 7 was added m-dPEG$_{37}$-NHS ester (Compound 14, 182 mg, 102 μmol) followed by DIEA (18.0 μL, 102 μmol). The reaction was protected from light and stirred at room temperature for 48 h under a dry Ar atmosphere. In a dark room, the crude mixture was first filtered through a short SEC column (model: Bio-Beads S-X1, H 5 cm×O.D. 0.7 cm, manufacturer: Bio-Rad) in DMF, and then purified by a preparative SEC (model: Bio-Beads S-X1, H 41.0 cm×O.D. 4.5 cm, manufacturer: Bio-Rad) in DMF. The SEC fractions containing the product were combined, concentrated under reduced pressure, and dried extensively in vacuo to give 107 mg of Compound 2j.

$^1$H NMR (600 MHz, DMSO-d$_6$) δ 4.03 (m, 24.3H, H$_{6NP}$), 3.64-3.36 (m, 3779.64H, H$_{1NP}$, H$_{2NP}$, H$_{3NP}$, H$_{4NP}$, H$_{5NP}$, H$_{2P}$, H$_{3P}$, H$_{4P}$, and H$_{5P}$), 3.24 (s, 54.34H, H$_{1P}$), 3.16-2.96 (m, 174.72H, H$_d$, H$_f$, H$_{fNP}$, H$_{gNP}$, H$_{fSn}$, H$_{gSn}$, H$_{fP}$, and H$_{gP}$), 2.79-2.54 (m, 120.00H, H$_b$ and H$_g$), 2.42 (m, 61.45H, H$_e$ and H$_a$), 2.35-2.09 (m, 155.82H, H$_c$ and H$_{6P}$), 1.50 (m, 12.03H, H$_{4Sn}$), 1.28 (m, 11.13H, H$_{3Sn}$), 1.06 (m, 10.60H, H$_{2Sn}$), 0.84 (t, 15.50H, J=6.7 Hz, H$_{1Sn}$).

Step 2: Attachment of Ligand Moieties to the Azide End of PEG by Click Reaction [Preparation of Dendrimer Conjugate (1j)]

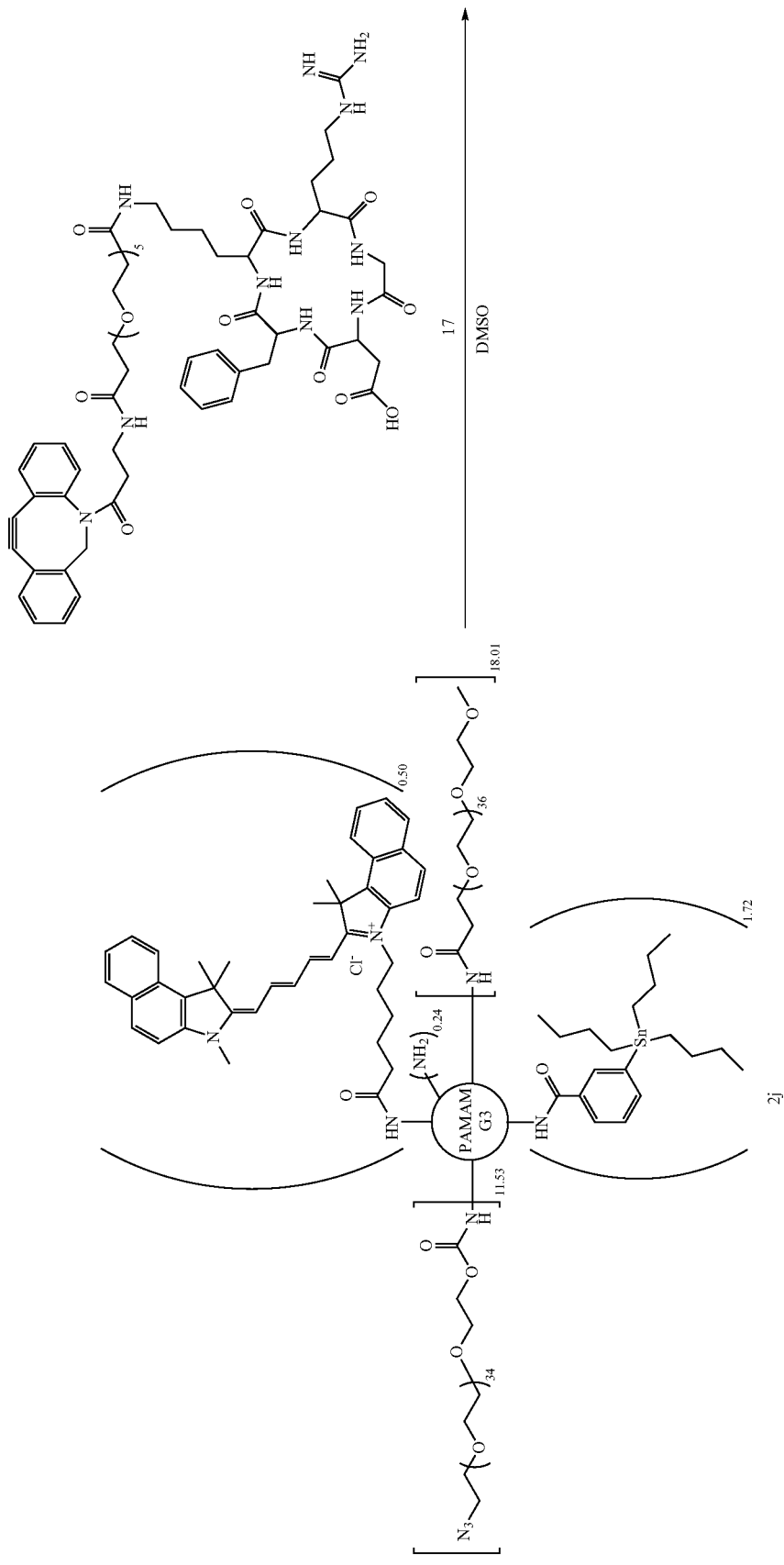

-continued
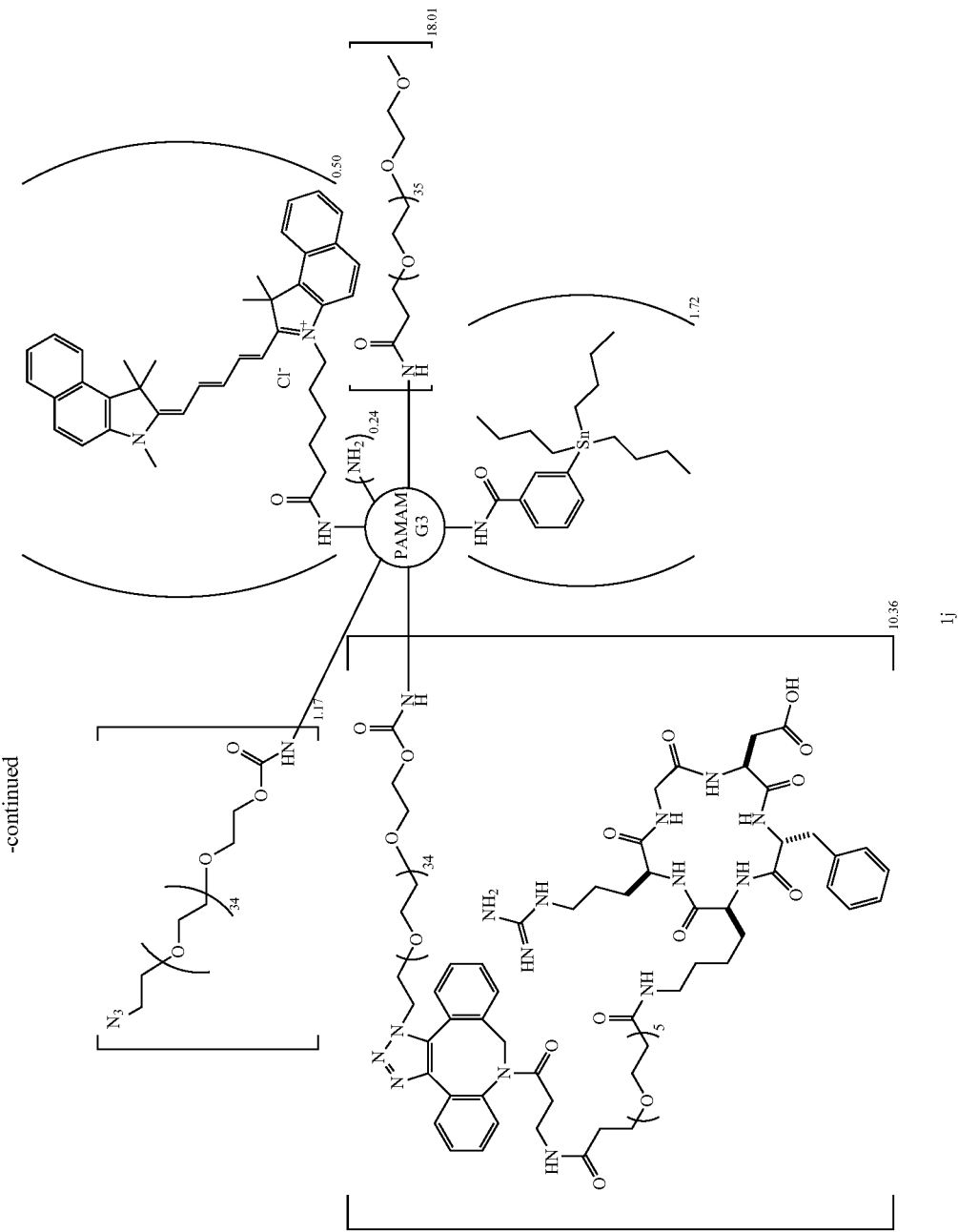

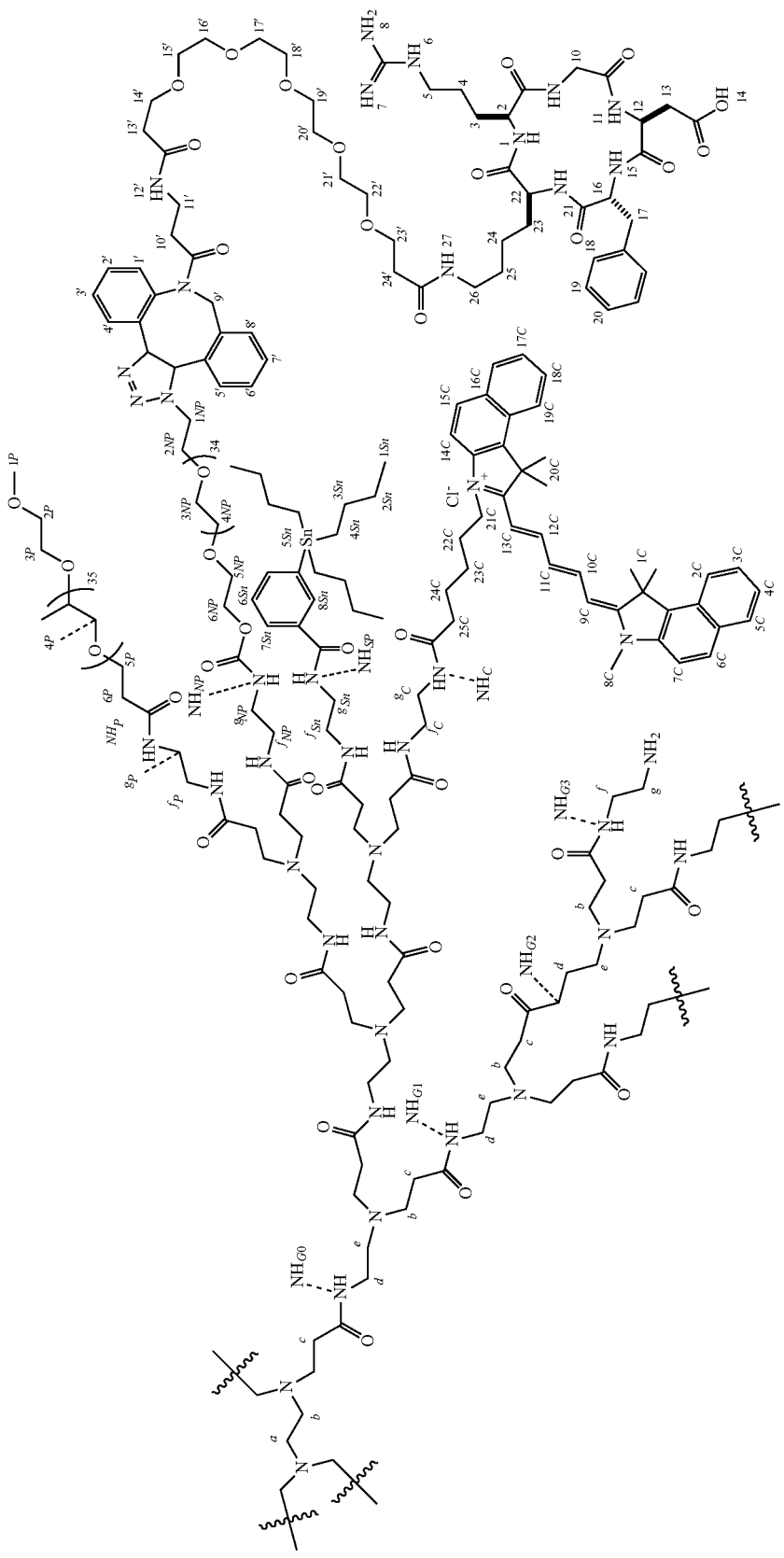

To a solution of Compound 2j (81.4 mg, 1.97 μmol) obtained in Step 1 in DMSO (1.1 mL) was added a solution of Compound 17 (29.9 mg, 25.3 μmol) obtained in Preparational Example 2 in DMSO (150 μL). The reaction was protected from light and stirred at room temperature for 66 h. In a dark room, the crude mixture was purified by a preparative SEC (model: Bio-Beads S-X1, H 41.5 cm×O.D. 4.5 cm, manufacturer: Bio-Rad) in DMF. The SEC fractions containing the product were combined and dried extensively in vacuo to give Compound 1j' (structure not shown). Unfortunately, the analysis of Compound 1j' by $^1$H NMR in DMSO-$d_6$ indicated only ca. 6.88 RGD moieties were attached out of ca. 11 available azide groups of Compound 2j. In an attempt to bring the RGD attachment to completion, another round of click reaction was pursued by adding a solution of Compound 17 (21.7 mg, 18.4 μmol) obtained in Preparational Example 2 in DMSO-$d_6$ (370 μL) to the solution of Compound 1j' (ca. 1.97 μmol) in DMSO-$d_6$ (900 μL). The reaction was protected from light and stirred at room temperature for 48 h under a dry Ar atmosphere. In a dark room, the crude mixture was purified by SEC twice: Bio-Beads S-X1 (H 39.5 cm×O.D. 4.5 cm, manufacturer: Bio-Rad) in DMF and Sephadex LH-20 (H 39 cm×O.D. 4.5 cm) in methanol. The SEC fractions containing the product were combined, concentrated under reduced pressure, and dried extensively in vacuo to give 90.2 mg of Compound 1j.

$^1$H NMR (600 MHz, DMSO-$d_6$) δ 5.90, 4.48 (ABq, 11.53H, $H_{9'}$), 5.84, 4.45 (ABq, 11.53H, $H_{9'}$), 0.84 (m, 15.50H, J=6.2 Hz, $H_{1Sn}$)

MS (MALDI-TOF, DHB matrix) $M_n$ 52145.01, $M_w$ 54101.22, PDI 1.04.

Experimental Example 1

Cytotoxicity Assays

Human malignant glioma U87MG cell line was obtained from American Type Culture Collection (ATCC) and cultured in Minimum Essential Medium (MEM) with 10% fetal bovine serum (FBS), 100 U/mL penicillin, and 100 μg/mL streptomycin at 37° C. in a humidified atmosphere containing 5% $CO_2$.

The 600 μM stock solutions of RGD-attached dendrimer conjugate Compounds 1a-1j obtained in Examples 1-10 in deionized water were diluted serially with MEM to prepare samples of the following concentrations: $10^{-10}$, $10^{-9}$, $10^{-8}$, $10^{-7}$, and $10^{-6}$ M. U87MG cells were seeded in three flat-bottomed 96-well microculture plates each at a density of 5×$10^3$ cells per well (for 24 h incubation), 2×$10^3$ cells per well (for 48 h incubation), or 1×$10^3$ cells per well (for 72 h incubation). Each well was filled with 100 μL of culture media and the plates were incubated for 24 h at 37° C. to allow cell attachment. Next, cells were treated with 100 μL of either each dilution or MEM (as a control) per well and placed in a humidified incubator at 37° C. with 5% $CO_2$ for 24, 48, or 72 h. The formulations were removed and the cells were quickly rinsed with Dulbecco's Phosphate-Buffered Saline (DPBS) once. Cells were then treated with an aqueous mixture (total volume: 110 μL) of 100 μL of fresh MEM and 10 μL of Cell Counting Kit-8 (CCK-8, purchased from Dojindo) per well, and incubated for additional 2 h. The absorbance values at 450 nm, which are proportional to the numbers of live cells, were measured and normalized against those of the controls (i.e., 100%) prepared under the same conditions to determine the cell viability. All experiments were repeated twice in triplicates, and the results are shown as the mean±standard deviation (SD) in FIG. 3.

Figure 3:
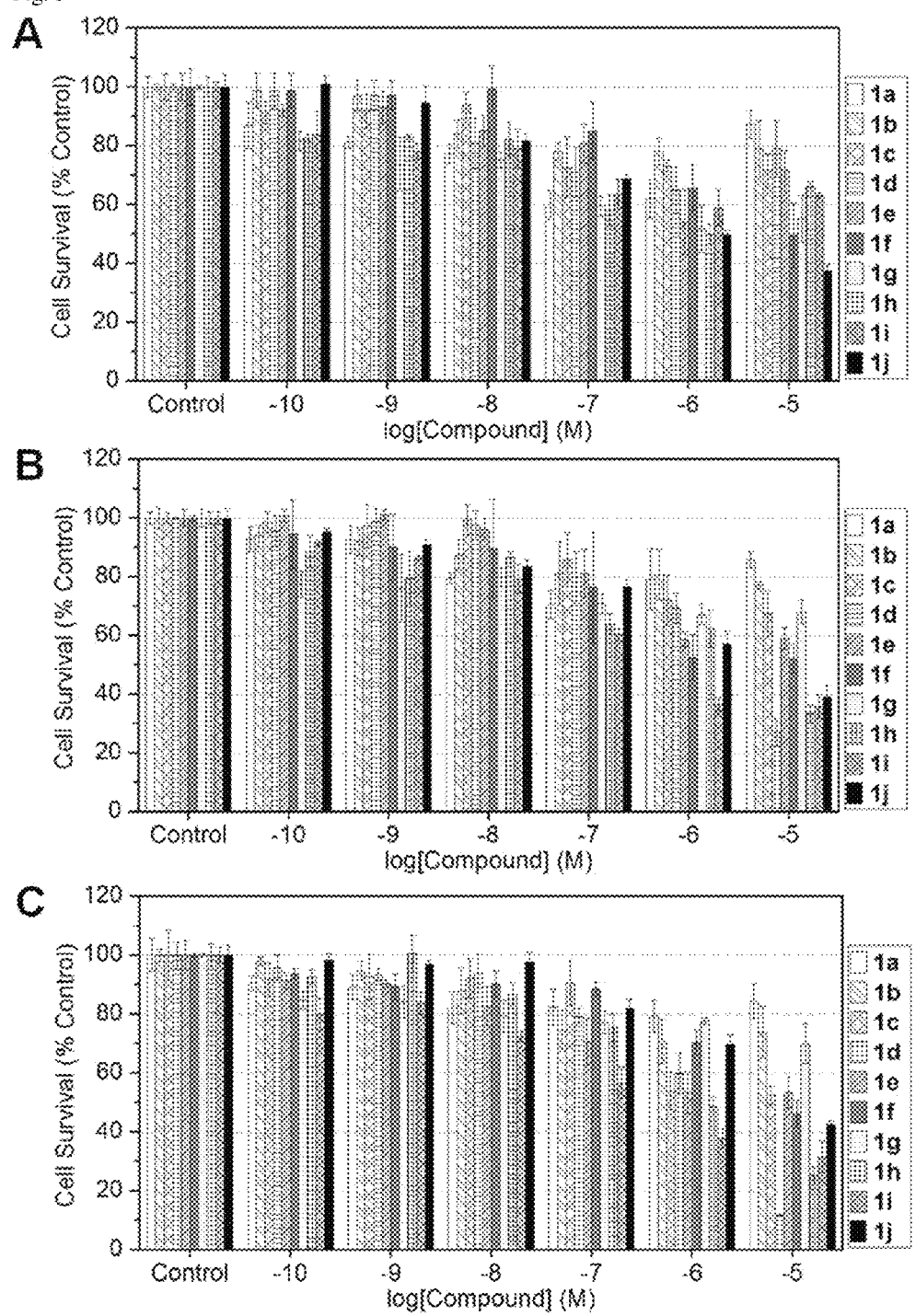
FIG. 3 illustrates the graphs of concentration-dependent cytotoxicity assay results of multivalent ligands according to the present invention (A: 24 h incubation, B: 48 h incubation, C: 72 h incubation).

As illustrated in FIG. 3, multivalent ligands according to the present invention exhibited high cell survival rates of ca. 80-100% at the concentration of $10^{-10}$, $10^{-9}$, and $10^{-8}$ M and ca. 40-80% at the concentration of $10^{-7}$, $10^{-6}$, and $10^{-5}$ M. Also, multivalent ligands according to the present invention showed relatively high cell survival rates when they were incubated with cells for 24, 48, or 72 h. Thus, the cytotoxicity of multivalent ligands 1a-1j is relatively low.

Therefore, multivalent ligands according to the present invention could be used as active ingredients for tumor diagnosis because of their excellent safety upon administration in vivo as demonstrated by the relatively low cytotoxicity.

Experimental Example 2

In Vitro Competitive Binding Assays

In order to determine the relative binding affinity of multivalent RGD-attached ligands according to the present invention at the $α_vβ_3$ integrin receptor by competition with the radiolabeled [$^{125}$I]echistatin ($α_vβ_3$ integrin-specific, purchased from PerkinElmer), the following experiments were performed.

Specifically, U87MG cells were harvested and seeded in 24-well plates at a density of 1×$10^5$ cells per well, each well was filled with 200 μL of media, and the cells were incubated overnight at 37° C. to allow cell attachment. The 600 μM stock solutions of RGD-attached dendrimer conjugate Compounds 1a-1j obtained in Examples 1-10, their synthetic precursor Compounds 2a-2j without the RGD ligands, and c(RGDfK) Compound 16 used in the Preparational Example 2 as a monovalent control in deionized water were diluted serially with Hank's balanced salt solution (HBSS, purchased from Gibco) to prepare samples of different concentrations ranging from 2.4×$10^{-14}$ to 2.4×$10^{-5}$ M. Cells were treated immediately with 200 μL of each warmed dilution per well and incubated for 30 min at 37° C. Subsequently, 50 μL of [$^{125}$I]echistatin diluted with HBSS was additionally added to each well (all fixed at 37 Bq per well) and the cells were placed in a shaking incubator at 37° C. for 60 min. Cells were then washed twice with cold HBSS, and 0.5 mL of 1% SDS was added to each well to facilitate cell lysis. The lysates were collected from each well and the radioactivity was measured in a gamma counter (Cobra gamma counter, purchased from Packard). The radioactivity value was normalized against the amount of protein included in each sample. The inhibitory concentrations of dendrimer conjugate Compounds 1a-1j obtained in Examples 1-10 that reduced the specific binding of [$^{125}$I]echistatin at $α_vβ_3$ integrin by 50% ($IC_{50}$) were calculated by the nonlinear regression analysis (sigmoidal dose response equation) using the Prism 5.0 software (purchased from GraphPad). All experiments were repeated twice in triplicates, and the results are shown as the mean±SD in the following Table 1 and FIG. 4.

TABLE 1

| Example (Dendrimer Conjugate) | No. of RGD units | H/L | Surface Functionality of the Core | $IC_{50}$ (M) |
|---|---|---|---|---|
| 1 (Compound 1a) | 3.82 | L | amine | 2.945 × $10^{-9}$ |
| 2 (Compound 1b) | 4.11 | L | acetyl & amine | 3.354 × $10^{-8}$ |
| 3 (Compound 1c) | 4.34 | L | acetyl | 2.948 × $10^{-7}$ |

TABLE 1-continued

| Example (Dendrimer Conjugate) | No. of RGD units | H/L | Surface Functionality of the Core | IC$_{50}$ (M) |
|---|---|---|---|---|
| 4 (Compound 1d) | 4.24 | L | succinine acid | $5.376 \times 10^{-7}$ |
| 5 (Compound 1e) | 4.42 | L | TEG | $3.957 \times 10^{-7}$ |
| 6 (Compound 1f) | 3.89 | L | PEG | $4.051 \times 10^{-7}$ |
| 7 (Compound 1g) | 9.45 | H | amine | $3.767 \times 10^{-10}$ |
| 8 (Compound 1h) | 9.62 | H | succinine acid | $3.409 \times 10^{-7}$ |
| 9 (Compound 1i) | 9.55 | H | TEG | $3.835 \times 10^{-7}$ |
| 10 (Compound 1j) | 10.36 | H | PEG | $4.397 \times 10^{-7}$ |
| c(RGDfK) (Compound 16) | 1 | — | — | $4.219 \times 10^{-6}$ |

(In the above Table 1, the number of RGD units was estimated by the analysis of $^1$H NMR integration, H stands for high-avidity ligand, L stands for low-avidity ligand, TEG stands for tetra(ethylene glycol) methyl ether, and PEG stands for poly(ethylene glycol) methyl ether.)

FIG. 4 illustrates (A) a graph showing the concentration-dependent inhibitory effect of the multivalent ligands according to the present invention on binding of [$^{125}$I] echistatin to the $\alpha_v\beta_3$ integrin receptor, and (B) a graph showing the concentration-dependent inhibitory effect of the dendrimer conjugate Compounds 2a-2j without the ligand moieties which are the synthetic precursors of the multivalent ligands mentioned above on binding of [$^{125}$I]echistatin to the $\alpha_v\beta_3$ integrin receptor.

As illustrated in the above Table 1 and FIG. 4, a multivalent ligand according to the present invention effectively inhibited [$^{125}$I]echistatin binding to the $\alpha_v\beta_3$ integrin receptor at a very low subnanomolar concentration range, and thus the multivalent ligand according to the present invention has a significantly high avidity of multivalent binding.

Furthermore, the relative binding strength of the multivalent ligands according to the present invention as determined by IC$_{50}$ value was enhanced as high as $10^4$-fold relative to that of the corresponding monovalent ligand (Compound 16) through the efficient multivalent binding with the specific receptors overexpressed on the surface of tumor cells, and as such the multivalent ligand according to the present invention can significantly improve the diagnostic efficiency of tumor.

Experimental Example 3

Evaluation of Tumor Diagnostic Efficiency by SPECT Imaging

Radiolabeling of Dendrimer Conjugate Compounds 1a-1j

20 µL (0.012 µmole) of each 600 µM stock solutions of RGD-attached dendrimer conjugate Compounds 1a-1j prepared in Examples 1-10 in deionized water and 50 µL of [$^{125}$I]NaI (purchased from PerkinElmer) in saline at the concentration of 18.5 MBq were added to an Iodogen (pre-coated iodination tube, purchased from Pierce), and the reaction mixture was placed in a shaking incubator at 25° C. for 10 min. For all dendrimer conjugate Compounds 1a-1j, the degree of radioiodination (i.e., labeling efficiency) as analyzed by instant thin layer chromatography (ITLC) in 0.9% saline (eluent) was determined to be higher than 95%.

The crude reaction mixture of each $^{125}$I-labeled dendrimer conjugate Compounds 1a-1j (70 µL) was used for injection into a mouse without purification.

Evaluation of Tumor Diagnostic Efficiency of $^{125}$I-Labeled Dendrimer Conjugate Compounds 1a-1j by SPECT Imaging All animal studies were approved by the Institutional Animal Care and Use Committee of the National Cancer Center. 4 weeks old female Balb/c nude mice bearing U87MG tumors were used for the evaluation of tumor diagnostic efficiency by SPECT imaging. U87MG cells ($1\times10^6$ cells in 200 µL of PBS) were implanted subcutaneously into the right hind hip of each mouse. Once the tumor size reached 5 mm or larger by diameter, 70 µL of each the reaction mixture of $^{125}$I-labeled dendrimer conjugate Compound 1a-1j in saline was administered into the mouse by intravenous injection at a dose of 18.5 MBq. SPECT images were acquired using a NanoSPECT animal SPECT imaging system (purchased from Bioscan) at 2 h and 24 h post-injection. The obtained SPECT images were analyzed using the InVivoScope™ software (purchased from Bioscan), and the results are shown in FIGS. 5 and 6.

Figure 5:
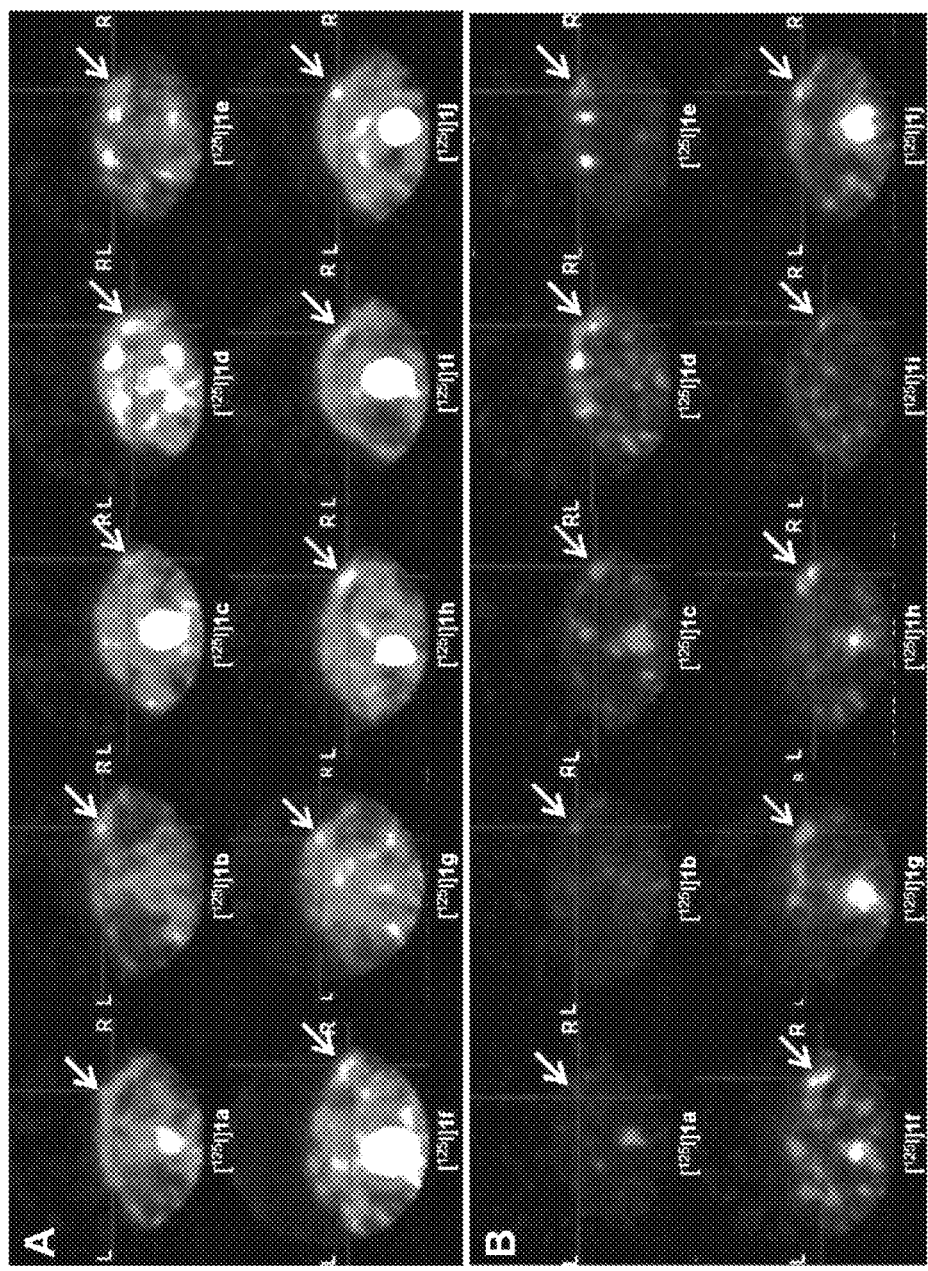
FIG. 5 illustrates the SPECT images (axial view) of U87MG tumor-bearing mice administered with the multivalent ligands 1a-1j according to the present invention after their radiolabeling with $^{125}$I (A: 2 h post-injection, B: 24 h post-injection).

FIG. 5 illustrates the results of SPECT imaging (axial view) of mice administered with the $^{125}$I-labeled multivalent ligands 1a-1j (A: 2 h post-injection, B: 24 h post-injection).

Figure 6:
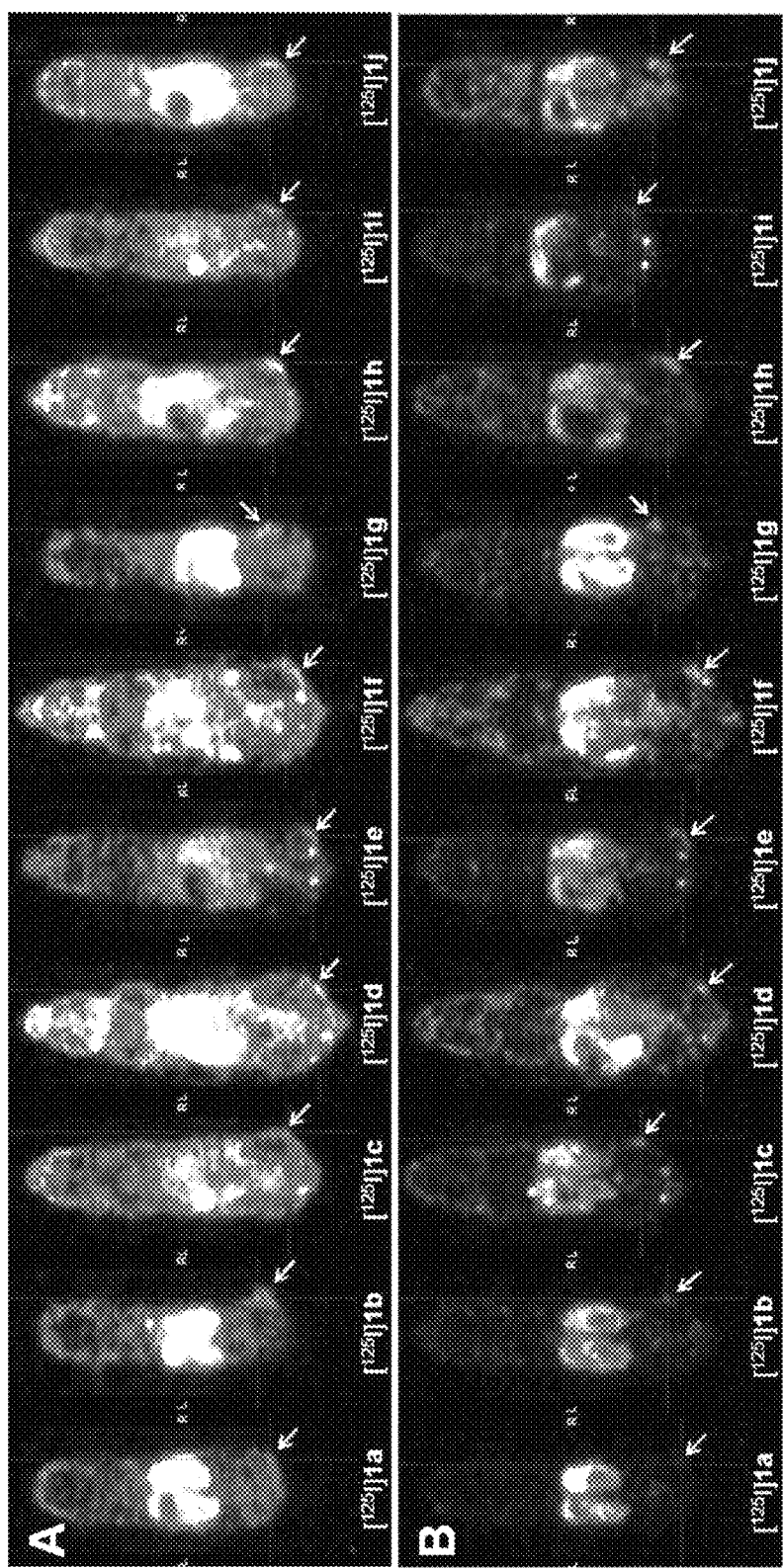
FIG. 6 illustrates the SPECT images (coronal view) of U87MG tumor-bearing mice administered with the multivalent ligands 1a-1j according to the present invention after their radiolabeling with $^{125}$I (A: 2 h post-injection, B: 24 h post-injection).

FIG. 6 illustrates the results of SPECT imaging (coronal view) of mice administered with the $^{125}$I-labeled multivalent ligands 1a-1j (A: 2 h post-injection, B: 24 h post-injection).

As illustrated in FIGS. 5 and 6, at 2 h post-injection, the radiolabeled multivalent ligands, dendrimer conjugate Compounds 1a-1j, existed in various organs including tumor; however, at 24 h post-injection, the radiolabeled dendrimer conjugate Compounds 1a-1j have been eliminated from most of the organs but a substantial amount was noticed specifically where the tumor was implanted.

Therefore, the avidity of the multivalent ligands according to the present invention is superior to form multivalent binding with the specific receptors overexpressed on the surface of tumor cells, and the diagnostic efficiency of tumor in vivo could be significantly improved.

What is claimed is:

1. A method to regulate the tumor diagnostic efficiency of a multivalent ligand by regulating the stoichiometric ratio between inner surface functionalities and ligand moieties for tumor targeting, wherein the multivalent ligand comprises:
    a single core consisting of a circular or spherical symmetric small molecular compound, or a radial-shaped macromolecule, wherein the core comprises terminal functional groups;
    said ligand moieties which are attached to a portion of the terminal functional groups of the core through a spacer;
    said inner surface functionalities comprising the terminal functional groups, modified terminal functional groups or the combination thereof; and
    one or more imaging agents which are attached to another portion of the terminal functional groups of the core;
    wherein the inner surface functionalities interact attractively with the surface of the tumor; and
    wherein the number of ligand moieties for tumor targeting accounts for 5-90% of the total number of inner surface functionalities and ligand moieties for tumor targeting.

2. The method as set forth in claim 1, wherein the inner surface functionality is one or more selected from the group consisting of —OH, —OR, —NH$_2$, —NR$_2$, —NHC(=O) CH$_3$, —NHC(=O)CR$_3$, —SH, —SR, —C(=O)OH, —C(=O)OR, —C(=O)R, —C(=O)NR$_2$, —NHC(=O) NR$_2$, —C(=S)NR$_2$, —NHC(=S)NR$_2$, —(OCH$_2$CH$_2$)$_n$ OCH₃, and —(OCH₂CH₂)ₙOR, wherein R is H, or a linear or branched $C_{1-6}$ alkyl group, and n is an integer between 1 and 100.

3. The method as set forth in claim 1, wherein the ligand moiety for tumor targeting binds specifically to the receptor expressed on the surface of tumor cells.

4. The method as set forth in claim 1, wherein the number of ligand moieties for tumor targeting accounts for 10-60% of the total number of inner surface functionalities and ligand moieties for tumor targeting.

5. The method as set forth in claim 1, wherein the terminal functional group of the core is not modified if the terminal functional group of the core is identical to the inner surface functionality.

6. The method as set forth in claim 1, wherein 1) the circular or spherical symmetric small molecular compound constituting the core is one selected from the group consisting of: one of the carbohydrates selected from the group consisting of α-, β-, and γ-cyclodextrins, glucose, galactose, and mannose; porphyrin; 1,4,7,10-tetraazacyclododecane-1,4,7,10-tetraacetic acid (DOTA); a cyclic peptide formed by connecting 2 to 4 amino acids wherein the amino acid is one or more selected from the group consisting of lysine, aspartic acid, glutamic acid, serine, cysteine, and tyrosine; and
2) the radial-shaped macromolecule constituting the core is one selected from the group consisting of: one of the dendrimers selected from the group consisting of a polyamidoamine (PAMAM) dendrimer, a polylysine dendrimer, a polyimine (PI) dendrimer, a poly(propylene imine) (PPI) dendrimer, a polyester dendrimer, a polyether dendrimer, a polyglutamic acid dendrimer, a polyaspartic acid dendrimer, a polyglycerol dendrimer, and a polymelamine dendrimer; one of the hyperbranched polymers selected from the group consisting of polylysine, polyester, polyether, polyglutamic acid, polyaspartic acid, and polyglycerol; and one of the star-shaped polymers selected from the group consisting of polyethylene glycol (PEG) and copolymers thereof.

7. The method as set forth in claim 1, wherein the spacer is a linear biocompatible polymer consisting of either one or a copolymer of two or three selected from the group consisting of polyethylene glycol (PEG), polypropylene oxide, polyester, polyether, polyurethane, polyanhydride, polyethylene, polypropylene, polysiloxane, polysulfone, polyglycolic acid, polylactic acid, polycaprolactone, polyacrylate, polyvinyl alcohol, and polypeptide.

8. The method as set forth in claim 1, wherein the imaging agent is one or more selected from the group consisting of fluorescent dyes, precursors for radiolabeling, and contrast agent moieties for magnetic resonance imaging (MRI) or computed tomography (CT).

9. The method as set forth in claim 8, wherein the precursors for radiolabeling are administered in vivo for tumor diagnosis after being labeled with radioisotopes.

\* \* \* \* \*